(12) United States Patent
Yuan et al.

(10) Patent No.: US 9,198,766 B2
(45) Date of Patent: Dec. 1, 2015

(54) PROSTHESES, TOOLS, AND METHODS FOR REPLACEMENT OF NATURAL FACET JOINTS WITH ARTIFICIAL FACET JOINT SURFACES

(75) Inventors: Hansen Yuan, Fayetteville, NY (US);
Mark A. Reiley, Piedmont, CA (US);
David Stinson, Woodinville, WA (US);
Lawrence R. Jones, Confier, CO (US)

(73) Assignee: GMEDELAWARE 2 LLC, Audubon, PA (US)

( * ) Notice: Subject to any disclaimer, the term of this patent is extended or adjusted under 35 U.S.C. 154(b) by 1483 days.

(21) Appl. No.: 12/027,899

(22) Filed: Feb. 7, 2008

(65) Prior Publication Data

US 2008/0125814 A1    May 29, 2008

Related U.S. Application Data

(60) Division of application No. 10/973,834, filed on Oct. 25, 2004, now Pat. No. 7,608,104, which is a continuation-in-part of application No. 10/438,294, filed on May 14, 2003, now abandoned.

(60) Provisional application No. 60/567,933, filed on May 3, 2004.

(51) Int. Cl.
*A61F 2/44* (2006.01)
*A61B 17/17* (2006.01)
(Continued)

(52) U.S. Cl.
CPC ........... *A61F 2/4405* (2013.01); *A61B 17/1757* (2013.01); *A61F 2/4611* (2013.01); *A61B 17/86* (2013.01); *A61F 2/442* (2013.01); *A61F 2002/30153* (2013.01); *A61F 2002/30156* (2013.01); *A61F 2002/30242* (2013.01); *A61F 2002/30331* (2013.01); *A61F 2002/30332* (2013.01); *A61F 2002/30405* (2013.01); *A61F 2002/30484* (2013.01); *A61F 2002/30495* (2013.01); *A61F 2002/30509* (2013.01); *A61F 2002/30614* (2013.01);
(Continued)

(58) Field of Classification Search
CPC .. A61F 2/4405; A61F 2/4611; Y10S 623/902
USPC .................... 623/17.11–17.16; 606/247–249
See application file for complete search history.

(56) References Cited

U.S. PATENT DOCUMENTS

| | | |
|---|---|---|
| 1,308,451 A | 7/1919 | Schachat |
| 2,502,902 A | 4/1950 | Tofflemire |

(Continued)

FOREIGN PATENT DOCUMENTS

| | | |
|---|---|---|
| DE | 10135771 A1 | 7/2001 |
| DE | 10312755 A1 | 10/2003 |

(Continued)

OTHER PUBLICATIONS

Ochoa et al.; U.S. Appl. No. 12/377,546 entitled "Spinal implant," filed Feb. 13, 2009.

(Continued)

*Primary Examiner* — Paul Prebilic

(57) ABSTRACT

Cephalad and caudal vertebral facet joint prostheses and methods of use are provided. The cephalad prostheses are adapted and configured to be attached to a lamina portion of a vertebra without blocking a pedicle portion of the cephalad vertebra.

20 Claims, 42 Drawing Sheets

(51) Int. Cl.
*A61F 2/46* (2006.01)
*A61B 17/86* (2006.01)
*A61F 2/30* (2006.01)

(52) U.S. Cl.
CPC .......... *A61F 2002/30616* (2013.01); *A61F 2002/30649* (2013.01); *A61F 2002/30772* (2013.01); *A61F 2002/30795* (2013.01); *A61F 2002/30841* (2013.01); *A61F 2002/30904* (2013.01); *A61F 2002/4628* (2013.01); *A61F 2002/4629* (2013.01); *A61F 2002/4631* (2013.01); *A61F 2002/4635* (2013.01); *A61F 2220/0025* (2013.01); *A61F 2220/0033* (2013.01); *A61F 2230/0019* (2013.01); *A61F 2230/0023* (2013.01); *A61F 2230/0071* (2013.01); *A61F 2310/00017* (2013.01); *A61F 2310/00023* (2013.01); *A61F 2310/00029* (2013.01); *A61F 2310/00047* (2013.01); *A61F 2310/0097* (2013.01); *A61F 2310/00131* (2013.01); *A61F 2310/00179* (2013.01); *A61F 2310/00796* (2013.01); *A61F 2310/00976* (2013.01)

(56) References Cited

U.S. PATENT DOCUMENTS

| | | | |
|---|---|---|---|
| 2,930,133 | A | 3/1960 | Thompson |
| 2,959,861 | A | 11/1960 | Stromquist |
| 3,596,656 | A | 8/1971 | Kaute |
| 3,710,789 | A | 1/1973 | Ersek |
| 3,726,279 | A | 4/1973 | Barefoot et al. |
| 3,867,728 | A | 2/1975 | Stubstad et al. |
| 3,875,595 | A | 4/1975 | Froning |
| 3,941,127 | A | 3/1976 | Froning |
| 4,040,130 | A | 8/1977 | Laure |
| 4,123,848 | A | 11/1978 | Emmerich et al. |
| 4,156,296 | A | 5/1979 | Johnson et al. |
| 4,210,317 | A | 7/1980 | Spann et al. |
| 4,231,121 | A | 11/1980 | Lewis |
| 4,271,836 | A | 6/1981 | Bacal et al. |
| 4,349,921 | A | 9/1982 | Kuntz |
| 4,394,370 | A | 7/1983 | Jefferies |
| 4,472,840 | A | 9/1984 | Jefferies |
| 4,502,161 | A | 3/1985 | Wall |
| 4,554,914 | A | 11/1985 | Kapp et al. |
| 4,611,581 | A | 9/1986 | Steffee |
| 4,633,722 | A | 1/1987 | Beardmore et al. |
| 4,693,722 | A | 9/1987 | Wall |
| 4,697,582 | A | 10/1987 | William |
| 4,710,075 | A | 12/1987 | Davison |
| 4,759,769 | A | 7/1988 | Hedman et al. |
| 4,772,287 | A | 9/1988 | Ray et al. |
| 4,778,472 | A | 10/1988 | Homsy et al. |
| 4,795,469 | A | 1/1989 | Oh |
| 4,805,602 | A | 2/1989 | Puno et al. |
| 4,863,477 | A | 9/1989 | Monson |
| 4,904,260 | A | 2/1990 | Ray et al. |
| 4,911,718 | A | 3/1990 | Lee et al. |
| 4,917,701 | A | 4/1990 | Morgan |
| 4,932,975 | A | 6/1990 | Main et al. |
| 4,950,270 | A | 8/1990 | Bowman et al. |
| 4,955,916 | A | 9/1990 | Carignan et al. |
| 4,957,495 | A | 9/1990 | Kluger |
| 4,987,904 | A | 1/1991 | Wilson |
| 5,000,165 | A | 3/1991 | Watanabe |
| 5,015,255 | A | 5/1991 | Kuslich |
| 5,019,081 | A | 5/1991 | Watanabe |
| 5,047,055 | A | 9/1991 | Bao et al. |
| 5,062,845 | A | 11/1991 | Kuslich et al. |
| 5,070,623 | A | 12/1991 | Barnes |
| 5,071,437 | A | 12/1991 | Steffee |
| 5,092,866 | A | 3/1992 | Breard et al. |
| 5,098,434 | A | 3/1992 | Serbousek |
| 5,108,399 | A | 4/1992 | Eitenmuller et al. |
| 5,129,900 | A | 7/1992 | Asher et al. |
| 5,147,404 | A | 9/1992 | Downey |
| 5,171,280 | A | 12/1992 | Baumgartner |
| 5,192,326 | A | 3/1993 | Bao et al. |
| 5,258,031 | A | 11/1993 | Salib et al. |
| 5,261,910 | A | 11/1993 | Warden et al. |
| 5,284,655 | A | 2/1994 | Bogdansky et al. |
| 5,300,073 | A | 4/1994 | Ray et al. |
| 5,303,480 | A | 4/1994 | Chek |
| 5,306,308 | A | 4/1994 | Gross et al. |
| 5,306,309 | A | 4/1994 | Wagner et al. |
| 5,312,409 | A | 5/1994 | McLaughlin et al. |
| 5,314,429 | A | 5/1994 | Goble |
| 5,314,476 | A | 5/1994 | Prewett et al. |
| 5,314,486 | A | 5/1994 | Zang et al. |
| 5,314,489 | A | 5/1994 | Hoffman et al. |
| 5,314,492 | A | 5/1994 | Hamilton et al. |
| 5,329,933 | A | 7/1994 | Graf |
| 5,334,203 | A | 8/1994 | Wagner |
| 5,348,026 | A | 9/1994 | Davidson |
| 5,350,380 | A | 9/1994 | Goble et al. |
| 5,360,448 | A | 11/1994 | Thramann |
| 5,370,697 | A | 12/1994 | Baumgartner |
| 5,401,269 | A | 3/1995 | Buttner-Janz et al. |
| 5,405,390 | A | 4/1995 | O'Leary et al. |
| 5,413,576 | A * | 5/1995 | Rivard ............... 606/250 |
| 5,415,659 | A | 5/1995 | Lee et al. |
| 5,415,661 | A | 5/1995 | Holmes |
| 5,425,773 | A | 6/1995 | Boyd et al. |
| 5,437,669 | A | 8/1995 | Yuan et al. |
| 5,437,672 | A | 8/1995 | Alleyne |
| 5,443,483 | A | 8/1995 | Kirsch |
| 5,445,639 | A | 8/1995 | Kuslich et al. |
| 5,458,641 | A | 10/1995 | Ramirez Jimenez |
| 5,458,642 | A | 10/1995 | Beer et al. |
| 5,458,643 | A | 10/1995 | Oka et al. |
| 5,470,333 | A | 11/1995 | Ray |
| 5,474,551 | A | 12/1995 | Finn et al. |
| 5,474,555 | A | 12/1995 | Puno et al. |
| 5,484,437 | A * | 1/1996 | Michelson ............... 606/86 A |
| 5,491,882 | A | 2/1996 | Walston et al. |
| 5,496,318 | A | 3/1996 | Howland et al. |
| 5,501,684 | A | 3/1996 | Schlapfer et al. |
| 5,507,823 | A | 4/1996 | Walston et al. |
| 5,510,396 | A | 4/1996 | Prewett et al. |
| 5,514,180 | A | 5/1996 | Heggeness et al. |
| 5,527,312 | A | 6/1996 | Ray |
| 5,534,028 | A | 7/1996 | Bao et al. |
| 5,534,030 | A | 7/1996 | Navarro et al. |
| 5,545,229 | A | 8/1996 | Parsons et al. |
| 5,556,431 | A | 9/1996 | Buttner-Janz |
| 5,562,738 | A | 10/1996 | Boyd et al. |
| 5,569,247 | A | 10/1996 | Morrison |
| 5,571,189 | A | 11/1996 | Kuslich |
| 5,571,191 | A | 11/1996 | Fitz |
| 5,575,792 | A | 11/1996 | Errico et al. |
| 5,577,995 | A | 11/1996 | Walker et al. |
| 5,587,695 | A | 12/1996 | Warmerdam |
| 5,599,311 | A | 2/1997 | Raulerson |
| 5,603,713 | A | 2/1997 | Aust et al. |
| 5,609,641 | A | 3/1997 | Johnson et al. |
| 5,643,263 | A | 7/1997 | Simonson |
| 5,645,597 | A | 7/1997 | Krapiva |
| 5,645,599 | A | 7/1997 | Samani |
| 5,649,930 | A | 7/1997 | Kertzner |
| 5,653,762 | A | 8/1997 | Pisharodi |
| 5,658,338 | A | 8/1997 | Tullos et al. |
| 5,662,651 | A | 9/1997 | Tornier et al. |
| 5,672,175 | A | 9/1997 | Martin |
| 5,674,295 | A | 10/1997 | Ray et al. |
| 5,674,296 | A | 10/1997 | Bryan et al. |
| 5,676,701 | A | 10/1997 | Yuan et al. |
| 5,678,317 | A | 10/1997 | Stefanakos |
| 5,683,391 | A | 11/1997 | Boyd |
| 5,683,392 | A | 11/1997 | Richelsoph et al. |
| 5,683,464 | A | 11/1997 | Wagner et al. |
| 5,683,466 | A | 11/1997 | Vitale |
| 5,688,274 | A | 11/1997 | Errico et al. |

(56) References Cited

U.S. PATENT DOCUMENTS

| | | |
|---|---|---|
| 5,690,630 A | 11/1997 | Errico et al. |
| 5,700,268 A | 12/1997 | Bertin |
| 5,702,450 A * | 12/1997 | Bisserie .................. 623/17.16 |
| 5,704,941 A | 1/1998 | Jacober et al. |
| 5,716,415 A | 2/1998 | Steffee |
| 5,725,527 A | 3/1998 | Biedermann et al. |
| 5,733,284 A | 3/1998 | Martin |
| 5,738,585 A | 4/1998 | Hoyt, III et al. |
| 5,741,253 A * | 4/1998 | Michelson .................. 606/86 A |
| 5,741,255 A | 4/1998 | Krag et al. |
| 5,741,261 A | 4/1998 | Moskovitz et al. |
| 5,766,253 A | 6/1998 | Brosnahan, III |
| 5,776,135 A | 7/1998 | Errico et al. |
| 5,782,833 A | 7/1998 | Haider |
| 5,797,911 A | 8/1998 | Sherman et al. |
| 5,800,433 A | 9/1998 | Benzel et al. |
| 5,824,093 A | 10/1998 | Ray et al. |
| 5,824,094 A | 10/1998 | Serhan et al. |
| 5,827,289 A | 10/1998 | Reiley et al. |
| 5,836,948 A | 11/1998 | Zucherman et al. |
| 5,860,977 A | 1/1999 | Zucherman et al. |
| 5,863,293 A | 1/1999 | Richelsoph |
| 5,865,846 A | 2/1999 | Bryan et al. |
| 5,866,113 A | 2/1999 | Hendriks et al. |
| 5,868,745 A | 2/1999 | Alleyne |
| 5,879,350 A | 3/1999 | Sherman et al. |
| 5,879,396 A | 3/1999 | Walston et al. |
| 5,885,285 A | 3/1999 | Simonson |
| 5,885,286 A | 3/1999 | Sherman et al. |
| 5,891,145 A | 4/1999 | Morrison et al. |
| 5,893,889 A | 4/1999 | Harrington |
| RE36,221 E | 6/1999 | Breard et al. |
| 5,947,893 A | 9/1999 | Agrawal et al. |
| 5,947,965 A | 9/1999 | Bryan |
| 5,964,760 A | 10/1999 | Richelsoph |
| 5,984,926 A | 11/1999 | Jones |
| 6,001,130 A | 12/1999 | Bryan et al. |
| 6,004,353 A | 12/1999 | Masini |
| 6,010,503 A | 1/2000 | Richelsoph et al. |
| 6,014,588 A | 1/2000 | Fitz |
| 6,019,759 A | 2/2000 | Rogozinski |
| 6,019,792 A | 2/2000 | Cauthen |
| 6,022,350 A | 2/2000 | Ganem |
| 6,039,763 A | 3/2000 | Shelokov |
| 6,048,342 A | 4/2000 | Zucherman et al. |
| 6,050,997 A | 4/2000 | Mullane |
| 6,053,917 A | 4/2000 | Sherman et al. |
| 6,063,121 A | 5/2000 | Xavier et al. |
| 6,066,325 A | 5/2000 | Wallace et al. |
| 6,068,630 A | 5/2000 | Zucherman et al. |
| RE36,758 E | 6/2000 | Fitz |
| 6,074,391 A | 6/2000 | Metz-Stavenhagen et al. |
| 6,077,262 A | 6/2000 | Schläpfer et al. |
| 6,080,157 A | 6/2000 | Cathro et al. |
| 6,086,590 A | 7/2000 | Margulies et al. |
| 6,090,111 A | 7/2000 | Nichols |
| 6,113,600 A | 9/2000 | Drummond et al. |
| 6,113,637 A | 9/2000 | Gill et al. |
| 6,120,510 A | 9/2000 | Albrektsson et al. |
| 6,132,430 A | 10/2000 | Wagner |
| 6,132,462 A | 10/2000 | Li |
| 6,132,464 A * | 10/2000 | Martin .................. 623/17.15 |
| 6,132,465 A | 10/2000 | Ray et al. |
| 6,165,177 A | 12/2000 | Wilson et al. |
| 6,190,388 B1 | 2/2001 | Michelson et al. |
| 6,193,724 B1 | 2/2001 | Chan |
| 6,193,758 B1 | 2/2001 | Huebner |
| 6,200,322 B1 | 3/2001 | Branch et al. |
| 6,214,012 B1 | 4/2001 | Karpman et al. |
| 6,224,602 B1 | 5/2001 | Hayes |
| 6,231,575 B1 | 5/2001 | Krag |
| 6,248,105 B1 | 6/2001 | Schläpfer et al. |
| 6,280,443 B1 | 8/2001 | Gu et al. |
| 6,290,703 B1 | 9/2001 | Ganem |
| 6,293,949 B1 | 9/2001 | Justis et al. |
| 6,302,890 B1 | 10/2001 | Leone, Jr. |
| 6,309,391 B1 | 10/2001 | Crandall et al. |
| 6,312,431 B1 | 11/2001 | Asfora |
| 6,340,361 B1 | 1/2002 | Kraus et al. |
| 6,340,477 B1 | 1/2002 | Anderson |
| 6,342,054 B1 | 1/2002 | Mata |
| 6,361,506 B1 | 3/2002 | Saenger et al. |
| 6,368,320 B1 | 4/2002 | Le Couedic et al. |
| 6,419,703 B1 | 7/2002 | Fallin et al. |
| 6,440,169 B1 | 8/2002 | Elberg et al. |
| 6,443,954 B1 | 9/2002 | Bramlet et al. |
| 6,451,021 B1 | 9/2002 | Ralph et al. |
| 6,471,705 B1 | 10/2002 | Biedermann et al. |
| 6,514,253 B1 | 2/2003 | Yao |
| 6,520,963 B1 | 2/2003 | McKinley |
| 6,524,315 B1 | 2/2003 | Selvitelli et al. |
| 6,540,749 B2 | 4/2003 | Schäfer et al. |
| 6,547,790 B2 | 4/2003 | Harkey, III et al. |
| 6,554,843 B1 | 4/2003 | Ou |
| 6,565,565 B1 | 5/2003 | Yuan et al. |
| 6,565,572 B2 | 5/2003 | Chappius |
| 6,565,605 B2 | 5/2003 | Goble et al. |
| 6,572,617 B1 | 6/2003 | Senegas |
| 6,579,319 B2 | 6/2003 | Goble et al. |
| 6,585,740 B2 | 7/2003 | Schlapfer et al. |
| 6,585,769 B1 | 7/2003 | Muhanna et al. |
| 6,607,530 B1 | 8/2003 | Carl et al. |
| 6,610,091 B1 | 8/2003 | Reiley |
| 6,619,091 B2 | 9/2003 | Heffe |
| 6,623,485 B2 | 9/2003 | Doubler et al. |
| 6,626,909 B2 | 9/2003 | Chin |
| 6,632,226 B2 | 10/2003 | Chan |
| 6,638,281 B2 | 10/2003 | Gorek |
| 6,645,214 B2 | 11/2003 | Brown et al. |
| 6,648,891 B2 | 11/2003 | Kim |
| 6,669,698 B1 | 12/2003 | Tromanhauser et al. |
| 6,669,729 B2 | 12/2003 | Chin |
| 6,679,915 B1 * | 1/2004 | Cauthen .................. 623/17.11 |
| 6,712,818 B1 | 3/2004 | Michelson |
| 6,712,849 B2 | 3/2004 | Re et al. |
| 6,736,815 B2 | 5/2004 | Ginn |
| 6,749,361 B2 | 6/2004 | Hermann et al. |
| 6,761,698 B2 | 7/2004 | Shibata et al. |
| 6,761,720 B1 | 7/2004 | Senegas |
| 6,770,095 B2 | 8/2004 | Grinberg et al. |
| 6,783,527 B2 | 8/2004 | Drewry et al. |
| 6,790,233 B2 | 9/2004 | Brodke et al. |
| 6,793,678 B2 | 9/2004 | Hawkins |
| 6,802,844 B2 | 10/2004 | Ferree |
| 6,811,567 B2 | 11/2004 | Reiley |
| 6,902,567 B2 | 6/2005 | Del Medico |
| 6,902,580 B2 | 6/2005 | Fallin et al. |
| 6,908,465 B2 | 6/2005 | von Hoffmann et al. |
| 6,949,123 B2 | 9/2005 | Reiley |
| 6,974,478 B2 | 12/2005 | Reiley et al. |
| 6,979,299 B2 | 12/2005 | Peabody et al. |
| 7,011,658 B2 | 3/2006 | Young |
| 7,044,969 B2 | 5/2006 | Errico et al. |
| 7,051,451 B2 | 5/2006 | Augostino et al. |
| 7,220,262 B1 | 5/2007 | Hynes |
| 7,294,127 B2 | 11/2007 | Leung et al. |
| 7,302,288 B1 | 11/2007 | Schellenberg |
| 7,309,338 B2 | 12/2007 | Cragg |
| 7,377,942 B2 * | 5/2008 | Berry .................. 623/17.11 |
| 7,445,635 B2 | 11/2008 | Fallin et al. |
| 7,455,685 B2 | 11/2008 | Justis |
| 7,547,324 B2 | 6/2009 | Cragg et al. |
| 2001/0012938 A1 | 8/2001 | Zucherman et al. |
| 2001/0020170 A1 | 9/2001 | Zucherman et al. |
| 2002/0013585 A1 | 1/2002 | Gournay et al. |
| 2002/0013588 A1 | 1/2002 | Landry et al. |
| 2002/0029039 A1 | 3/2002 | Zucherman et al. |
| 2002/0042613 A1 | 4/2002 | Mata |
| 2002/0049446 A1 | 4/2002 | Harkey, III et al. |
| 2002/0052603 A1 | 5/2002 | Nickols et al. |
| 2002/0065557 A1 | 5/2002 | Goble et al. |
| 2002/0068975 A1 | 6/2002 | Teitelbaum et al. |
| 2002/0082601 A1 | 6/2002 | Toyama et al. |
| 2002/0120272 A1 | 8/2002 | Yuan et al. |

(56) References Cited

U.S. PATENT DOCUMENTS

| | | |
|---|---|---|
| 2002/0123752 A1 | 9/2002 | Schultheiss et al. |
| 2002/0123806 A1 | 9/2002 | Reiley |
| 2002/0151895 A1 | 10/2002 | Soboleski et al. |
| 2003/0004572 A1* | 1/2003 | Goble et al. ............... 623/17.11 |
| 2003/0028250 A1* | 2/2003 | Reiley et al. ............... 623/17.11 |
| 2003/0040797 A1 | 2/2003 | Fallin et al. |
| 2003/0055427 A1 | 3/2003 | Graf |
| 2003/0069603 A1 | 4/2003 | Little et al. |
| 2003/0125740 A1 | 7/2003 | Khanna |
| 2003/0181914 A1 | 9/2003 | Johnson et al. |
| 2003/0191532 A1 | 10/2003 | Goble et al. |
| 2003/0195631 A1 | 10/2003 | Ferree |
| 2003/0204259 A1 | 10/2003 | Goble et al. |
| 2003/0204261 A1 | 10/2003 | Eisermann et al. |
| 2003/0233148 A1 | 12/2003 | Ferree |
| 2004/0006391 A1 | 1/2004 | Reiley |
| 2004/0049205 A1 | 3/2004 | Lee et al. |
| 2004/0049272 A1 | 3/2004 | Reiley |
| 2004/0049273 A1 | 3/2004 | Reiley |
| 2004/0049274 A1 | 3/2004 | Reiley |
| 2004/0049275 A1 | 3/2004 | Reiley |
| 2004/0049276 A1 | 3/2004 | Reiley |
| 2004/0049277 A1 | 3/2004 | Reiley |
| 2004/0049278 A1 | 3/2004 | Reiley |
| 2004/0049281 A1 | 3/2004 | Reiley |
| 2004/0059429 A1 | 3/2004 | Amin et al. |
| 2004/0093083 A1* | 5/2004 | Branch et al. ............... 623/17.11 |
| 2004/0111154 A1 | 6/2004 | Reiley |
| 2004/0116927 A1 | 6/2004 | Graf |
| 2004/0127989 A1 | 7/2004 | Dooris et al. |
| 2004/0143264 A1 | 7/2004 | McAfee |
| 2004/0204710 A1 | 10/2004 | Patel et al. |
| 2004/0204718 A1 | 10/2004 | Hoffman |
| 2004/0230201 A1 | 11/2004 | Yuan et al. |
| 2004/0230304 A1 | 11/2004 | Yuan et al. |
| 2004/0260305 A1 | 12/2004 | Gorensek et al. |
| 2004/0267279 A1 | 12/2004 | Casutt et al. |
| 2005/0010291 A1 | 1/2005 | Stinson et al. |
| 2005/0015146 A1 | 1/2005 | Louis et al. |
| 2005/0027359 A1 | 2/2005 | Mashburn |
| 2005/0027361 A1 | 2/2005 | Reiley |
| 2005/0033431 A1 | 2/2005 | Gordon et al. |
| 2005/0033432 A1 | 2/2005 | Gordon et al. |
| 2005/0033434 A1 | 2/2005 | Berry |
| 2005/0033439 A1 | 2/2005 | Gordon et al. |
| 2005/0043799 A1 | 2/2005 | Reiley |
| 2005/0049705 A1* | 3/2005 | Hale et al. ............... 623/17.11 |
| 2005/0055096 A1 | 3/2005 | Serhan et al. |
| 2005/0059972 A1 | 3/2005 | Biscup |
| 2005/0080428 A1 | 4/2005 | White |
| 2005/0080486 A1 | 4/2005 | Fallin et al. |
| 2005/0085912 A1 | 4/2005 | Arnin et al. |
| 2005/0101956 A1 | 5/2005 | Simonson |
| 2005/0102028 A1 | 5/2005 | Arnin et al. |
| 2005/0119748 A1 | 6/2005 | Reiley et al. |
| 2005/0131406 A1 | 6/2005 | Reiley et al. |
| 2005/0131409 A1 | 6/2005 | Chervitz et al. |
| 2005/0131537 A1 | 6/2005 | Hoy et al. |
| 2005/0131538 A1 | 6/2005 | Chervitz et al. |
| 2005/0131545 A1 | 6/2005 | Chervitz et al. |
| 2005/0137705 A1 | 6/2005 | Reiley |
| 2005/0137706 A1 | 6/2005 | Reiley |
| 2005/0143818 A1 | 6/2005 | Yuan et al. |
| 2005/0149190 A1 | 7/2005 | Reiley |
| 2005/0159746 A1 | 7/2005 | Grob et al. |
| 2005/0165484 A1 | 7/2005 | Ferree |
| 2005/0177240 A1 | 8/2005 | Blain |
| 2005/0187560 A1 | 8/2005 | Dietzel et al. |
| 2005/0192589 A1 | 9/2005 | Raymond et al. |
| 2005/0203533 A1 | 9/2005 | Ferguson et al. |
| 2005/0222683 A1 | 10/2005 | Berry |
| 2005/0228500 A1 | 10/2005 | Kim et al. |
| 2005/0234552 A1 | 10/2005 | Reiley |
| 2005/0240264 A1* | 10/2005 | Tokish et al. ............... 623/17.11 |
| 2005/0240265 A1 | 10/2005 | Kuiper et al. |
| 2005/0240266 A1 | 10/2005 | Kuiper et al. |
| 2005/0251256 A1 | 11/2005 | Reiley |
| 2005/0261770 A1 | 11/2005 | Kuiper et al. |
| 2005/0267579 A1 | 12/2005 | Reiley et al. |
| 2005/0273167 A1 | 12/2005 | Triplett et al. |
| 2005/0277922 A1 | 12/2005 | Trieu et al. |
| 2005/0283238 A1 | 12/2005 | Reiley |
| 2006/0009847 A1 | 1/2006 | Reiley |
| 2006/0009848 A1 | 1/2006 | Reiley |
| 2006/0009849 A1 | 1/2006 | Reiley |
| 2006/0025769 A1 | 2/2006 | Dick et al. |
| 2006/0029186 A1 | 2/2006 | De Villiers et al. |
| 2006/0036246 A1 | 2/2006 | Carl et al. |
| 2006/0041311 A1 | 2/2006 | McLeer |
| 2006/0041314 A1 | 2/2006 | Millard |
| 2006/0052785 A1 | 3/2006 | Augostino et al. |
| 2006/0058790 A1 | 3/2006 | Carl et al. |
| 2006/0058791 A1 | 3/2006 | Broman et al. |
| 2006/0079895 A1 | 4/2006 | McLeer |
| 2006/0085010 A1 | 4/2006 | Lieberman |
| 2006/0085072 A1 | 4/2006 | Funk et al. |
| 2006/0085075 A1 | 4/2006 | McLeer |
| 2006/0100707 A1 | 5/2006 | Stinson et al. |
| 2006/0100709 A1 | 5/2006 | Reiley et al. |
| 2006/0122703 A1 | 6/2006 | Aebi et al. |
| 2006/0149375 A1 | 7/2006 | Yuan et al. |
| 2006/0184180 A1 | 8/2006 | Augostino et al. |
| 2006/0241532 A1 | 10/2006 | Murakami et al. |
| 2006/0265070 A1 | 11/2006 | Stinson et al. |
| 2007/0079517 A1 | 4/2007 | Augostino et al. |
| 2007/0088358 A1 | 4/2007 | Yuan et al. |
| 2007/0093833 A1 | 4/2007 | Kuiper et al. |
| 2007/0168029 A1 | 7/2007 | Yuan et al. |
| 2007/0233256 A1 | 10/2007 | Ohrt et al. |
| 2007/0255411 A1 | 11/2007 | Reiley |
| 2007/0265706 A1 | 11/2007 | Reiley et al. |
| 2007/0276370 A1 | 11/2007 | Altarac et al. |
| 2007/0276374 A1 | 11/2007 | Broman et al. |
| 2007/0282445 A1 | 12/2007 | Reiley |
| 2008/0015583 A1 | 1/2008 | Reiley |
| 2008/0015696 A1 | 1/2008 | Reiley |
| 2014/0052248 A1* | 2/2014 | Kuiper et al. ............... 623/17.11 |

FOREIGN PATENT DOCUMENTS

| | | | |
|---|---|---|---|
| EP | 1103226 | | 5/2001 |
| EP | 1205152 A1 | | 5/2002 |
| EP | 1254639 A1 | | 11/2002 |
| FR | 2726459 | | 5/1996 |
| FR | 2749155 | | 12/1997 |
| FR | 2844180 | | 3/2004 |
| IE | S970323 | | 6/1998 |
| JP | 59010807 A | | 1/1984 |
| JP | 10082605 A | | 3/1998 |
| JP | 10179622 A | | 7/1998 |
| WO | WO 95/05783 A1 | | 3/1995 |
| WO | WO 96/00049 A1 | | 1/1996 |
| WO | WO 98/48717 A1 | | 11/1998 |
| WO | WO-98/48717 A1 * | 11/1998 | ............... A61F 17/70 |
| WO | WO 98/56301 A1 | | 12/1998 |
| WO | WO 99/05995 A1 | | 2/1999 |
| WO | WO 99/23963 A1 | | 5/1999 |
| WO | WO 99/60957 A1 | | 12/1999 |
| WO | WO 99/65412 A1 | | 12/1999 |
| WO | WO 00/38582 A1 | | 7/2000 |
| WO | WO 00/62684 A1 | | 10/2000 |
| WO | WO 01/06939 A1 | | 2/2001 |
| WO | WO 01/15638 A1 | | 3/2001 |
| WO | WO 01/28442 A1 | | 4/2001 |
| WO | WO 01/30248 A1 | | 5/2001 |
| WO | WO 01/39678 A1 | | 6/2001 |
| WO | WO 01/67972 A2 | | 9/2001 |
| WO | WO 01/97721 A2 | | 12/2001 |
| WO | WO 02/00270 A1 | | 1/2002 |
| WO | WO 02/00275 A1 | | 1/2002 |
| WO | WO 02/02024 A1 | | 1/2002 |
| WO | WO 02/02158 A1 | | 1/2002 |
| WO | WO 02/34150 A2 | | 5/2002 |
| WO | WO 02/43603 A1 | | 6/2002 |

(56) References Cited

FOREIGN PATENT DOCUMENTS

| WO | WO 02/071960 A1 | 9/2002 |
|---|---|---|
| WO | WO 02/089712 A1 | 11/2002 |
| WO | WO 03/020143 A1 | 3/2003 |
| WO | WO 03/041618 A2 | 5/2003 |
| WO | WO 03/075805 A1 | 9/2003 |
| WO | WO 03/101350 A1 | 12/2003 |
| WO | WO 2004/071358 A1 | 8/2004 |
| WO | WO 2004/103227 A1 | 12/2004 |
| WO | WO 2004/103228 A1 | 12/2004 |
| WO | WO 2005/009301 A1 | 2/2005 |
| WO | WO 2005/079711 A1 | 9/2005 |

OTHER PUBLICATIONS

Hewko, Brian; U.S. Appl. No. 12/377,552 entitled "Spinal implant," filed Feb. 13, 2009.

Berg, et al; U.S. Appl. No. 11/800,895 entitled "Minimally Invasive Spine Restoration Systems, Devices, Methods, and Kits," filed May 7, 2007.

Reiley et al; U.S. Appl. No. 11/577,872 entitled "Facet Joint Prosthesis" which entered the U.S. from the National Phase Apr. 24, 2007.

Reiley et al; U.S. Appl. No. 11/577,923 entitled "Facet Joint Prostheses" filed Apr. 25, 2007.

Kuiper et al; U.S. Appl. No. 11/577,964 entitled "Crossbar Spinal Prosthesis Having a Modular Design and Systems for Treating Spinal Pathologies," filed Apr. 25, 2007.

Kuiper et al; U.S. Appl. No. 11/577,967 entitled "Crossbar Spinal Prosthesis having a Modular Design and Systems for Treating Spinal Pathologies," filed Apr. 25, 2007.

Reiley, Mark; U.S. Appl. No. 11/831,870 entitled "Prostheses systems and methods for replacement of natural facet joints with artificial facet joint surfaces," filed Jul. 31, 2007.

Ralph et al; U.S. Appl. No. 11/837,335 entitled "Angled Washer Polyaxial Connection for Dynamic Spine Prosthesis," filed Aug. 10, 2007.

Stone et al; U.S. Appl. No. 11/861,239 entitled "Facet Replacement Device Removal and Revision Systems and Methods" filed Sep. 25, 2007.

McLeer, Thomas, U.S. Appl. No. 11/934,724 entitled "Polymeric Joint Complex and Methods of Use" filed Nov. 2, 2007.

McLeer, Thomas, U.S. Appl. No. 11/934,720 entitled "Polymeric Joint Complex and Methods of Use" filed Nov. 2, 2007.

McLeer, Thomas, U.S. Appl. No. 11/934,719 entitled "Polymeric Joint Complex and Methods of Use" filed Nov. 2, 2007.

Reiley, Mark, U.S. Appl. No. 11/934,713 entitled "Facet arthroplasty devices and methods" filed Nov. 2, 2007.

Reiley, Mark, U.S. Appl. No. 11/939,540 entitled "Facet arthroplasty devices and methods" filed Nov. 13, 2007.

Reiley, Mark, U.S. Appl. No. 11/943,458 entitled "Facet arthroplasty devices and methods" filed Nov. 20, 2007.

Reiley, Mark, U.S. Appl. No. 11/949,007 entitled "Facet arthroplasty devices and methods" filed Nov. 30, 2007.

Reiley, Mark, U.S. Appl. No. 11/949,000 entitled "Facet arthroplasty devices and methods" filed Nov. 30, 2007.

Reiley et al.; U.S. Appl. No. 11/948,963 entitled "Prostheses, systems and methods for replacement of natural facet joints with artificial facet joint surfaces" filed Nov. 30, 2007.

Reiley, Mark, U.S. Appl. No. 11/957,208 entitled "Facet arthroplasty devices and methods" filed Dec. 14, 2007.

Reiley et al.; U.S. Appl. No. 11/957,315 entitled "Prostheses, systems and methods for replacement of natural facet joints with artificial facet joint surfaces" filed Dec. 14, 2007.

Reiley, Mark; U.S. Appl. No. 11/957,175 entitled "Facet arthroplasty devices and methods" filed Dec. 14, 2007.

Reiley et al.; U.S. Appl. No. 11/957,290 entitled "Prostheses, systems and methods for replacement of natural facet joints with artificial facet joint surfaces" filed Dec. 14, 2007.

Reiley, Mark; U.S. Appl. No. 11/956,961 entitled "Facet arthroplasty devices and methods" filed Dec. 14, 2007.

Reiley, Mark; U.S. Appl. No. 11/957,149 entitled "Facet arthroplasty devices and methods" filed Dec. 14, 2007.

Reiley, Mark; U.S. Appl. No. 11/957,061 entitled "Facet arthroplasty devices and methods" filed Dec. 14, 2007.

Reiley et al.; U.S. Appl. No. 11/957,259 entitled "Prostheses, systems and methods for replacement of natural facet joints with artificial facet joint surfaces" filed Dec. 14, 2007.

Reiley, Mark; U.S. Appl. No. 12/016,177 entitled "Facet arthroplasty devices and methods" filed Jan. 17, 2008.

Kuiper et al.; U.S. Appl. No. 11/948,994 entitled "Crossbar spinal prosthesis having a modular design and related implantation methods" filed Nov. 30, 2007.

Kuiper et al.; U.S. Appl. No. 11/948,973 entitled "Crossbar spinal prosthesis having a modular design and related implantation methods" filed Nov. 30, 2007.

Kuiper et al.; U.S. Appl. No. 11/957,303 entitled "Crossbar spinal prosthesis having a modular design and related implantation methods" filed Nov. 30, 2007.

McLeer, Thomas; U.S. Appl. No. 11/952,988 entitled "Polymeric joint complex and methods of use" filed Dec. 7, 2007.

Abraham, D.J. et al. "Indications and Trends in Use in Cervical Spinal Fusions." Orthop Clin North Am. Oct. 1998; 29(4):731-44.

Farfan, H.F. Effects of Torsion on the Intervertebral Joints. The Canadian Journal of Surgery, Jul. 1969; 12(3):336-41.

Farfan, H.F. et al. "The Relation of Facet Orientation to Intervertebral Disc Failure." The Canadian Journal of Surgery, Apr. 1967; 10(2):179-85.

Farfan, H.F. The Pathological Anatomy of Degenerative Spondylolisthesis. A Cadaver Study. Spine. Sep.-Oct. 1980; 5(5):412-8.

Fosbinder, R.A. et al. Essentials of Radiologic Science. The McGraw-Hill Companies; 2002.

Goh, J.C. et al. "Influence of PLIF cage size on lumbar spine stability." Spine. Jan. 2000, 25(1) Medline abstract (one page).

Head, W.C."Wagner surface replacement arthroplasty of the hip." Analysis of fourteen failures in forty-one hips. J Bone Joint Surg. Am; Mar. 1981, 63(3), Medline abstract (one page).

Khoo, L.T. et al. "A biomechanical analysis of the effects of lumbar fusion on the adjacent vetebral motion segment." Proceedings of the 2000 Annual Meeting of the North American Spine Society, New Orleans, pp. 127-128.

Kirkaldy-Willis, W.H. et al. "Pathology and Pathogenesis of Lumbar Spondylosis and Stenosis." Spine. Dec. 1978; 3(4):319-28.

Kotani, Y. et al. The effects of spinal fixation and destabilization on the biomechanical and histologic properties of spinal ligaments. An in vivo study. Spine, Mar. 15, 1998, 23(6), Medline abstract (2 pages).

Lam, K. N., et al. X-ray "Diagnosis: A Physician's Approach." Springer-Verlag; 1998.

Lemaire, J.P. et al. "Intervertebral disc prosthesis: results and prospects for the year 2000." Clinical Orthopaedics and Related Research. 1997; No. 337, pp. 64-76.

Lombardi, J.S. et al. "Treatment of Degenerative Spondylolisthesis." Spine. 1985; 10(9): 821-7.

McMillin, C. R. et al. Artificial Spinal Discs with up to Five Years Follow-up. 20th Annual Meeting of the Society for Biomaterials (Abstract) 1994; p. 89.

Nagata, H. et al. "The effects of immobilization of long segments of the spine on the adjacent and distal facet force and lumbrosacral motion". Spine, Dec. 1993; 18(16):2471-2479, (9 pages).

Nibu, K. et al. "Multidirectional stabilizing potential of BAK interbody spinal fusion system for anterior surgery." J Spinal Discord, Aug. 1997; 10(4), Medline abstract (one page).

Posner, I. et al. A "Biomechanical Analysis of the Clinical Stability of the Lumbar and Lumbosacral Spine." Spine. 1982; 7(4): 374-389.

Rosenberg, N.J. "Degenerative Spondylolisthesis. Predisposing Factors." The Journal of Bone and Joint Surgery. 1975; 57-A(4): 467-74.

Slone, R. M. et al. Body CT: A Practical Approach. The McGraw-Hill Companies; 1999.

Stout, G. H. et al. X-Ray Structure Determination: A Practical Guide. 2nd Edition. John Wiley & Sons; 1989.

Szpalski, M., et al. Spine Arthroplasty: A Historical Review. Eur Spine J. 2002; 11(Suppl. 2): S65-S84.

(56) References Cited

OTHER PUBLICATIONS

Tsantrizos, A. et al. "Segmental stability and compressive strength of posterior lumbar interbody fusion implants." Spine, Aug. 1, 2000; 25(15), Medline abstract (one page).

UCR Pedicle Screw System from SeaSpine (information available at http://www.seaspine.com/UCR_Pedicle_Screw_System.html). Accessed Dec. 5, 2005.

Victrex of Lancashire, Great Britain. (information on Victrex available at http://www.matweb.com). Accessed Dec. 5, 2005.

Reiley et al; U.S. Appl. No. 12/058,403 entitled "Polyaxial adjustment of facet joint prostheses," filed Mar. 28, 2008.

Quest et al.; U.S. Appl. No. 12/099,068 entitled "Measurement and trialing system and methods for orthopedic device component selection," filed Apr. 7, 2008.

Reiley, Mark; U.S. Appl. No. 12/176,280 entitled "Facet arthroplasty devices and methods," filed Jul. 18, 2008.

Yuan et al; U.S. Appl. No. 12/163,738 entitled "Prostheses, tools and methods for replacement of natural joints with artificial facet joint surfaces," filed Jun. 27, 2008.

Funk et al; U.S. Appl. No. 12/186,461 entitled "Implantable orthopedic device component selection instrument and methods," filed Aug. 5, 2008.

Eichholz, K.M. et al. "Complications of Revision Spinal Surgery", Neurosurg Focus; (Sep. 15, 2003), 15 (3): pp. 1-4.

Guyer R. et al. "Impliant: Motion Preservation through Total Posterior-Element Replacement." May 7, 2004 Presentation held at Hofburg Center, Vienna, Austria, (2 pages).

Kulkarni, et al. "Accelerated Spondylotic Changes Adjacent to the Fused Segment Following Central Cervical Corpectomy: Magnetic Resonance Imaging Study Evidence." J. Neurosurg (Spine 1). 2004; 100: 2-6.

Sacher, R., Impliant Brochure for presentation at MedTech Insight Conference (Oct. 31, 2003) Boston, MA. pp. 93-94.

* cited by examiner

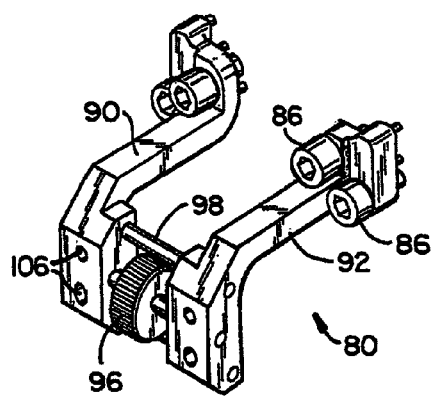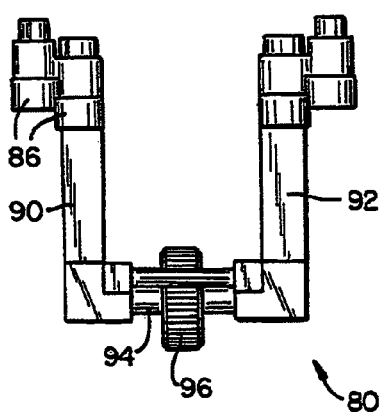
Fig. 8A    Fig. 8B
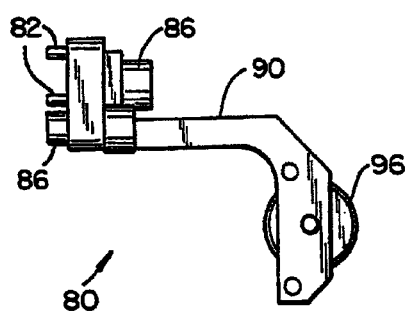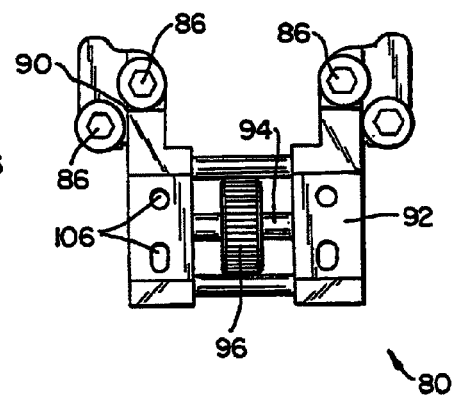
Fig. 8C    Fig. 8D

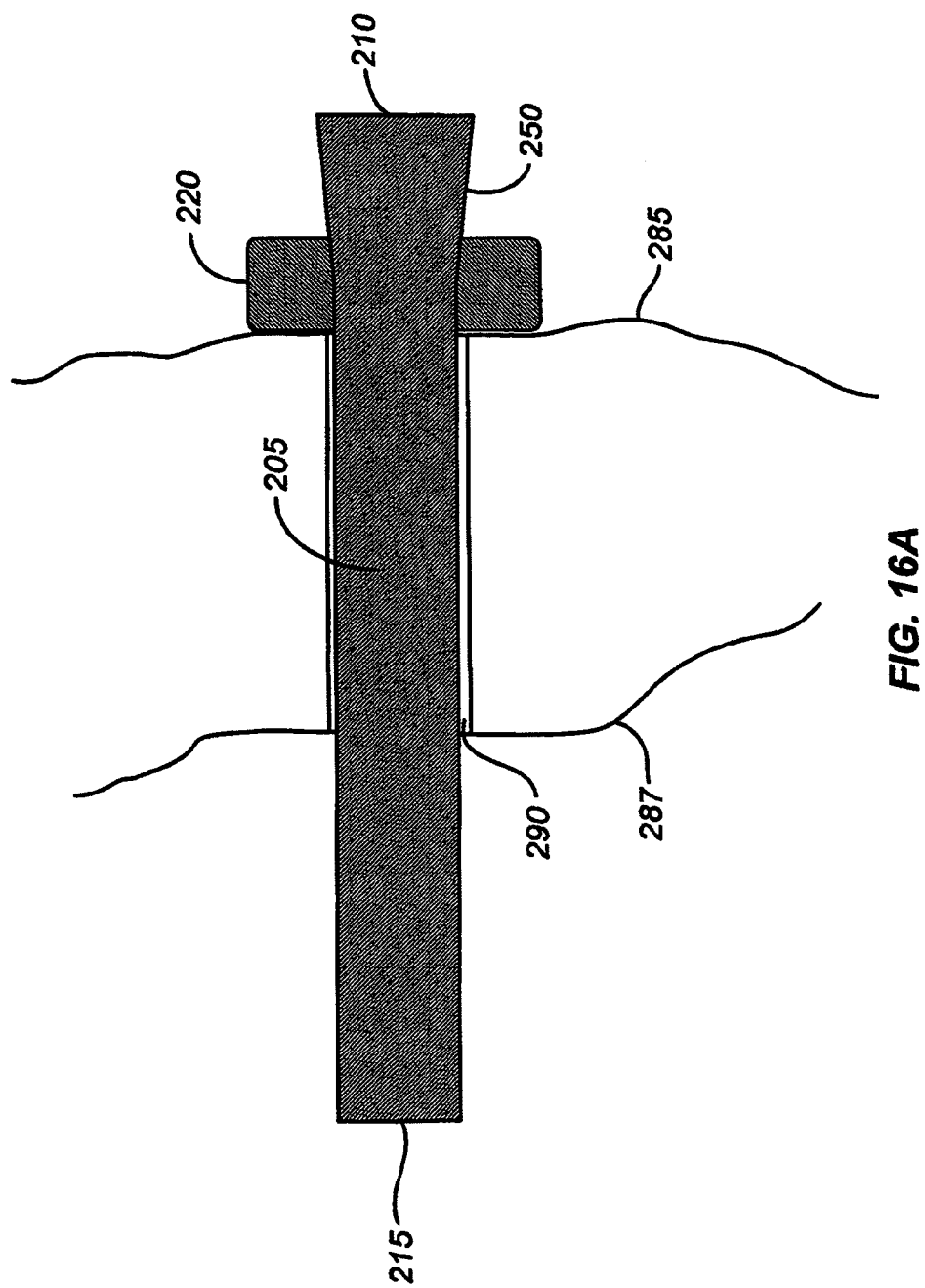

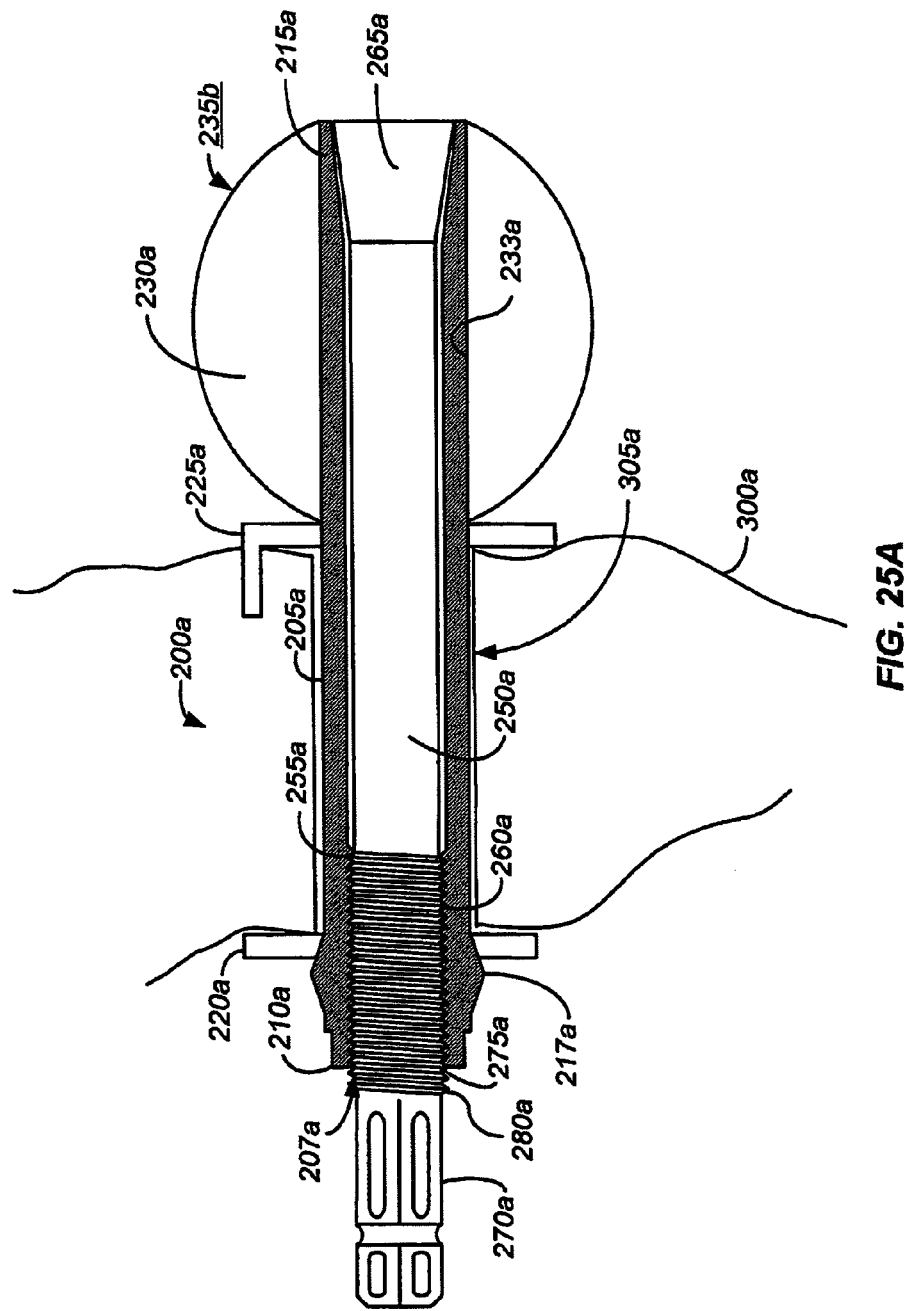

PROSTHESES, TOOLS, AND METHODS FOR REPLACEMENT OF NATURAL FACET JOINTS WITH ARTIFICIAL FACET JOINT SURFACES

CROSS-REFERENCE

This application is a divisional of U.S. patent application Ser. No. 10/973,834, filed Oct. 25, 2004, and entitled "Prosthesis, Tools and Methods for Replacement of Natural Facet Joints with Artificial Facet Joint Surfaces," now U.S. Pat. No. 7,608,104 which is a continuation-in-part of U.S. patent application Ser. No. 10/438,294, filed May 14, 2003, and entitled "Prosthesis, Tools and Methods for Replacement of Natural Facet Joints with Artificial Facet Joint Surfaces," now abandoned and further claims the benefit of Provisional Patent Application Ser. No. 60/567,933, filed May 3, 2004, and entitled "Spinal Prosthesis for Facet Joint Replacement," all of which are incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

BACKGROUND OF THE INVENTION

I. Vertebral Anatomy

As FIG. 1 shows, the human spinal column 10 is comprised of a series of thirty-three stacked vertebrae 12 divided into five regions. The cervical region includes seven vertebrae 12, known as C1-C7. The thoracic region includes twelve vertebrae 12, known as T1-T12. The lumbar region contains five vertebrae 12, known as L1-L5. The sacral region is comprised of five vertebrae 12, known as S1-S5. The coccygeal region contains four vertebrae 12, known as Co1-Co4.

FIG. 2 shows a normal human lumbar vertebra 12. Although the lumbar vertebrae 12 vary somewhat according to location, they share many features common to most vertebrae 12. Each vertebra 12 includes a vertebral body 14 and posterior elements as follows:

Two short extensions/protrusions of bone, the pedicles 16, extend backward from each side of the vertebral body 14 to form a vertebral arch 18. At the posterior end of each pedicle 16 the vertebral arch 18 flares out into broad plates of bone known as the laminae 20. The laminae 20 join to form a spinous process 22. The spinous process 22 serves for muscle and ligamentous attachment. A smooth transition from the pedicles 16 into the laminae 20 is interrupted by the formation of a series of processes.

Two transverse processes 24 thrust out laterally on each side from the junction of the pedicle 16 with the lamina 20. The transverse processes 24 serve as levers for the attachment of muscles to the vertebrae 12. Four articular processes, two superior 26 and two inferior 28, also rise from the junctions of the pedicles 16 and the laminae 20. The superior articular processes 26 are sharp oval plates of bone rising upward on each side from the union of the pedicle 16 with the lamina 20. The inferior processes 28 are oval plates of bone that extend in an inferior direction on each side.

The superior and inferior articular processes 26 and 28 each have a natural bony structure known as a facet. The superior articular facet 30 faces upward or superiorly, while the inferior articular facet 31 faces downward. As FIG. 3 shows, when adjacent (i.e., cephalad and caudal) vertebrae 12 are aligned, the facets 30 and 31, capped with a smooth articular cartilage, interface to form a facet joint 32, also known as a zygapophysial joint.

The facet joint 32 is composed of a superior facet and an inferior facet. The superior facet is formed by the vertebral level below the joint 32, and the inferior facet is formed by the vertebral level above the joint 32. For example, in the L4-L5 facet joint, the superior facet of the joint is formed by bony structure on the L-5 vertebra (e.g., a superior articular surface and supporting bone on the L-5 vertebra), and the inferior facet of the joint is formed by bony structure on the L-4 vertebra (e.g., an inferior articular surface and supporting bone on the L-4 vertebra).

As also shown in FIG. 3, an intervertebral disc 34 between each pair of vertebrae 12 permits relative movement between vertebrae 12. Thus, the structure and alignment of the vertebrae 12 permit a range of movement of the vertebrae 12 relative to each other.

II. Facet Joint Dysfunction

Back pain, particularly in the "small of the back", or lumbosacral (L4-S1) region, is a common ailment. In many cases, the pain severely limits a person's functional ability and quality of life. Such pain can result from a variety of spinal pathologies.

Through disease or injury, the laminae, spinous process, articular processes, or facets of one or more vertebrae can become damaged, such that the vertebrae no longer articulate or properly align with each other. This can result in an undesired anatomy, pain or discomfort, and loss of mobility.

For example, the vertebral facet joints can be damaged by either traumatic injury or by various disease processes. These disease processes include osteoarthritis, ankylosing spondylolysis, and degenerative spondylolisthesis. The damage to the facet joints often results in pressure on nerves, also called a "pinched" nerve, or nerve compression or impingement. The result is pain, neuropathy, misaligned anatomy, and a corresponding loss of mobility. Pressure on nerves can also occur without facet joint pathology, e.g., a herniated disc, due to unwanted bone growth, or as a result of thickening of the soft tissues of the spinal canal, e.g., Arachnoiditis.

One type of conventional treatment of facet joint pathology is spinal stabilization, also known as intervertebral stabilization. Intervertebral stabilization prevents relative motion between the vertebrae. By preventing movement, pain is desirably reduced. Stabilization can be accomplished by various methods.

One method of stabilization is posterior spinal fusion. Another method of stabilization is anterior spinal fusion, fixation of any number of vertebrae to stabilize and prevent movement of the vertebrae.

Another type of conventional treatment is decompressive laminectomy. This procedure involves excision of the laminae to relieve compression of nerves.

These traditional treatments are subject to a variety of limitations and varying success rates. Furthermore, none of the described treatments puts the spine in proper alignment or return the spine to a desired anatomy. In addition, stabilization techniques, by holding the vertebrae in a fixed position, permanently limit the relative motion of the vertebrae, altering spine biomechanics.

FIELD OF THE INVENTION

This invention relates to prostheses for treating various types of spinal pathologies, as well as to methods of treating spinal pathologies.

SUMMARY OF THE INVENTION

There is a need for prostheses, installation tools, and methods that overcome the problems and disadvantages associated with current strategies and designs in various treatments for spine pathologies.

The invention provides prostheses, installation tools, and methods designed to replace natural facet joints at virtually all spinal levels including L1-L2, L2-L3, L3-L4, L4-L5, L5-S1, T11-T12, and T12-L1. The prostheses, installation tools, and methods can restore a desired anatomy to a spine and give back to an individual a desired range of relative vertebral motion. The prostheses, installation tools, and methods also can lessen or alleviate spinal pain by relieving the source of nerve compression or impingement, restoring spinal alignment and/or allowing for partial and/or total immobilization and/or fusion of treated levels.

For the sake of description, the prostheses that embody features of the invention will be called either "cephalad" or "caudal" with relation to the portion of a given natural facet joint they replace. As previously described, a given natural facet joint has a superior facet and an inferior facet. In anatomical terms, the superior facet of the joint is formed by the vertebral level below the joint (which can thus be called the caudal portion of the facet joint, i.e., because it is nearer the feet). The inferior facet of the joint is formed by the vertebral level above the joint (which can thus be called the cephalad portion of the facet joint, i.e., because it is nearer the head). Thus, a prosthesis that, in use, replaces the caudal portion of a facet joint (i.e., the superior facet of the caudal vertebral body) will be called a "caudal" prosthesis. Likewise, a prosthesis that, in use, replaces the cephalad portion of a facet joint (i.e., the inferior facet of the cephalad vertebral body) will be called a "cephalad" prosthesis.

One aspect of the invention provides a cephalad facet joint prosthesis to replace a cephalad portion of a natural facet joint (e.g., an inferior articular surface and its supporting bone structure on the posterior elements of the vertebra) in the posterior elements of a vertebra. According to this aspect of the invention, the prosthesis includes an artificial facet joint element adapted and configured to replace a cephalad portion of the natural facet joint and a fixation element extending from the artificial facet joint element, the fixation element being adapted and configured to be inserted through a lamina portion of a vertebra to affix the artificial facet joint element to the vertebra, preferably without blocking access to a pedicle portion of the vertebra. The fixation element may also extend into and/or through a second lamina portion of the vertebra, such as by traversing the midline of the vertebra through or adjacent to the spinous process. In one embodiment, after installation the cephalad bearing element is disposed between a caudal facet joint bearing surface and a portion of the vertebra, such as a lamina portion.

This aspect of the invention also provides a method of implanting an artificial cephalad facet joint prosthesis on a vertebra and/or the posterior elements of a vertebra. According to this method, a fixation element is inserted through a lamina portion of the vertebra, and a cephalad facet joint bearing surface is placed in a position to form a cephalad portion of a facet joint. An artificial facet joint element is attached to a distal end of the fixation element either after or prior to insertion of the fixation element. The fixation element preferably does not block anterior, posterior and/or lateral access to a pedicle portion of the vertebra. The fixation element may also extend through a second lamina portion of the vertebra, such as by traversing the midline of the vertebra through or adjacent to the spinous process. In one embodiment, the placing step includes disposing the artificial facet joint bearing surface between a caudal facet joint bearing surface and a portion of the vertebra, such as a lamina portion. The method may also include the steps of using a guide to define an insertion path for the fixation element, forming a passage through the lamina corresponding to the insertion path, and/or prepping the surface of the treated vertebral levels to accept the cephalad and/or caudal components.

Another aspect of the invention provides a prosthesis to replace a cephalad portion of a natural facet joint on a vertebra. In this aspect of the invention the prosthesis includes an artificial facet joint element adapted and configured to replace a cephalad portion of the natural facet joint; and a fixation element adapted and configured to affix the artificial facet joint element to the vertebra without blocking access to a pedicle portion of the vertebra. In one embodiment, after installation the cephalad bearing element is disposed between a caudal facet joint bearing surface (either the natural caudal joint surface or an artificial caudal joint surface) and a portion of the vertebra, such as a lamina portion.

This aspect of the invention also provides a method for implanting a cephalad facet joint prosthesis to replace a removed cephalad portion of a natural facet joint on a vertebra. The method includes the steps of aligning the cephalad facet joint prosthesis with a caudal facet joint bearing surface; and attaching the cephalad facet joint prosthesis to the vertebra without blocking a pedicle portion of the vertebra. The attaching step of the method may also include disposing the cephalad facet joint prosthesis between the caudal facet joint bearing surface and a portion of the vertebra. The attaching step may also include the step of inserting a fixation element through a portion of the vertebra, such as the lamina. In this case, the method may include the steps of defining an insertion path in the vertebra prior to the inserting step and forming a passage in the vertebra corresponding to the insertion path. A guide may be used to direct the location and orientation of the insertion path.

Another aspect of the invention provides a facet joint prosthesis to replace, on a vertebra, a caudal portion of a natural facet joint (e.g., a superior articular surface and supporting bone structure on the vertebra). The prosthesis includes an artificial facet joint element with a vertebra contacting surface and a caudal bearing surface, the caudal bearing surface being adapted and configured to replace a caudal portion of a natural facet joint and, in various embodiments, to be substantially entirely posterior of a contact portion of the vertebra when the vertebra contacting surface contacts the contact portion. The prosthesis also includes a fixation element extending from the artificial facet joint element, the fixation element being adapted and configured to be inserted into the vertebra to affix the prosthesis to the vertebra.

Another aspect of the invention provides a prosthesis for replacing a cephalad portion and a caudal portion of a natural facet joint of cephalad and caudal vertebrae of a spine motion segment. The prosthesis includes an artificial cephalad facet joint element adapted and configured to replace a cephalad portion of the natural facet joint, the artificial cephalad facet joint element having a cephalad bearing surface; a cephalad fixation element, the cephalad fixation element being adapted and configured to be inserted through a lamina portion of a vertebra to affix the artificial cephalad facet joint element to the cephalad vertebra; and an artificial caudal facet joint element adapted and configured to replace a caudal portion of the natural facet joint, the artificial caudal facet joint element including a caudal bearing surface adapted and configured to mate with the cephalad bearing surface.

Yet another aspect of the invention provides a method for implanting a facet joint prosthesis to replace removed cephalad and caudal portions of a natural facet joint of cephalad and caudal vertebrae. The method includes the steps of: affixing an artificial caudal facet joint element to the caudal vertebra; inserting a cephalad fixation element through a lamina portion of the cephalad vertebra; and placing an artificial cephalad facet joint bearing surface in a position to form a cephalad portion of a facet joint. The method may also include attaching an artificial cephalad facet joint element comprising the cephalad facet joint bearing surface to an end of the fixation element either prior to or after the inserting step. The method may also include removal of various bone structures (such as one or more facet structures and/or laminar material) and/or prepping of the bone surfaces. In at least one embodiment, the fixation element does not block access to a pedicle portion of the cephalad vertebra. The cephalad fixation element may also extend through a second lamina portion of the cephalad vertebra, such as by traversing the midline of the cephalad vertebra through or adjacent to the spinous process. The placing step may also include the step of disposing the artificial cephalad facet joint bearing surface between the artificial caudal facet joint element and a portion of the cephalad vertebra. An installation fixture may be used to align the caudal and cephalad elements, although the prosthesis may also be installed without using an installation fixture. The method may also include the step of using a guide to define an insertion path for the cephalad fixation element, although the prosthesis may also be installed without using a guide.

Another aspect of the invention provides a prosthesis to replace cephalad and caudal portions of a natural facet joint of cephalad and caudal vertebrae. The prosthesis may include an artificial cephalad facet joint element adapted and configured to replace a cephalad portion of the natural facet joint, with the artificial cephalad facet joint element including a cephalad bearing surface; a cephalad fixation element adapted and configured to affix the artificial cephalad facet joint element to the cephalad vertebra without blocking access to a pedicle portion of the cephalad vertebra; and an artificial caudal facet joint element adapted and configured to replace a caudal portion of the natural facet joint, the artificial caudal facet joint element including a caudal bearing surface adapted and configured to mate with the cephalad bearing surface. In one embodiment, after installation the cephalad facet joint bearing surface is disposed between a caudal facet joint bearing surface and a portion of the vertebra, such as a lamina portion. In one embodiment, the cephalad bearing surface and the caudal bearing surface each has a width along its respective transverse axis, with the cephalad bearing surface width being shorter than the caudal bearing surface width. The artificial caudal facet joint element may also include a vertebra contacting surface, with the entire caudal bearing surface being adapted and configured to be posterior of a contact portion of the caudal vertebra when the vertebra contacting surface contacts the contact portion.

This aspect of the invention also includes a method for implanting a facet joint prosthesis to replace removed cephalad and caudal portions of a natural facet joint of cephalad and caudal vertebrae. The method includes the steps of affixing an artificial caudal facet joint element to the caudal vertebra; and affixing an artificial cephalad facet joint element to the cephalad vertebra in alignment with the artificial caudal facet joint element and without blocking access to a pedicle portion of the cephalad vertebra. The second affixing step may also include the step of disposing the artificial cephalad facet joint element between the artificial caudal facet joint element and a portion of the cephalad vertebra. An installation fixture may be used to align the caudal and cephalad element, although the prosthesis may also be installed without using an installation fixture. The method may also include the step of using a guide to define an insertion path for the cephalad fixation element, although the prosthesis may also be installed without using a guide.

Another aspect of the invention includes devices and methods that minimize the size and extent of the surgical incision (s) required during the repair and/or replacement of facet joints. For example, one disclosed embodiment of a prosthesis for replacing a cephalad facet joint can potentially be implanted into a targeted vertebral body through a minimally-invasive cannula. This embodiment can be utilized in conjunction with a surgical incision with exposes only the posterior portion of the targeted facet joint to be replaced. (Alternatively, this embodiment can be utilized in conjunction with an endoscopic expanding cannula, such as the Atavi Flexposure® Retractor, commercially available from Endius Incorporated of Plainville, Mass.) Desirably, the surgical site is prepared—including removal of cephalad/caudal facet material and/or decompression of affected nerve fibers—and the cephalad and caudal prosthesis attached and positioned with little or no disruption to surrounding tissues, including the supra-spinous and/or inter-spinous ligaments.

In another disclosed embodiment of the present invention, the caudal component of a facet prosthesis can be secured to the lamina of the inferior vertebral body, while the cephalad component is secured to one or more pedicles of the superior vertebral body. This configuration facilitates the secure placement of a facet prosthesis where some or all of the lamina and/or posterior structures of the superior vertebral body have been removed and/or damaged as a result of injury, disease and/or surgical intervention.

In another disclosed embodiment of the present invention, both the cephalad and caudal components of a facet prosthesis can be secured to the lamina of their respective vertebral bodies.

In another aspect of the present invention, there is provided a method for implanting a spinal prosthesis by forming a passage from a first side of a lamina or a spinous process completely through to a second side of the lamina or the spinous process; advancing a distal end of a fastening element from the first side to the second side until a proximal stop of the fastening element rests against the first side; and securing a bearing prosthesis to the distal end of the fastening element. In additional embodiments, the forming step and the advancing step are performed percutaneously and/or the securing step is performed percutaneously. In another alternative, the securing step is performed by placing an element between the bearing and the fastening element. In yet another alternative, the securing step is performed by expanding the fastening element into an opening in the bearing prosthesis. In another alternative, a reinforcing structure or material is provided to distribute forces applied to the first side and/or the second side.

In another aspect of the present invention, there is provided a spinal prosthesis having an elongate body having a distal end and a flared proximal end; a proximal collar adapted to pass over the distal end and to fit against the flared proximal end; and a prosthetic bearing element forming a part of an articulating process of the spine, the bearing element having an outer surface and an internal opening adapted to fit over the elongate body distal end. In another alternative embodiment, the elongate body is long enough to pass completely through a lamina or a spinous process. In another embodiment, the elongate body and the proximal collar are adapted to be percutaneously implanted into a portion of the spine. In yet another embodiment, the prosthetic bearing element is adapted to be percutaneously implanted into a portion of the spine. In another embodiment there is also provided a distal collar adapted to fit over the elongate body distal end proximal to the prosthetic bearing element. In an alternative embodiment, the elongate body has a non-circular cross section. In yet another embodiment, a portion of the outer surface of the elongate body is covered with a bone in-growth compound.

In another embodiment of the present invention, there is provided a spinal prosthesis having an elongate body having a distal end and proximal end; a prosthetic bearing element adapted to form a part of an articulating process in the spine, the bearing element having an outer surface and an internal opening adapted to fit over the elongate body distal end; and a shaft having a proximal end and a flared distal end is disposed within the elongate body such that when the shaft advances within the elongate body an outer surface of the elongate body is pressed against a portion of the prosthetic bearing internal opening. In another alternative embodiment, the shaft is threaded to engage with a threaded internal portion of the elongate body. In another embodiment, the distal ends of the shaft and the elongate body are adapted to engage with a drive instrument, fixing the elongate body while allowing rotation of the shaft. In another embodiment, the shaft proximal end further comprises a shearable drive section proximal to a drive section. In yet another embodiment, the elongate body further comprising a feature formed on the elongate body outer surface adapted to engage a proximal collar.

Other features and advantages of the inventions are set forth in the following Description and Drawings, as well as in the appended Claims.

BRIEF DESCRIPTION OF THE DRAWINGS

FIG. 8A is a perspective view of an installation fixture according to one embodiment of this invention.

FIG. 8B is a top view of the installation fixture of FIG. 8A.

FIG. 8C is a side view of the installation fixture of FIG. 8A.

FIG. 8D is a back view of the installation fixture of FIG. 8A.

FIGS. 16A-16D illustrate a method of implanting and securing the prosthesis of FIGS. 15A and 15B.

FIG. 25A is a cross section view of the cephalad prosthesis of FIG. 25 with an alternative embodiment of a bearing surface element.

Figure 1:
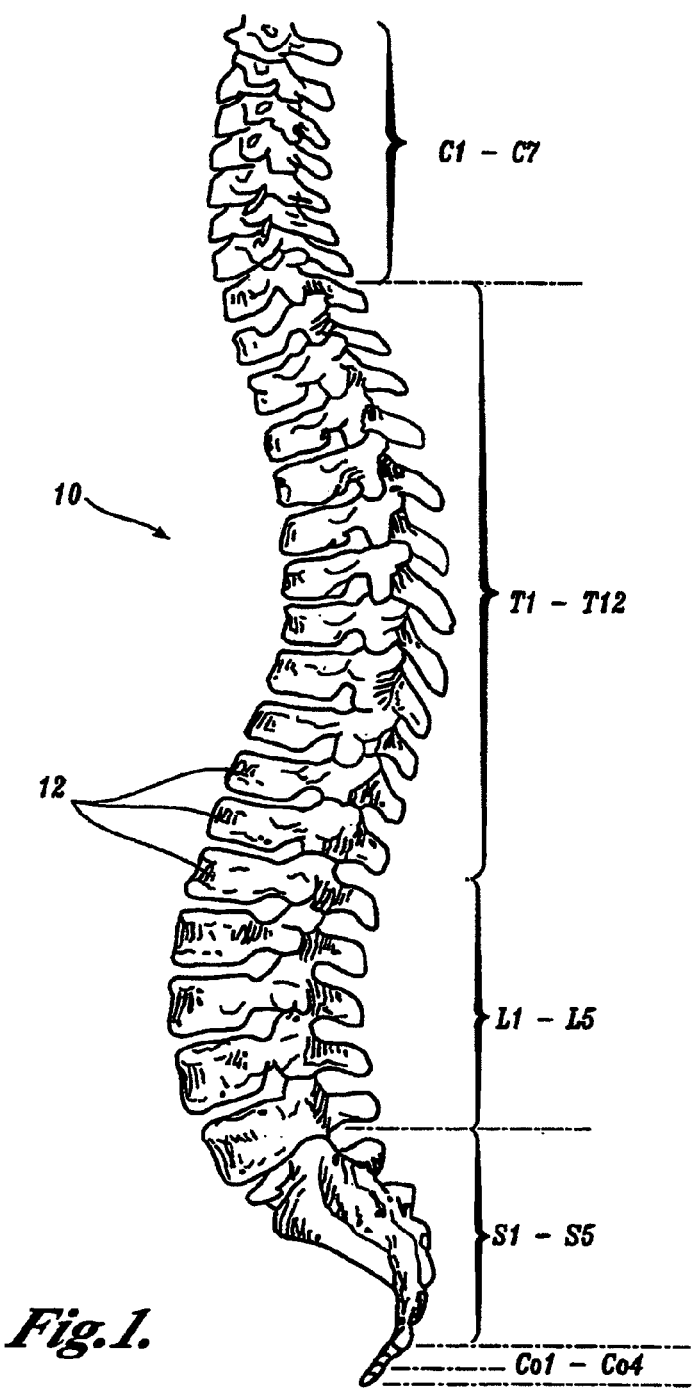
FIG. 1 is a lateral elevation view of a normal human spinal column.
Figure 2:
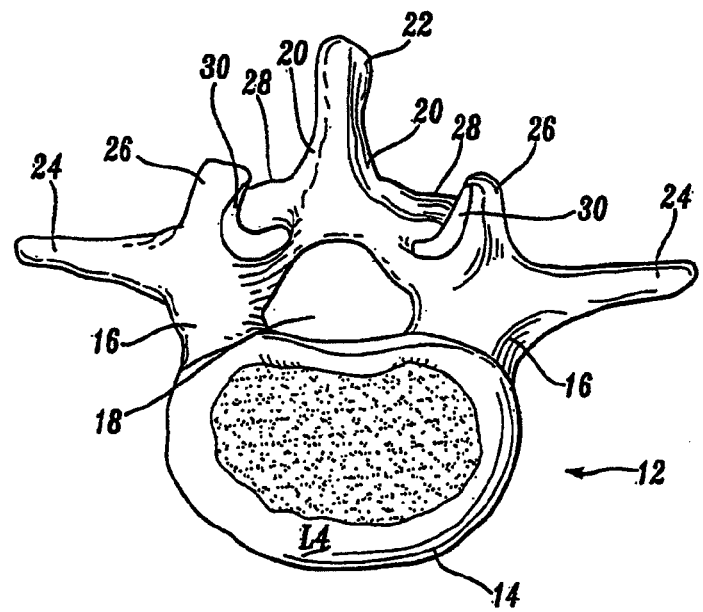
FIG. 2 is a superior view of a normal human lumbar vertebra.
Figure 3:
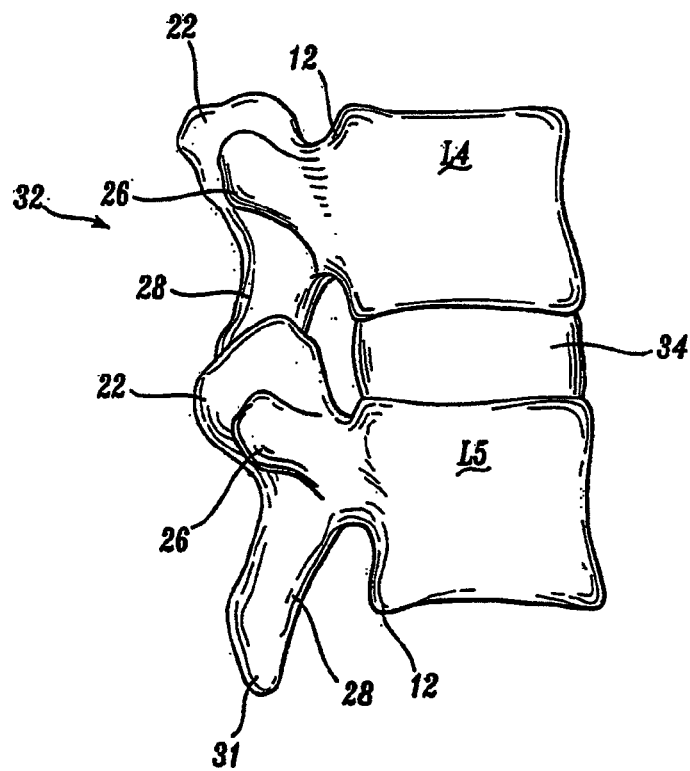
FIG. 3 is a lateral elevation view of a vertebral lumbar facet joint.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DETAILED DESCRIPTION OF THE INVENTION

Although the disclosure hereof is detailed and exact to enable those skilled in the art to practice the invention, the physical embodiments herein disclosed merely exemplify the invention that may be embodied in other specific structure. While the preferred embodiment has been described, the details may be changed without departing from the invention, which is defined by the claims.

FIGS. 4-7 show artificial cephalad and caudal facet joint prostheses 36 and 50 (see FIG. 7C) for replacing a natural facet joint according to one aspect of this invention. Cephalad prosthesis 36 has a bearing element 38 with a bearing surface 40. In this embodiment, bearing surface 40 has a convex shape. Bearing element 38 may be formed from biocompatible metals (such as cobalt chromium steel, surgical steels, titanium, titanium alloys, tantalum, tantalum alloys, aluminum, etc.), ceramics, polyethylene, biocompatible polymers, and other materials known in the prosthetic arts, and bearing surface 40 may be formed from biocompatible metals (such as cobalt chromium steel, surgical steels, titanium, titanium alloys, tantalum, tantalum alloys, aluminum, etc.), ceramics, polyethylene, biocompatible polymers, and other materials known in the prosthetic arts.

Depending on the patient's disease state, the condition of the patient's natural facet joint—including the facet joint's strength, location and orientation—may not be acceptable and/or may need to be removed to access other spinal structures (such as the lamina and/or an intervertebral disc). As shown in FIGS. 4-7, therefore, the natural cephalad and caudal facet joint surfaces have been removed to enable the installation of a prosthetic facet joint without limitations presented by remaining portions of the natural facet joint.

In one embodiment of the invention, fixation element 42 attaches cephalad prosthesis 36 to a vertebra 60 in an orientation and position that places bearing surface 40 in approximately the same location as the natural facet joint surface the prosthesis replaces. The prosthesis may also be placed in a location other than the natural facet joint location without departing from the invention, such as by orienting the fixation element along a different angle, by moving the joint cephalad/caudad, anteriorly/posteriorly, by moving the joint medially or laterally, or any combination thereof.

In the embodiment shown in FIGS. 4-7, fixation element 42 is a screw. Other possible fixation elements include headless screws, stems, posts, corkscrews, wire, staples, adhesives, bone cements, and other materials known in the prosthetic arts.

In this embodiment of the invention, the cephalad facet joint prosthesis attaches to a posterior element of the vertebra, such as one or more portions of the lamina and/or the spinous process. For example, as shown in FIGS. 4-7, fixation element 42 may extend through a lamina portion 62 of vertebra 60 at the base of spinous process 64, traversing the vertebra midline as defined by the spinous process 64 and through another lamina portion 66. This orientation of the fixation element is similar to the orientation used to accomplish translaminar facet joint screw fixation, as known in the art. Other orientations of fixation element 42 are possible, of course, depending on the dictates of the specific vertebral anatomy and the desires of the clinician. For example, fixation element 42 may extend through only one lamina portion, only through the spinous process, etc.

Unlike other facet joint prostheses that attach to the pedicle, this embodiment's use of one or more posterior elements of the vertebra to attach the cephalad facet joint prosthesis of this invention does not block access to the pedicle area, leaving this area free to be used to attach other prostheses or devices. Other embodiments of the invention may occupy, block or impede access to the pedicle area, of course, without departing from the scope or spirit of the invention. In addition, because of the inherent strength of the lamina (and the surrounding cortical bone), the cephalad facet joint prosthesis may be affixed without the use of bone cement, especially when using a bone ingrowth surface, trabecular/coated metal or bioactive ceramics.

Figure 4:
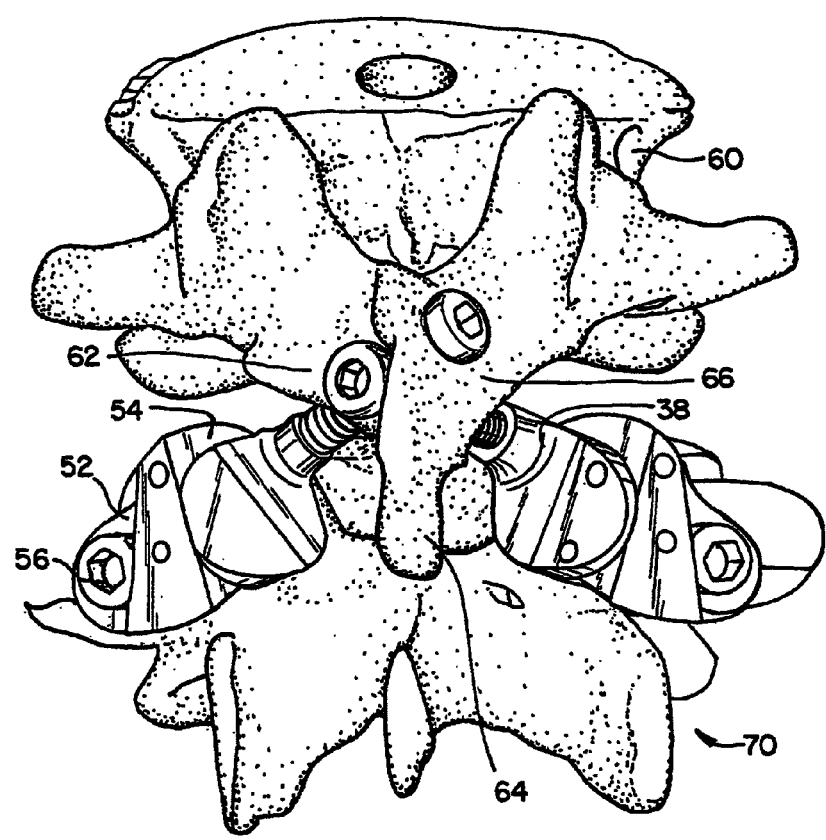
FIG. 4 is a posterior view of an artificial facet joint prosthesis installed in a patient according to one embodiment of this invention.
Figure 5:
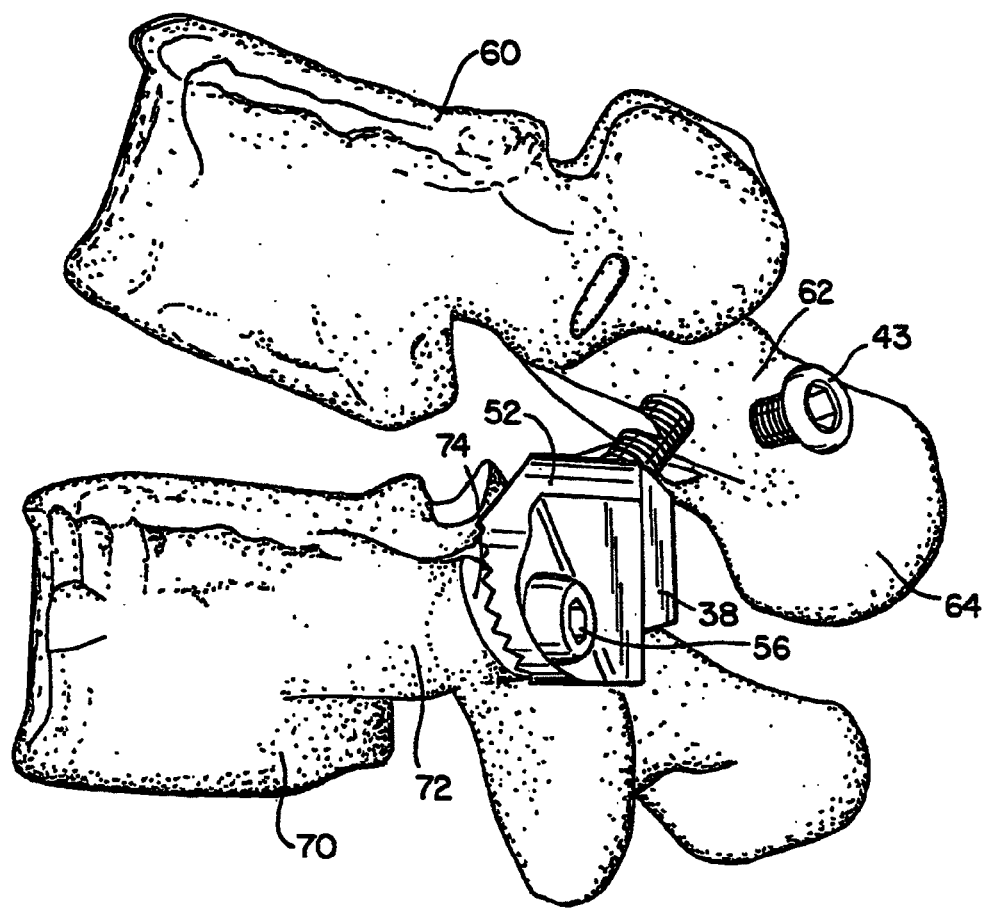
FIG. 5 is a left side view of the embodiment of FIG. 4, as installed in a patient.
Figure 6:
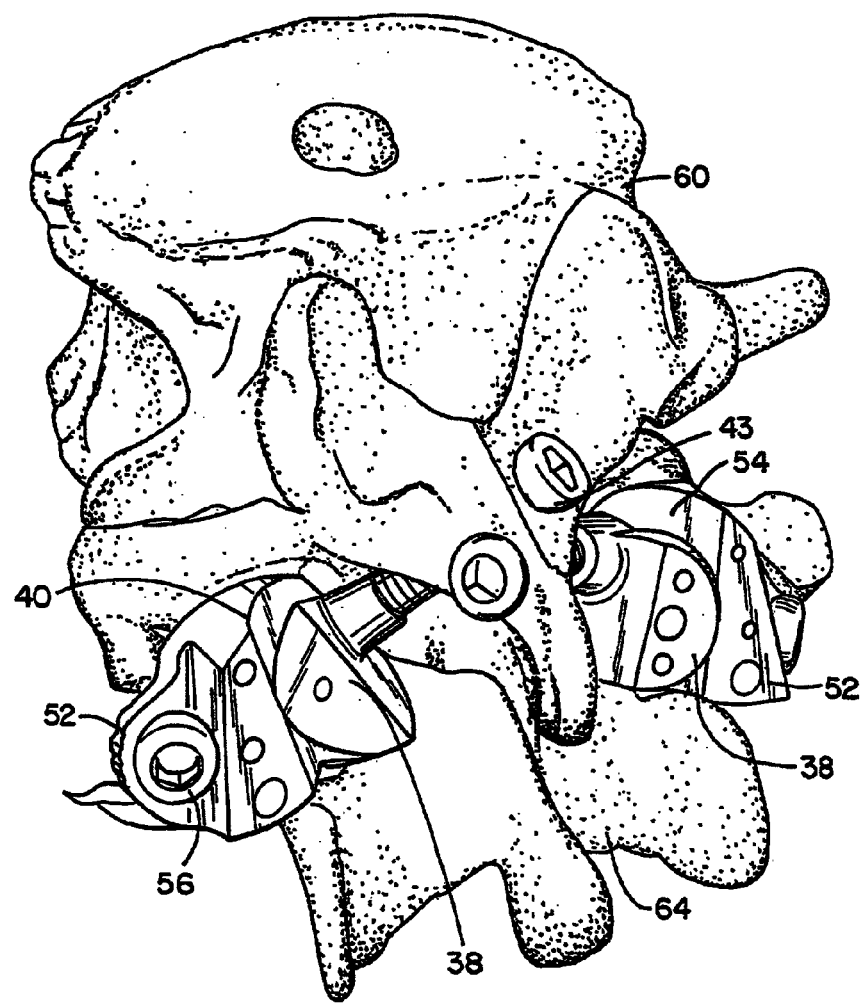
FIG. 6 is yet another view of the embodiment of FIG. 4, as installed in a patient.
Figure 7A:
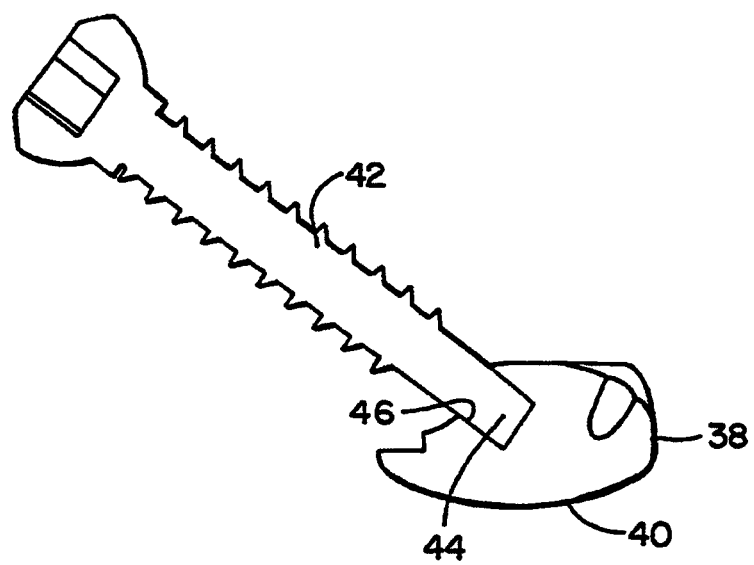
FIG. 7A is a cross-sectional view of a cephalad bearing element and fixation element according to the embodiment of FIG. 4.
Figure 7B:
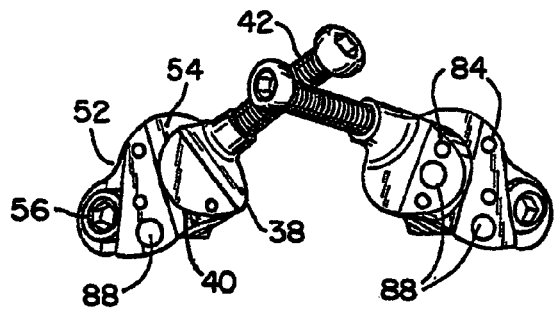
FIG. 7B is a posterior view of a pair of artificial cephalad and caudal facet joint prostheses according to one embodiment of this invention.
Figure 7C:
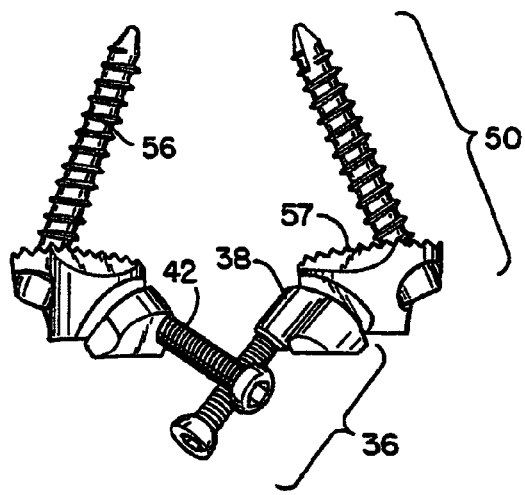
FIG. 7C is a top view of a pair of artificial cephalad and caudal facet joint prostheses in the embodiment of FIG. 7A.
Figure 7D:
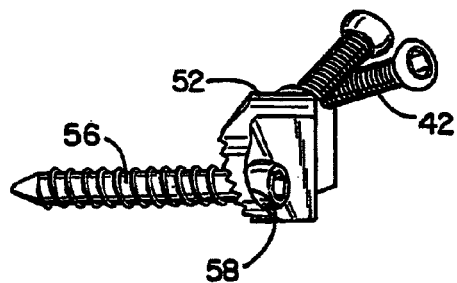
FIG. 7D is a left view of a pair of artificial cephalad and caudal facet joint prostheses in the embodiment of FIG. 7A.
Figure 7E:
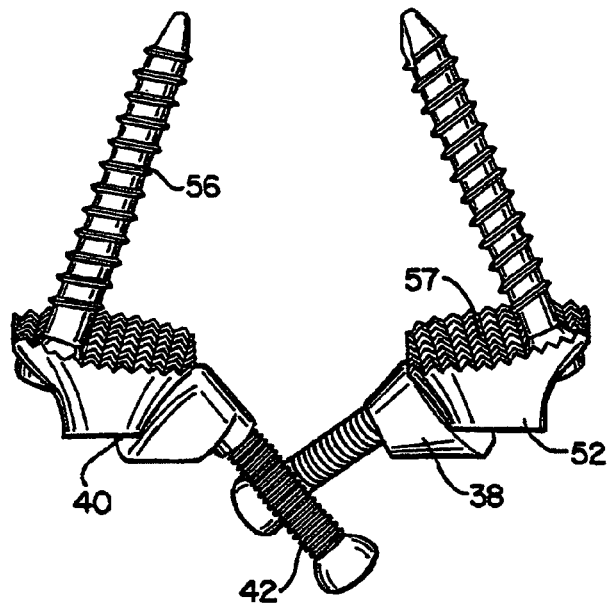
FIG. 7E is a bottom view of a pair of artificial cephalad and caudal facet joint prostheses in the embodiment of FIG. 7A.
Figure 7F:
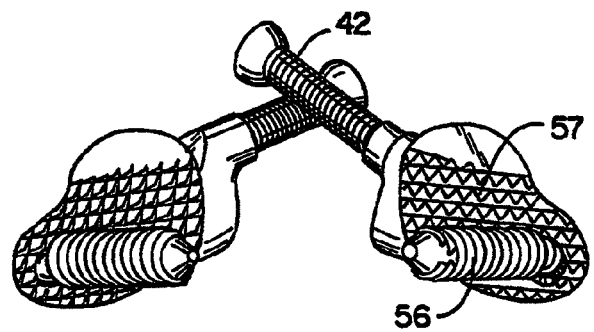
FIG. 7F is an anterior view of a pair of artificial cephalad and caudal facet joint prostheses in the embodiment of FIG. 7A.
Figure 7G:
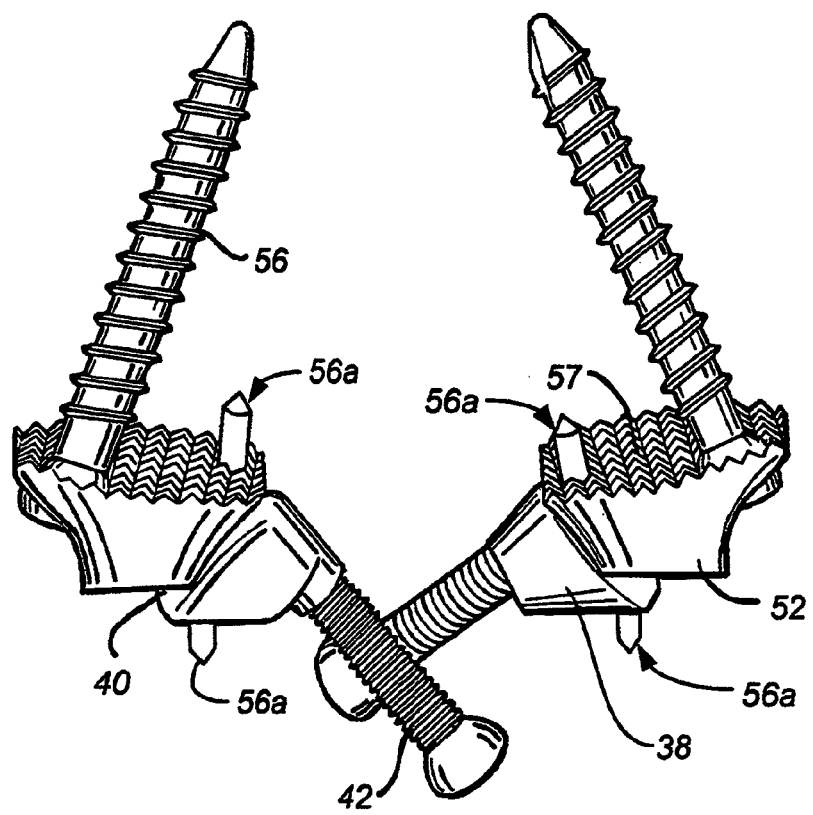
FIG. 7G is a bottom view of an alternate embodiment of a pair of artificial cephalad and caudal facet joint prostheses.

In the orientation shown in FIGS. 4-6 as well as in some alternative embodiments, after insertion the fixation element's proximal end 43 (preferably formed to mate with a suitable insertion tool) and distal end 44 lie on opposite sides of the lamina. Bearing element 38 attaches to the distal end 44 of fixation element 42 to be disposed between a caudal facet joint bearing surface (either natural or artificial, such as the artificial caudal facet joint prosthesis described below) and a portion of the vertebra, such as the lamina portion shown in FIGS. 4-6. To attach bearing element 38 to fixation element 42 in the embodiment shown in FIG. 4, a hole 46 in bearing element 38 is formed with a Morse taper that mates with the distal end 44 of fixation element 42. Other means of attaching bearing element 38 to fixation element 42 may be used, of course, such as other Morse or other taper connections, machine screw threads, NPT screw threads or other known mechanical, physical (welding, etc.) or chemical fastening means. Fixation element 42 may be coated with antimicrobial, antithrombotic, hydroxyapatite, osteoinductive and/or osteoconductive materials to promote bone ingrowth and fixation. Bearing element 38 may be attached to fixation element 42 before or after implantation in the patient, depending on the manner of implantation and the requirements of the situation.

Prosthesis 36 may be used to form the cephalad portion of a facet joint with either a natural caudal facet joint portion or an artificial caudal facet joint prosthesis.

FIGS. 4-7 also show an artificial caudal joint prosthesis 50 for replacing the superior half of a natural facet joint according to one aspect of this invention. Caudal prosthesis 50 has a bearing element 52 with a bearing surface 54. In this embodiment, bearing surface 54 is concave (although the surface could be a myriad of shapes, including, but not limited to, convex, rounded, flattened, complex, and/or spherical bearing surfaces). Bearing element 52 may be formed from biocompatible metals (such as cobalt chromium steel, surgical steels, titanium, titanium alloys, tantalum, tantalum alloys, aluminum, etc.), ceramics, polyethylene, biocompatible polymers, and other materials known in the prosthetic arts, and bearing surface 54 may be formed from biocompatible metals (such as cobalt chromium steel, surgical steels, titanium, titanium alloys, tantalum, tantalum alloys, aluminum, etc.), ceramics, polyethylene, biocompatible polymers, and other materials known in the prosthetic arts.

In one embodiment, the natural caudal facet surface has been removed, and fixation element 56 attaches prosthesis 50 to a vertebra 70 via a pedicle in an orientation and position that places bearing surface 54 in approximately the same location as the natural facet joint surface the prosthesis replaces. In an alternative embodiment, the bearing surface 54 may be placed in a location different than the natural facet joint surface, either more medial or more lateral, more cephalad or more caudad, more anterior or more posterior, and/or rotated or displaced from the natural anatomical orientation and orientation. For example, the geometry and function of the artificial joints could be designed to allow for greater-than-natural flexibility and/or movement, to account for motion missing and/or lost due to disease, injury, aging and/or fusion of the treated and/or other vertebral levels. In addition, in other embodiments the caudal component can be attached to other locations in or on the vertebral body in addition to the pedicle or to the vertebral body alone.

As shown in the embodiment of FIGS. 4-7, fixation element 56 is a screw attached to bearing element 54 via a hole 58 formed in bearing element 52 and is inserted into a pedicle portion 72 of vertebra 70. Other possible fixation elements include stems, posts, corkscrews, wire, staples, adhesives, clamps, hooks, bone cements, and other materials known in the prosthetic arts. The fixation element 56 can also be inserted into the vertebral body (or portions of the lamina or spinous process) in addition to or in place of the pedicle. The fixation element may comprise some or all of the bearing surface.

In this embodiment, bearing element 52 has a serrated fixation surface 57 adapted to contact a contact portion 74 of vertebra 70. This optional fixation surface 57 helps prevent rotation of the bearing element 52. In various embodiments, the fixation surface 57 may be coated with bone ingrowth material, and any optional serrations can increase the surface area for bony ingrowth (as well as prevent unwanted rotation of the implant). As shown in FIG. 5, in this embodiment the entire bearing surface 54 is posterior to surface 57 and contact portion 74. Alternatively, the bearing elements 52 and 38 could incorporate an off-center peg or protrusion 56a (See FIG. 7G) which fits into a corresponding hole or opening (not shown) in the pedicle and/or laminae to inhibit and/or prevent undesired rotation of the element 52. In another alternate embodiment, the cephalad and/or caudal components could include an auxiliary fastener or clip (not shown) which secures to or around a portion of the vertebral body to inhibit and/or prevent rotation and/or displacement of the caudal or cephalad component. In an alternate embodiment, one or more of the bearing elements could comprise an artificial or natural (i.e., allograft, autograft, xenograft or other bone graft material) substance used to resurface the natural and/or degenerated facet surface.

Prosthesis 50 may be used to form the caudal portion of a facet joint with either a natural cephalad facet joint portion or an artificial cephalad facet joint prosthesis. Similarly, an artificial cephalad facet joint portion may be use in conjunction with either an natural or artificial caudal facet joint component.

FIGS. 7A-F show an artificial facet joint prosthesis according to one embodiment of this invention apart from the vertebrae. As shown, cephalad bearing surface 40 and caudal bearing surface 54 meet to form an artificial facet joint. As seen best in FIG. 7B, the width of caudal bearing surface 54 along its transverse axis is desirably greater than the width of cephalad bearing surface 40 along its transverse axis. This feature helps align the cephalad and caudal joints during implant. In addition, this feature permits the point of contact between the two bearing surface to change with flexion, extension, left and right rotation and lateral bending of the patient's spine. If desired, the prosthesis can be designed to mimic the natural motion and flexibility of the replaced facet joint, or can alternatively be tailored to accommodate a lesser or greater degree of flexibility and/or motion (to accommodate damaged tissues such as discs, etc., or to compensate for co-existing limitations on spinal motion such as existing spinal deformities and/or adjacent fused levels).

The prostheses of FIGS. 4-7 may be implanted without special tools. One embodiment of the invention, however, includes an installation fixture to assist with the implantation procedure. FIGS. 8-14 show installation tools used to implant two artificial facet joints, i.e., two cephalad facet joint prostheses and two corresponding caudal facet joint prostheses. The invention also includes installation tools for implanting a single facet joint prosthesis, two caudal facet joint prostheses, two cephalad facet joint prostheses, a caudal and cephalad joint prosthesis, or any other combination of facet joint prostheses.

Figure 9:
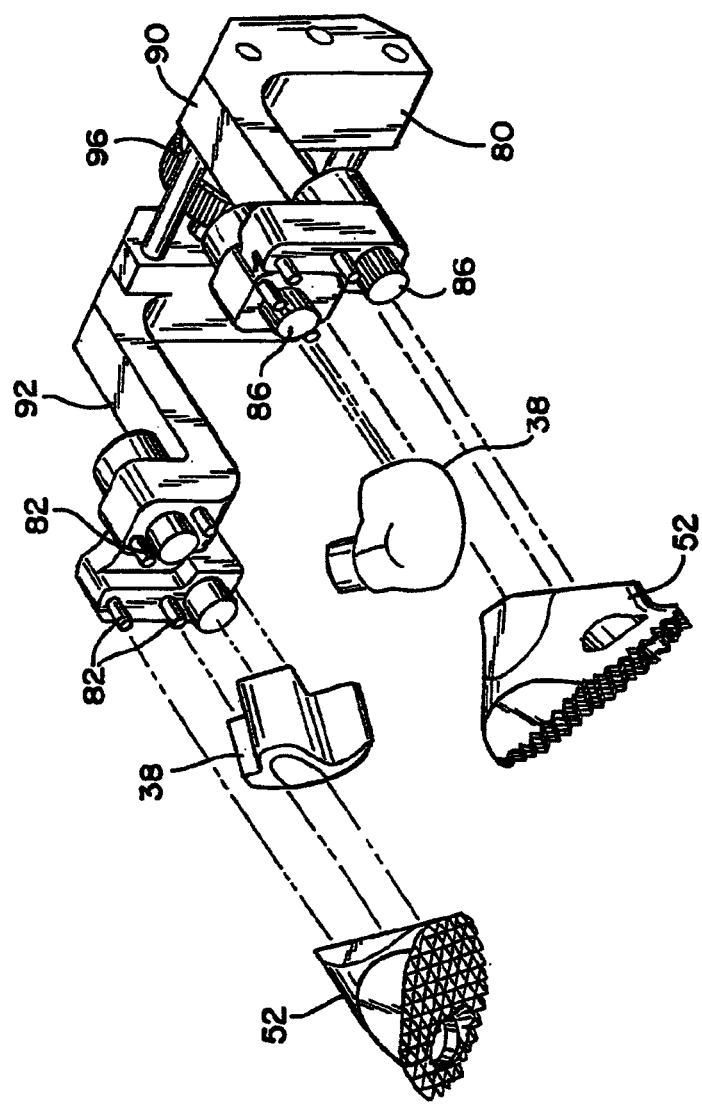
FIG. 9 is an exploded view of the installation fixture of FIG. 8 along with a pair of caudal facet bearing elements and a pair of cephalad facet bearing elements according to one embodiment of the invention.
Figures 10A, 10B:
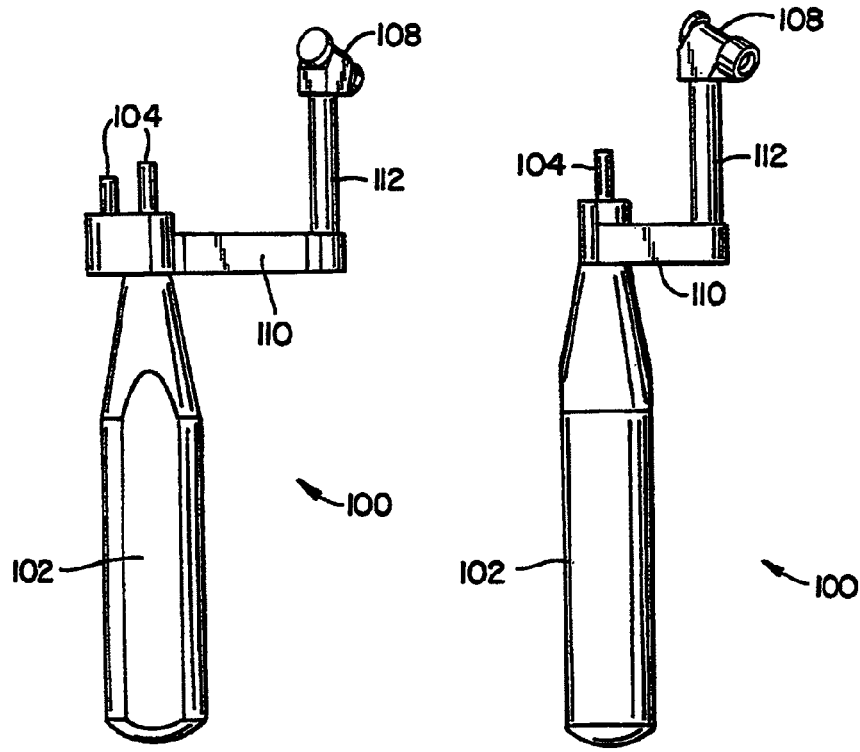
FIGS. 10A-D are views of a guide tool according to one embodiment of the invention.
Figures 10C, 10D:
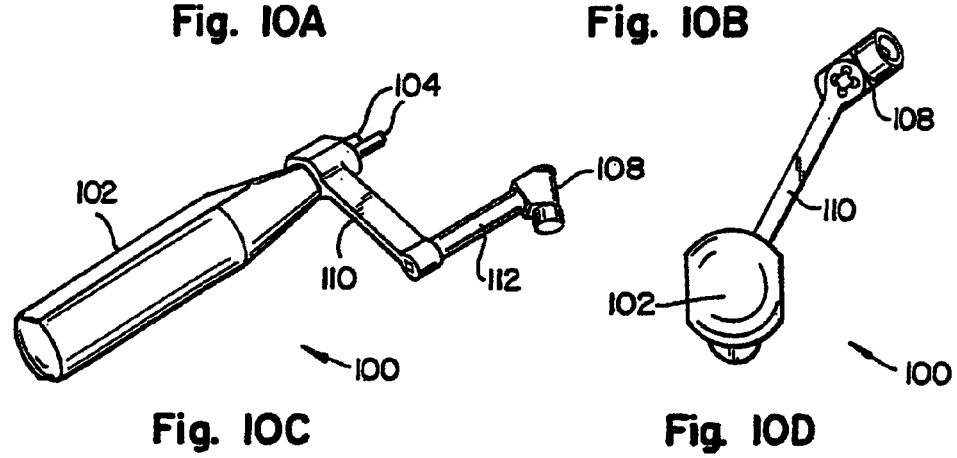

As shown in FIGS. 8 and 9, installation fixture 80 has alignment elements 82 to align the cephalad bearing elements 38 and caudal bearing elements 52. In this embodiment, the alignment elements are two dowels for each bearing element. Alignment elements 82 mate with corresponding alignment elements in the bearing elements, such as holes 84 (shown, e.g., in FIG. 7B) formed in cephalad bearing elements 38 and caudal bearing elements 52. Other alignment elements may be used, of course, such as pins, grooves, indentations, etc. Attachment elements such as screws 86 attach the bearing elements 38 and 52 to the installation fixture via screw holes 88 (shown, e.g., in FIG. 7B) formed in the bearing elements and in installation fixture 80.

When attached to installation fixture 80, cephalad and caudal bearing surfaces 40 and 54 are in contact and in proper alignment with respect to each other, as shown in FIG. 8. In one embodiment, the cephalad and caudal bearing surfaces 40 and 54 are desirably "preloaded" and/or positioned to be in compression/contact when attached to installation fixture 80. In alternative embodiments, the components of the prosthesis could be implanted while the joint structure is being distracted, or while the joint is held together either by the natural tissue or an artificial construct, or combination thereof. These bearing surfaces can desirably be positioned to either (1) come in contact with each other when the distraction is released, or (2) contact each other and be compressively loaded when the distraction is released. To bring the pairs of bearing surfaces in proper alignment with respect to the patient's vertebrae, the spacing between the pairs of bearing surfaces might require adjustment in various embodiments. In the embodiment of FIGS. 8, 9 and 11-14, installation fixture 80 has two bearing support components 90 and 92 that move in a controlled manner with respect to each other. Specifically, in this embodiment a threaded shaft 94 extends between support components 90 and 92. Shaft 94 engages bores formed in support components 90 and 92; one or both of the bores are threaded so that rotation of shaft 94 causes support components 90 and 92 to move towards or away from each other. Shaft 94 may be provided with a thumbwheel 96 or other actuator for ease of use. One or more guide rods 98 may be provided to maintain the alignment of support components 90 and 92. Other means of moving the cephalad/caudal bearing elements pairs with respect to each other may be used, such as a guided or unguided sliding connection between installation fixture elements.

Figure 11:
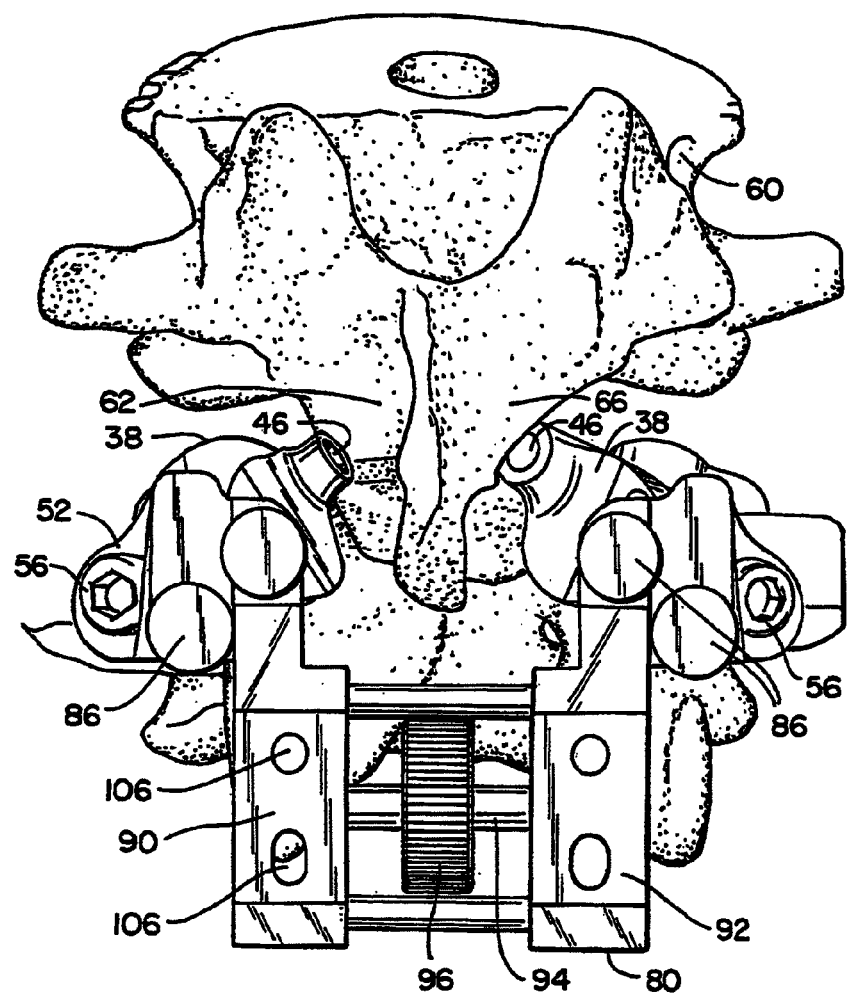
FIG. 11 is a posterior view of the installation fixture of FIGS. 8 and 9 to which a pair of caudal facet bearing elements and a pair of cephalad bearing elements have been attached and with the caudal bearing elements attached to the patient.
Figure 12:
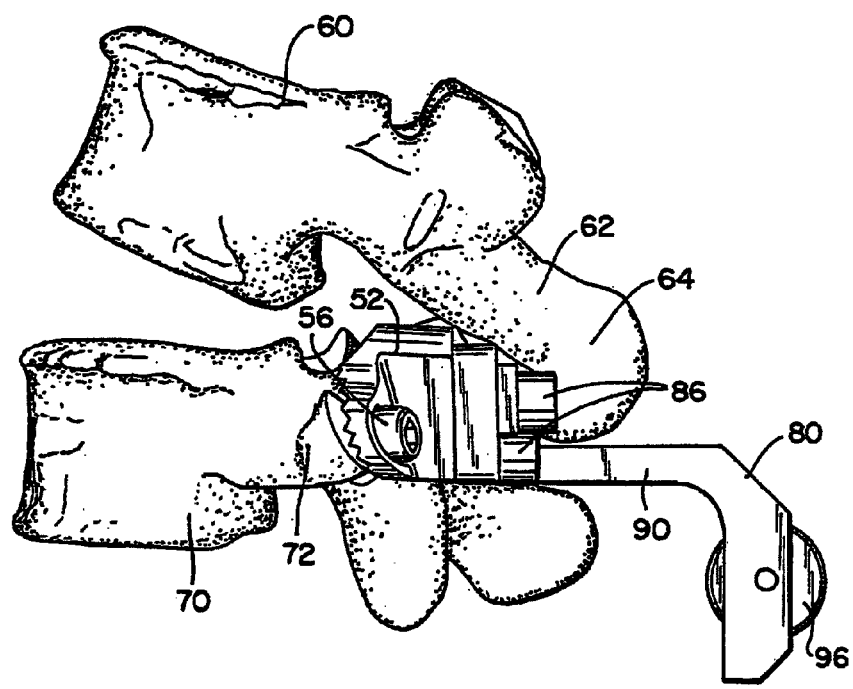
FIG. 12 is a left side view of the installation fixture and bearing elements of FIG. 11 with the caudal bearing elements attached to the patient.

In use, after preparing the implant site by removal of all or a portion (if desired and/or necessary) of existing natural cephalad and caudal facet joint portions of the cephalad and caudal vertebrae 60 and 70, respectively, of the spine motion segment, bearing elements 38 and 52 are attached to installation fixture 80 as described above. The spacing between the bearing element pairs is then adjusted using thumbwheel 96 to align the fixation holes 58 of caudal bearing elements 52 with the proper fixation screw insertion sites in the pedicle portions of the caudal vertebra (or other suitable location), thus placing the artificial facet joints in positions corresponding to the position of natural facet joints or in any other position desired by the physician, including positions that do not correspond to the position of natural facet joints. Passages aligning with holes 58 are formed in the pedicle—or into another part of the caudal vertebra near or adjacent to the pedicle—using a drill, awl, pedicle probe, or other tool known in the surgical arts. Fixation screws 56 are then inserted through holes 58 into the pedicle or other portion of the caudal vertebra to attach the caudal bearing elements as well as the entire prosthesis and installation fixture to the caudal vertebra 70, as shown in FIGS. 11 and 12. Alternatively, self-tapping screws or other caudal fixation elements may be used, thereby eliminating the need to pre-form the passages.

Thereafter, the cephalad bearing elements are attached to the cephalad vertebra 60. In one embodiment, an insertion path is first determined for each fixation element, then a passage is formed along the insertion path corresponding to cephalad bearing element holes 46 (e.g., in the lamina at the base of the spinous process and through the lamina on the other side, through only one lamina portion, through the spinous process, etc.). Fixation screws 42 can then be inserted through the holes 46 into the passages. Alternatively, self-tapping screws or other caudal fixation elements may be used, thereby eliminating the need to pre-form the passages.

After all four bearing elements have been affixed, the installation fixture 80 may be detached and removed. Installation fixture 80 may be used to implant fewer than four bearing elements, of course.

Figure 13:
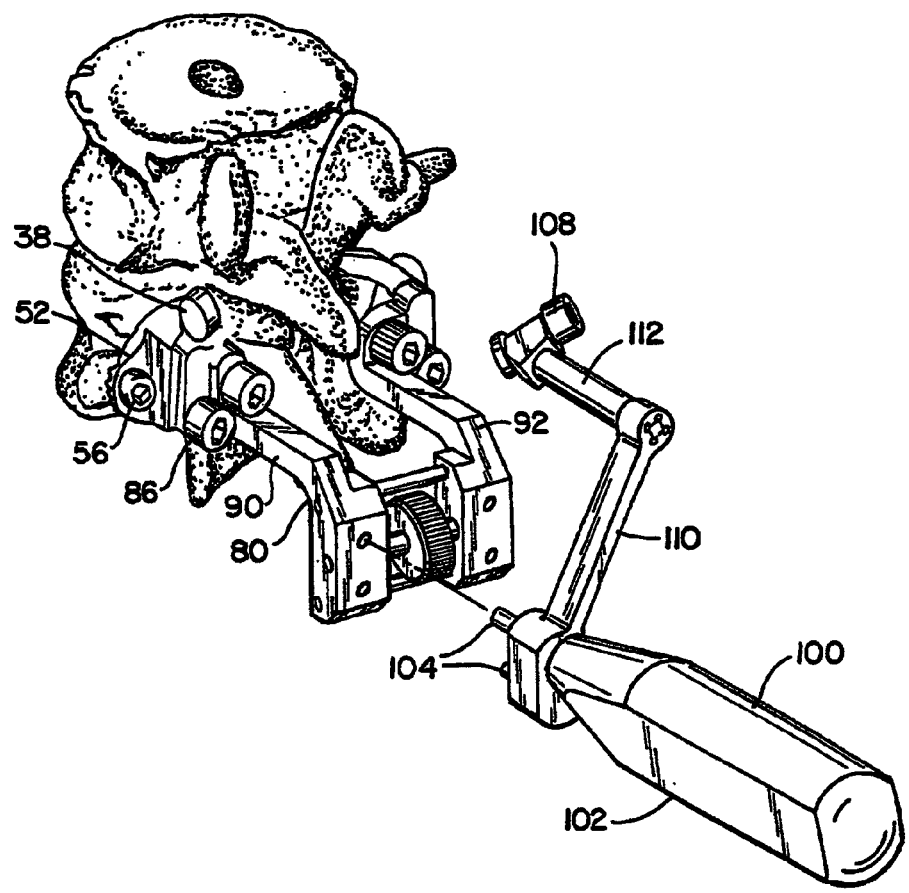
FIG. 13 is a perspective view of the installation fixture and bearing elements of FIGS. 11 and 12 showing a guide tool according to one embodiment of this invention.
Figure 14:
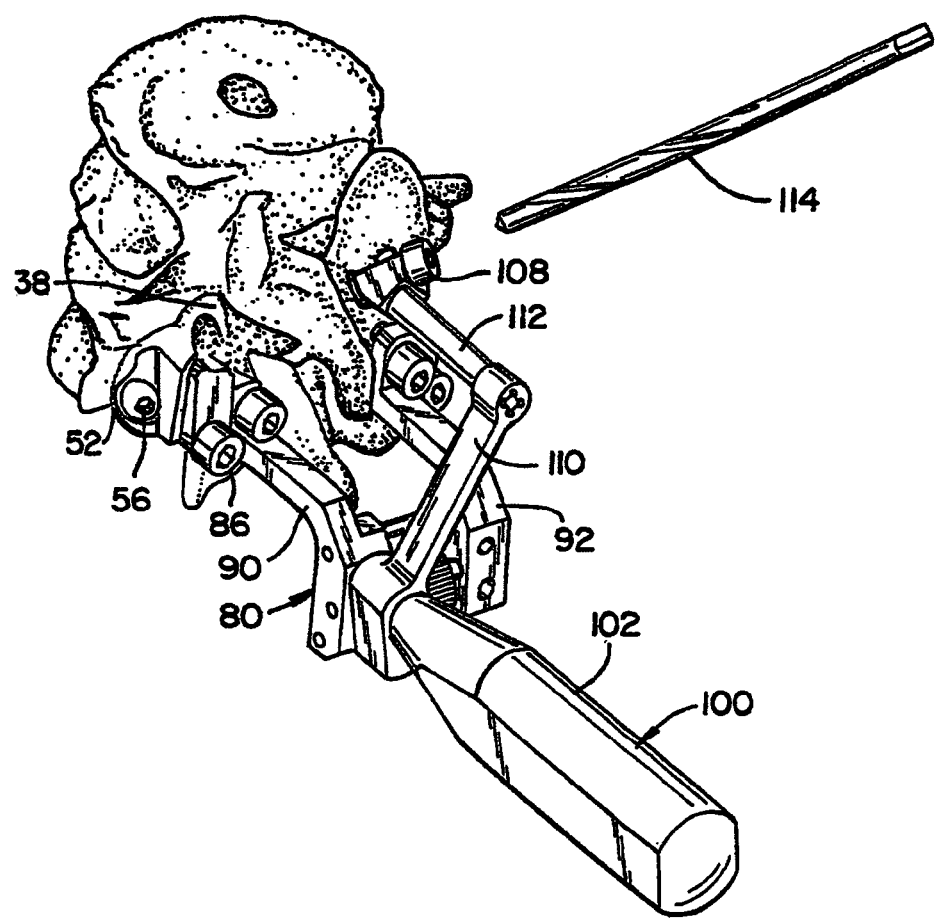
FIG. 14 is a perspective view of the installation fixture and bearing elements of FIGS. 11 and 12 showing the use of a drill bit with the guide tool according to one embodiment of this invention.

FIGS. 10, 13 and 14 show a tool that may be used to define the insertion path (location, orientation, etc.) for the fixation element of the left cephalad bearing element. For example, the tool may be used to guide the formation of a cephalad bearing element attachment passage for the left bearing element. A corresponding mirror image tool may be used for the right cephalad bearing element. In alternative embodiments, a single tool may be used for defining the insertion path for both left and right cephalad bearing elements.

As shown, tool 100 has a handle 102 and an alignment interface (such as dowels 104 in tool 100 and holes 106 in fixture 80) to align the tool in the proper orientation with respect to installation fixture 80 and a cephalad facet joint bearing element. With the caudal and cephalad bearing elements still attached to installation fixture 80 and preferably with caudal bearing elements already affixed to the caudal vertebra 70, the tool 100 engages installation fixture through the alignment interface as shown in FIGS. 13 and 14. In this position, the tool 100 may be used to define an insertion path for the cephalad fixation elements.

In the embodiment shown in FIGS. 10, 13 and 14, the insertion path guide is a drill guide 108 supported by arms 110 and 112 and is aligned with the hole 46 in cephalad bearing element 38 by the alignment interface between installation fixture 80 and guide tool 100. In this embodiment, the drill guide 108 is a tube, but other guide elements may be used, such as a guide groove or surface. (Alternatively, the insertion path guide could be an 11-gage spinal needle, or a cannula sized to accommodate the cephalad prosthesis components for a minimally invasive—MIV—procedure.) A drill bit 114 may be inserted through the drill guide 108 to form an insertion passage, such as a passage through a lamina portion of the cephalad vertebra. A fixation screw may then be inserted through the passage in the cephalad vertebra and into the Morse taper connection of the hole 46 (or other type connection, as discussed above) of the cephalad bearing element 38. As discussed above, the fixation screw may be coated with a bone ingrowth material. Alternatively, a self-tapping screw may be used, thereby removing the need to pre-form a passage.

In order to determine the length of the passage (especially during a minimally invasive procedure), as well as to prevent over-drilling of the passage, the proximal shaft of the drill can include a drill-stop (not shown) to prevent advancement of the drill into the cannula beyond a desired depth. Similarly, the proximal shaft of the drill can include depth markings which, when the drill exits the passage, can be used to determine the length of the passage created in the lamina. Desirably, subtracting the length of the cannula (which is known) from the depth markings can provide an accurate estimate of the passage length, and thus assists the physician in the choice of the proper size cephalad implant to fill the passage.

A mirror image tool may then be used to define an insertion path or to form a hole for the right cephalad bearing element, which is then affixed to the vertebral body in the same way. The installation fixture is then removed, such as by unscrewing screws 86.

As mentioned above, in alternative embodiments the guide tool may be used to define a path for a self-tapping screw or other fixation element that does not require the use of a drill. In those embodiments, element 108 may be used to define a path for the self-tapping screw or other fixation element. The fixation element path may be through only a single lamina portion, through the spinous process alone, or any other suitable path.

In some embodiments, the entire prosthesis other than the bearing surface may be coated with bone ingrowth material.

Figure 15A:
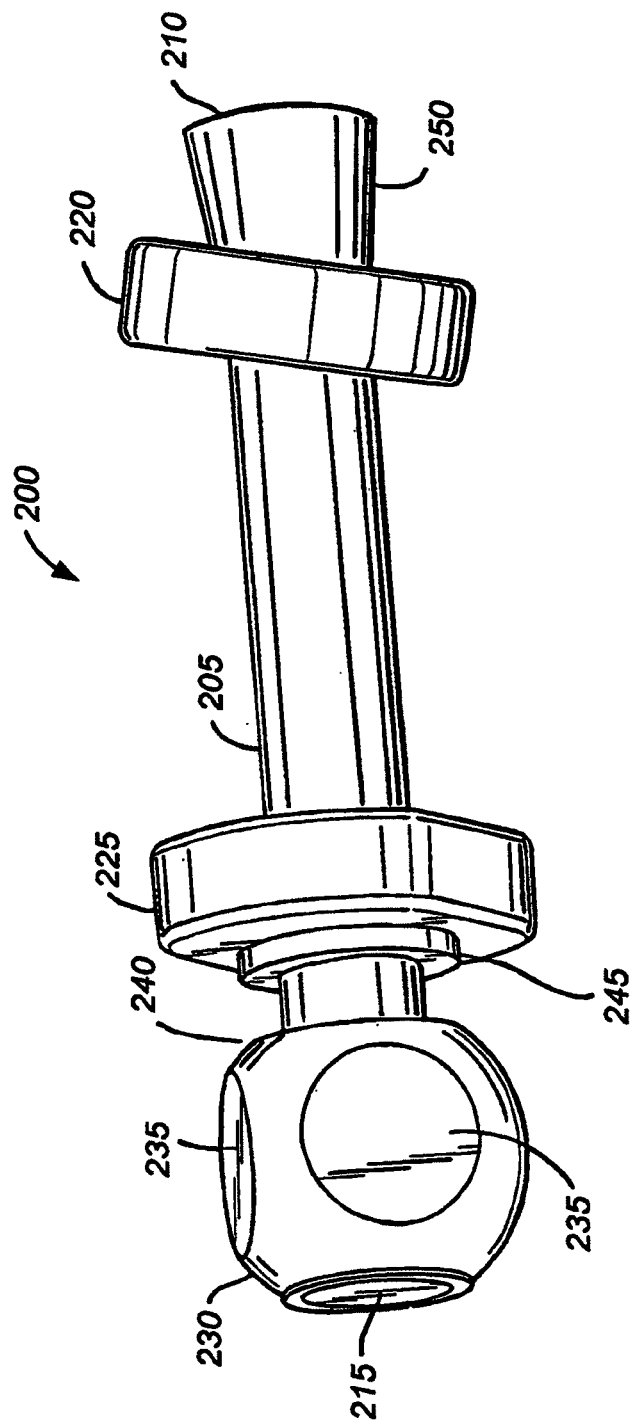
FIGS. 15A and 15B are a perspective and cross section views, respectively, of a cephalad prosthesis embodiment of the present invention.
Figure 15B:
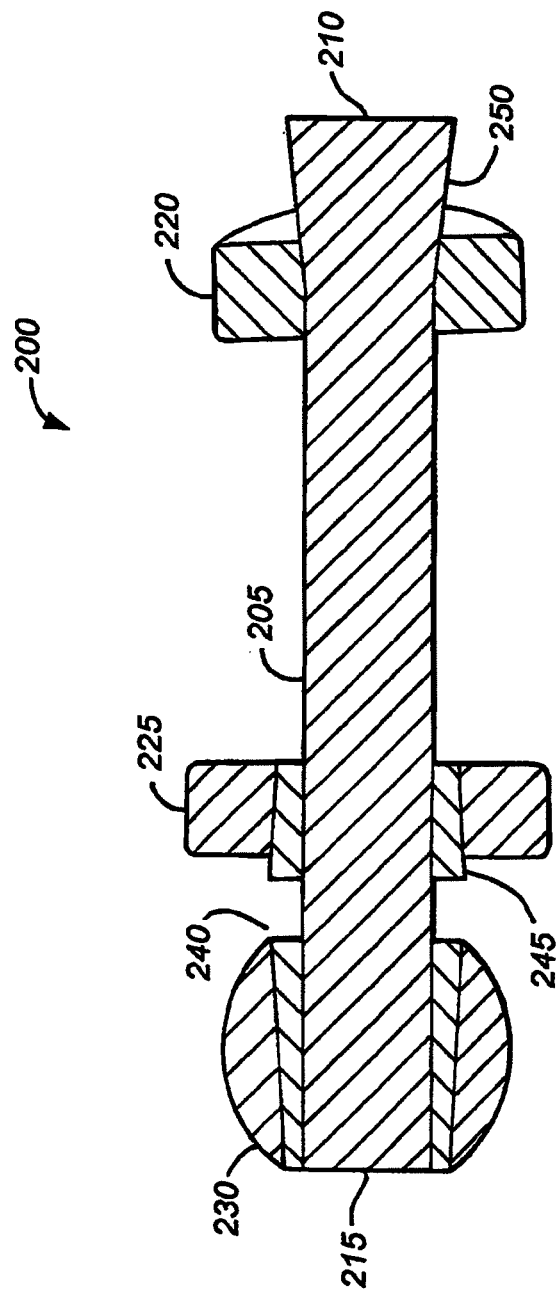

FIGS. 15A and 15B depict a side plan and cross-sectional view, respectively, of an alternate embodiment of a cephalad portion of a facet replacement prosthesis constructed in accordance with the teachings of the present invention. In this embodiment, the facet prosthesis 200 comprises a substantially cylindrical body 205 having a proximal end 210, a distal end 215 and an expanded section 250 adjacent the proximal end 210. In use, a proximal collar 220 is adapted to secure against the proximal end, preferably against a portion of the expanded section 250. A distal collar 225 is secured about the body 205 in a position proximal to the distal end 215. A ball 230, incorporating one or more bearing surfaces 235, is positioned at the distal end 215. The ball 230 is an example of a prosthetic bearing element adapted to form a part of an articulating process in the spine. As illustrated, the ball 230 has an outer surface and an internal opening adapted to fit over the elongate body distal end. While the dimensions and specific design of the ball 230 and collars 220, 225 may secure to the body 205 unaided, the illustrated embodiment of the prosthesis 200 includes a ball shim 240 to aid in securing the ball 230 into position on the body 205, and a distal collar shim 245 to aid in securing the distal collar 225 into position on the body 205. While the body 205 is illustrated and described having a circular body, it is to be appreciated that other non-circular shapes, such as for example, triangular, rectangular or other polygonal shape may be used and the components described herein adapted as needed. Non-circular cross section bodies advantageously provide the prosthesis an anti-rotation capability.

In additional alternative embodiments, features, compounds, or surface treatments may be utilized to enhance attachment between the various components of the prosthesis 200 or between the prosthesis 200 and vertebral bone. For example, portions of the collars 225, 220 that interact with the body 205 may be textured or have teeth to promote a stronger attachment when joined to the body 205. Similarly, portions of the collars 225, 220 that come into contact with the lamina/spinous process may also include features or surface textures to promote joining as well as compounds, for example, bone growth compounds or cements, to promote adhesion between the bone and the collars 220, 225. Similarly, the surfaces of the shims 245, 240 may also include features or surface treatments to improve contact and grip between the distal collar 225 and the ball 230, respectively, as well as the body 205. In much the same way, the exterior surface of the body 205 may also be adapted to include features, compounds, or surface treatments to improve contact with the shims 245, 240, collars 225, 220, ball 230 and the exposed bone in the passage 290 (see FIG. 16A).

In one specific embodiment, the prosthesis 200 has an elongated cylindrical body with a length of 40 mm, a minimum diameter of 4 mm, a distal end that expands to approximately 5 mm, and a ball 230 having a metal sphere with a diameter of approximately 10 mm. The size, length and dimensions of the components of prosthesis 200 may vary and be selected based on a number of criteria. Examples of selection criteria include the age and sex of the patient, the specific pathology and anatomy of the patient and the specific spinal level where implantation will occur. The measurement techniques and tools described herein may be used to determine the size, dimensions and placement of a specific prosthesis 200.

Figure 16B:
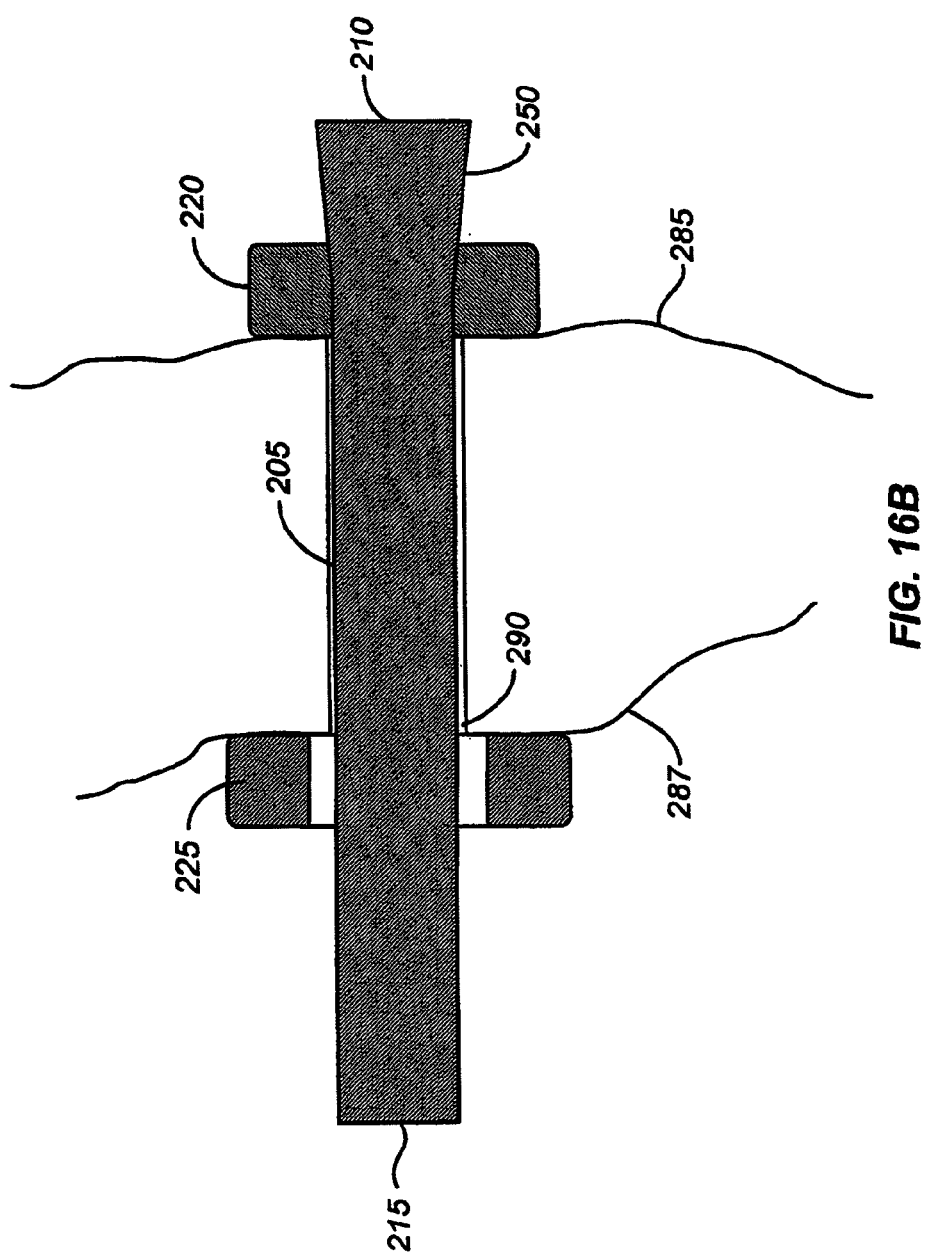

A method for implanting the prosthesis 200 will now be described with reference to FIG. 16A-16D. A passage 290 is formed completely through the remaining lamina and/or spinous process of the cephalad vertebra between a first outer surface of lamina and/or spinous process 285 and a second outer surface of lamina and/or spinous process 287. The passage 290 is adapted to accommodate the prosthesis 200, specifically the body 205 (FIG. 16A). In one specific embodiment, the passage 290 is sized to accept the cylindrical body 205 but not the expanded section 250. To install the prosthesis 200 into a passage 290, a proximal collar 220 is slid over the distal end 215 of the body 205. Note that the proximal collar 220 is sized and shaped to engage with a portion of the expanded section 250. Next, the body 205 is advanced distal end 215 first through the passage 290 until the proximal collar 220 abuts against the first outer surface of the lamina and/or spinous process 285 and the expanded section 250.

Figure 16C:
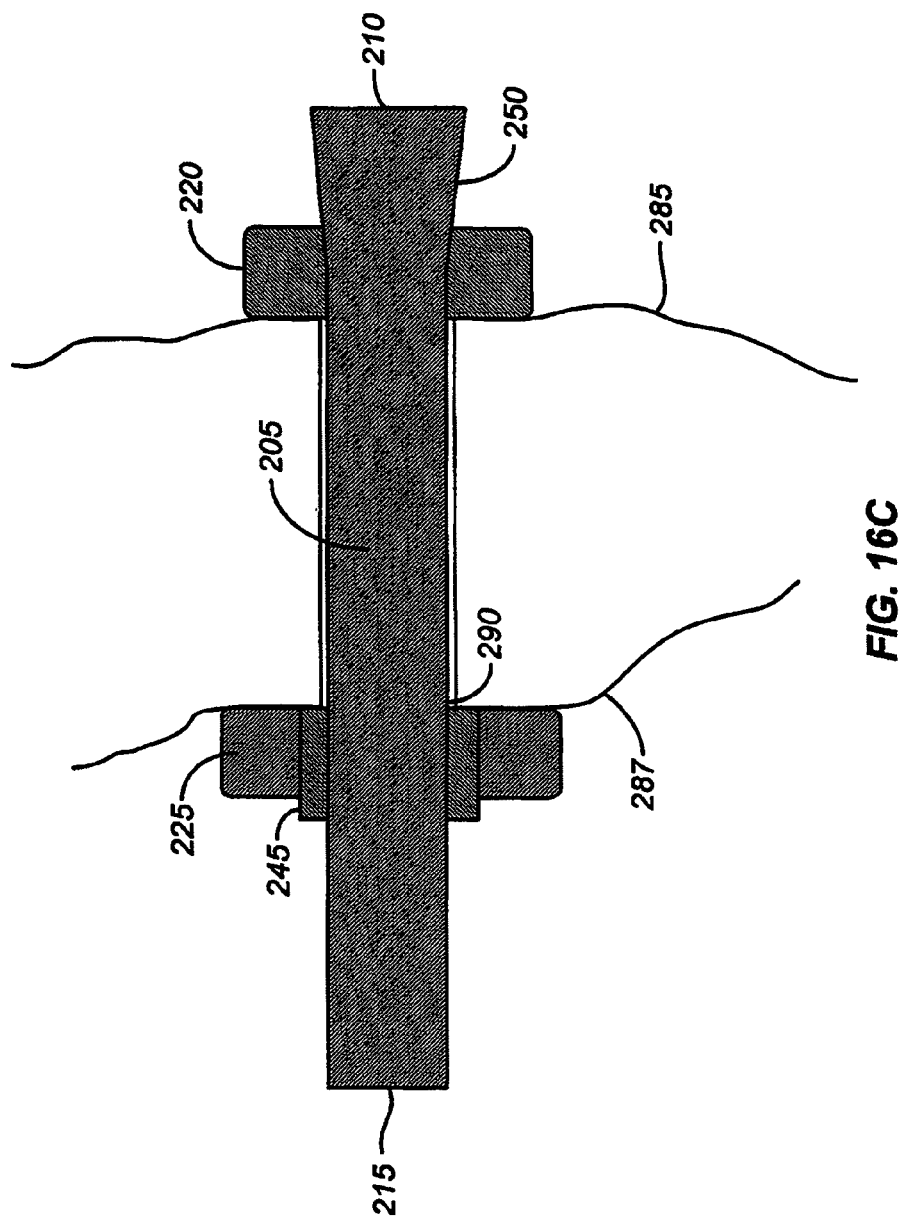

As shown in FIG. 16B, once the distal end 215 exits the passage 290 beyond the second outer surface of the lamina and/or spinous process 287, the distal collar 225 slides over the distal end 215, abutting against the second outer surface of the lamina and/or spinous process 287. Next, as shown in FIG. 16C, a distal collar shim 245 is pushed between the body 205 and the distal collar 225 to secure the distal collar 225 in position. Advantageously, the distal collar 225 and the proximal collar 220 are compressed and/or tightened against the outer surfaces of the lamina 285,287, desirably against one or more cortical bone surface(s) of the lamina and/or spinous process.

Figure 16D:
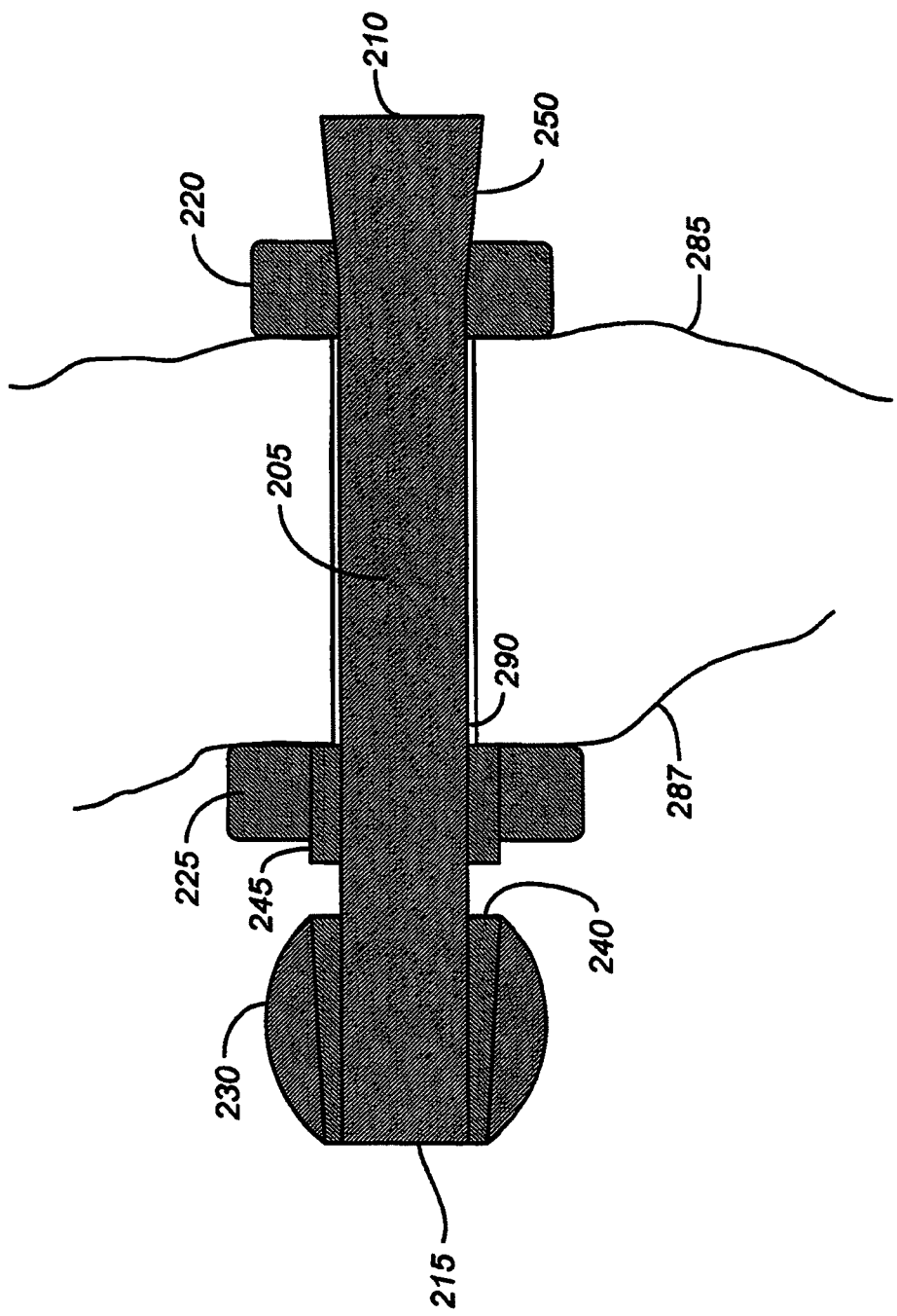
Figure 17:
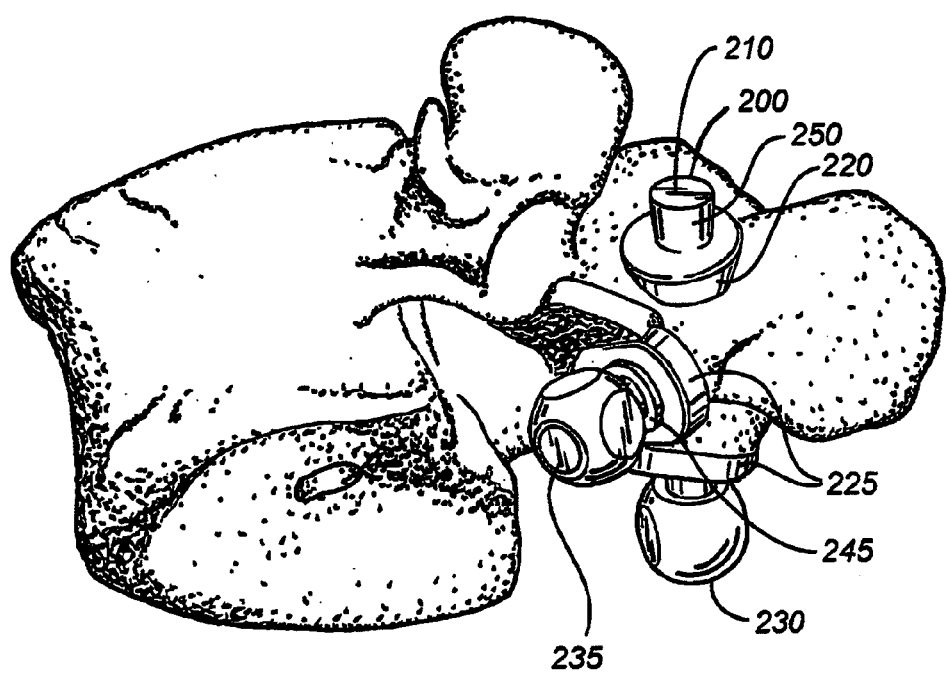
FIG. 17 is a left side perspective view of a pair of cephalad prosthesis embodiments constructed in accordance with the teachings of the present invention implanted into a vertebral body.
Figure 18:
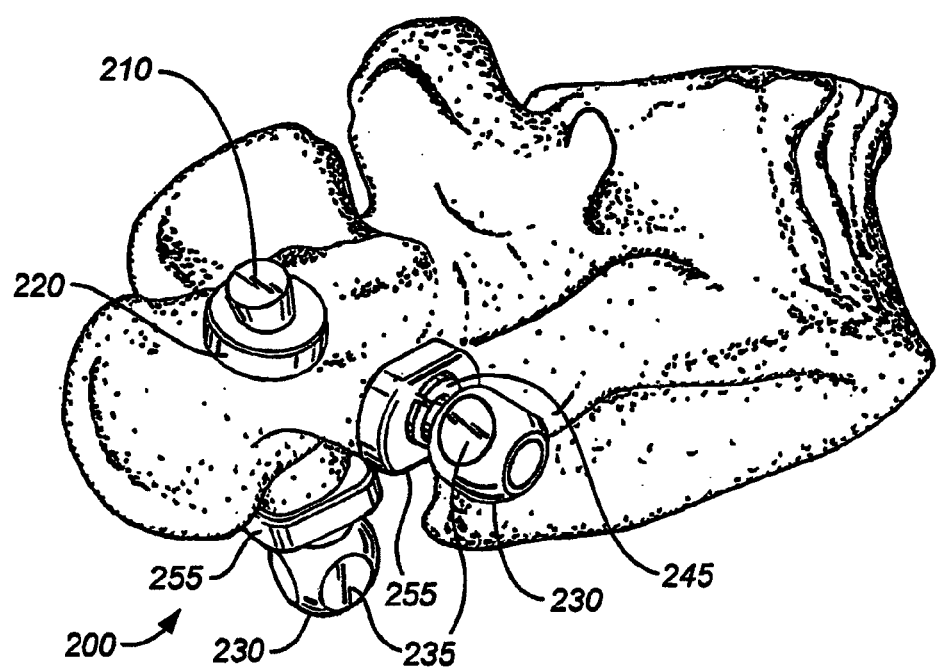
FIG. 18 is a right side perspective view of the cephalad prosthesis of FIG. 17.
Figure 19:
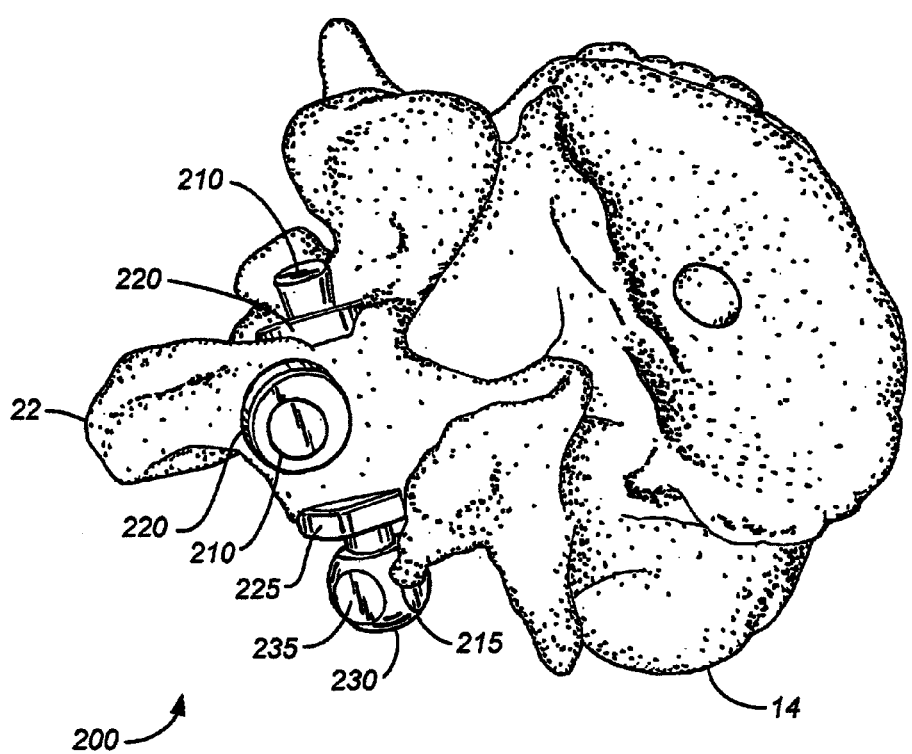
FIG. 19 is an elevated right side perspective view of the cephalad prosthesis of FIGS. 17 and 18.
Figure 20:
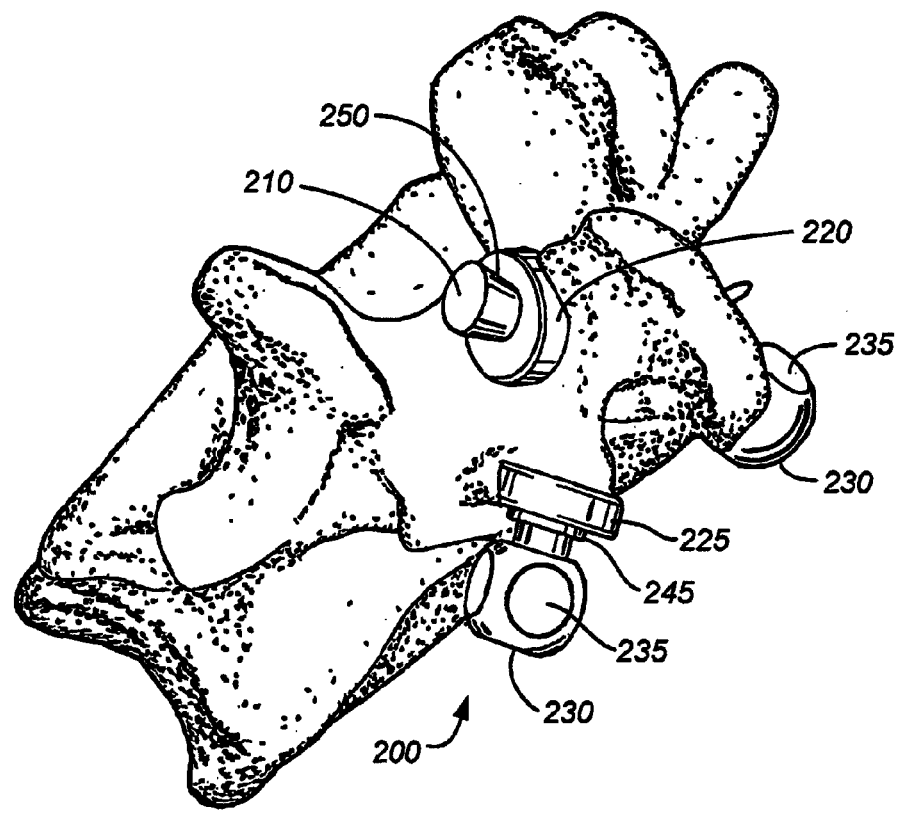
FIG. 20 is an elevated left side perspective view of the cephalad prosthesis of FIG. 17.

Next, as shown in FIG. 16D, the ball shim 240 and bearing 230 are advanced over the distal end 215. Similarly, the ball shim 240 is used to wedge the bearing 230 into the desired position relative to the distal end 215. If desired, a prosthesis 200 for replacing the opposing cephalad facet joint on the same vertebral body can be placed in a similar manner into a corresponding passage 290 through the lamina and/or spinous process resulting in two prosthesis per level as illustrated, for example, in the several views of FIGS. 17-20.

As best shown in FIGS. 17 through 20, a pair of such prosthesis 200 can be secured through the lamina and/or spinous process of a targeted vertebra to replace a pair of natural cephalad facet structures. As previously noted, the surgical procedure may include, but is not limited to, the removal and/or resection of one or more sections of the lamina and cephalad/caudad facet joint structure to alleviate nerve compression and/or spinal stenosis, remove disease or damaged tissues, prepare the intervertebral disk space to receive an artificial disk replacement/augmentation prosthesis, provide access to spinal structures, or for other reasons.

In one embodiment of a surgical procedure for implanting the prosthesis 200, the targeted facet capsule is initially exposed (the open portion) using standard open surgical techniques. The facet capsule is then opened and/or removed, and the superior and/or inferior facets are resected and/or removed as necessary (using a surgical cutter or rongeur) during the surgical procedure. If replacement of the caudal facet section is deemed necessary, a caudal stem and associated caudal bearing can be implanted into the exposed pedicle through the open incision.

Advantageously and in contrast to conventional techniques where both the cephalad and caudal prosthesis are implanted via an open procedure, a majority of the components of the prosthesis 200 can be surgically implanted using minimally-invasive techniques alone or in combination with conventional open techniques. For example, all or most of the prosthesis 200 may be delivered through a cannula inserted through a small incision in the skin. To implant the cephalad implant, the physician can first create an access path through the skin and soft tissue (with a spinal needle and/or K-wire) to the lamina of the targeted vertebral body. Desirably, non-invasive visualization, such as fluoroscopic or real-time MRI, is used to monitor the advancement of the needle and avoid damage to tissue structures such as muscles, tendons, ligaments, nerves, veins and/or the spinal cord itself. Once the access path has been created, a suitable cannula can be advanced through the tissues to the targeted bone. If necessary, progressively larger dilation catheters (such as the Access™ Dilation Port commercially available from Spinal Concepts of Austin, Tex.) can be used to introduce a cannula having a lumen large enough to accommodate passage of the cephalad implant (i.e., the body 205 and proximal collar 220). In alternative embodiments, one cannula is positioned and adapted to deliver the body 205 and the proximal collar 220 and another cannula is positioned and adapted to deliver the remaining prosthesis components.

Once the cannula is in position against the lamina, a drill is advanced through the central opening in the cannula and drills into and through the targeted portion of the lamina and/or spinous process, creating a passage through the lamina. Desirably, a positioning tool (such as the tool 100 shown in FIGS. 10A-10D) will be used to align the cannula and/or drill (and thus the passage created) such that the passage is aligned to permit the bearing surface of the cephalad implant to mate with the corresponding caudal bearing surface. In at least one embodiment, the position of the drill tip can be visually verified (as the drill tip exits the lamina) through the open incision. In one alternate embodiment, the positioning tool aligns the cannula and/or drill relative to the caudal bearing surface. In another alternate embodiment, the positioning tool aligns the cannula and/or drill relative to the upper endplate of the caudal vertebral body, either prior, during, or after the initial access through the patient's skin and/or during the surgical procedure.

After creation of the passage 290, the drill (and any alignment frame, if desired) is removed (with the cannula desirably remaining in place in the patient), and the cylindrical body 205 and associated proximal collar 220 are advanced through the cannula and into the passage 290 in the lamina. The proximal collar 220 is desirably seated against the near surface of the lamina (i.e., the first outer surface of the lamina or spinous process 285), with the distal end 215 extending out of the far surface of the lamina into the open incision (i.e., beyond the second outer surface of the lamina or spinous process 287.) The distal collar 225 and shim 245 are then placed on the distal end 215 and tightened into position as described above. Desirably, the distal and proximal collars 225, 220 will compress and bear directly against the far and near outer surfaces of the lamina and/or spinous process 285, 287, with the lamina and/or spinous process in between. Once the cephalad implant is secured in its desired position, the cannula can be removed, if desired.

Next, using the access provided by the open incision, the ball 230 is positioned over the distal end 215 into the desired position and secured using the shim 240 as previously described. Once the prosthesis 200 is implanted and secured into position, the open surgical site can be closed in a known manner, and the surgical procedure completed.

If desired, various embodiment of the caudal and/or cephalad components disclosed herein could incorporate non-circular posts or stems for anchoring the devices. Passages to accommodate such constructs could be created using broachers, reamers, awls, punches or the like. Such non-circular stems would desirably reduce and/or prevent unwanted rotation of these components along their longitudinal axis.

Figure 21:
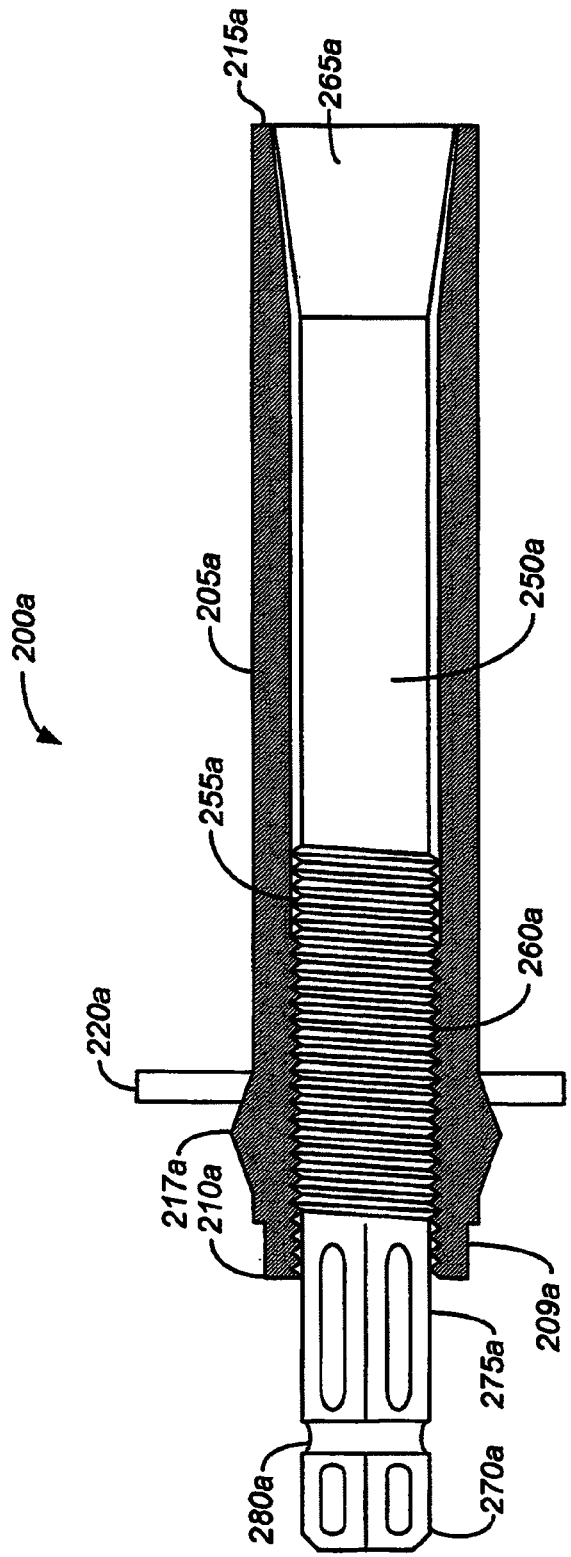
FIG. 21 is a cross-sectional view of an alternative embodiment of a cephalad prosthesis constructed in accordance with the teachings of the present invention.

FIG. 21 depicts an alternate embodiment of the present invention constructed in accordance with the teachings of the present invention. Because many features of this embodiment are similar to components previously-described in connection with other embodiments, like reference numerals will be used to describe similar components. The cephalad prosthesis 200a comprises a substantially cylindrical hollow body 205a having a proximal end 210a, a distal end 215a and a longitudinally-extending bore 207a there through. The body 205a exterior has an enlarged outer ridge 217a, and a wrench-engagement section 209a positioned near the proximal end 210a. The size, shape, and contours of the enlarged outer ridge 217a are adapted to engage with the proximal collar 220a (e.g., FIG. 23). The outer or engagement surfaces of the ridge 217a and/or collar 220a may include features, surface treatment or compounds as described herein or known to those of ordinary skill in the prosthetic arts to improve joining between those components or adjacent bone.

Figure 22:
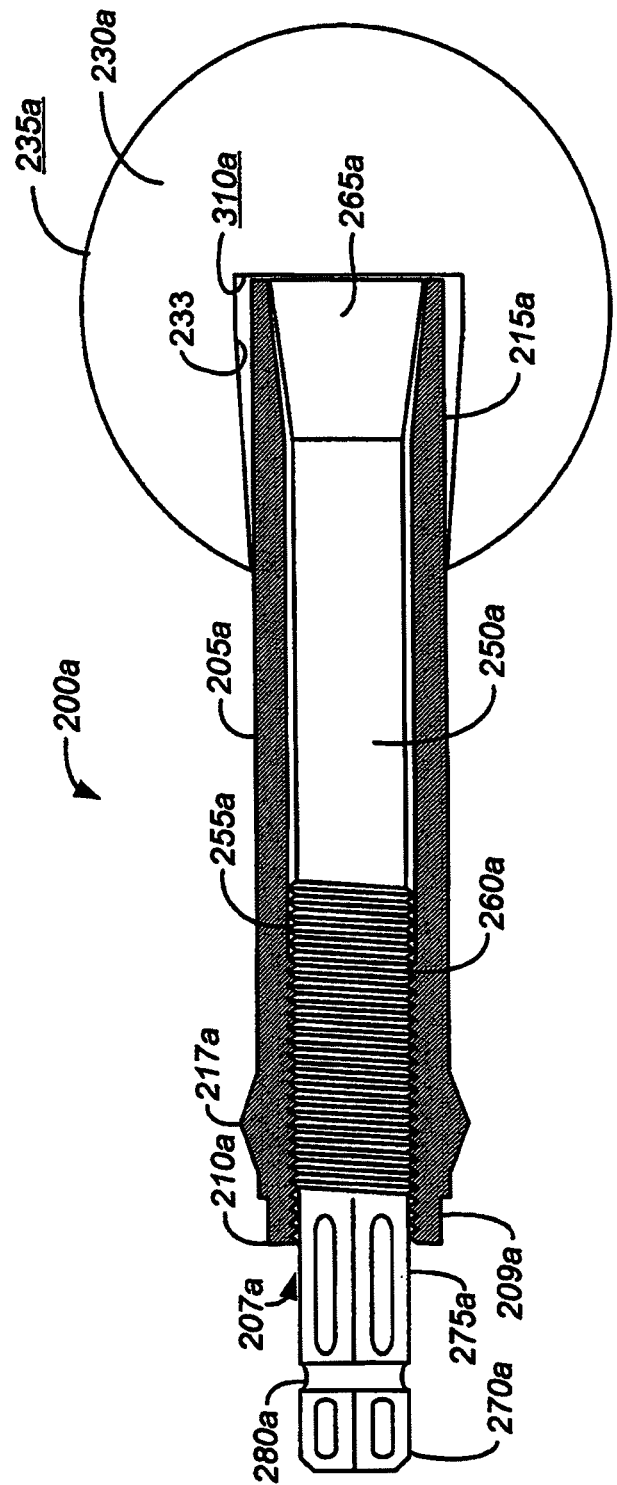
FIG. 22 is a cross-sectional view of the cephalad prosthesis of FIG. 21 with an associated bearing surface element.
Figure 23:
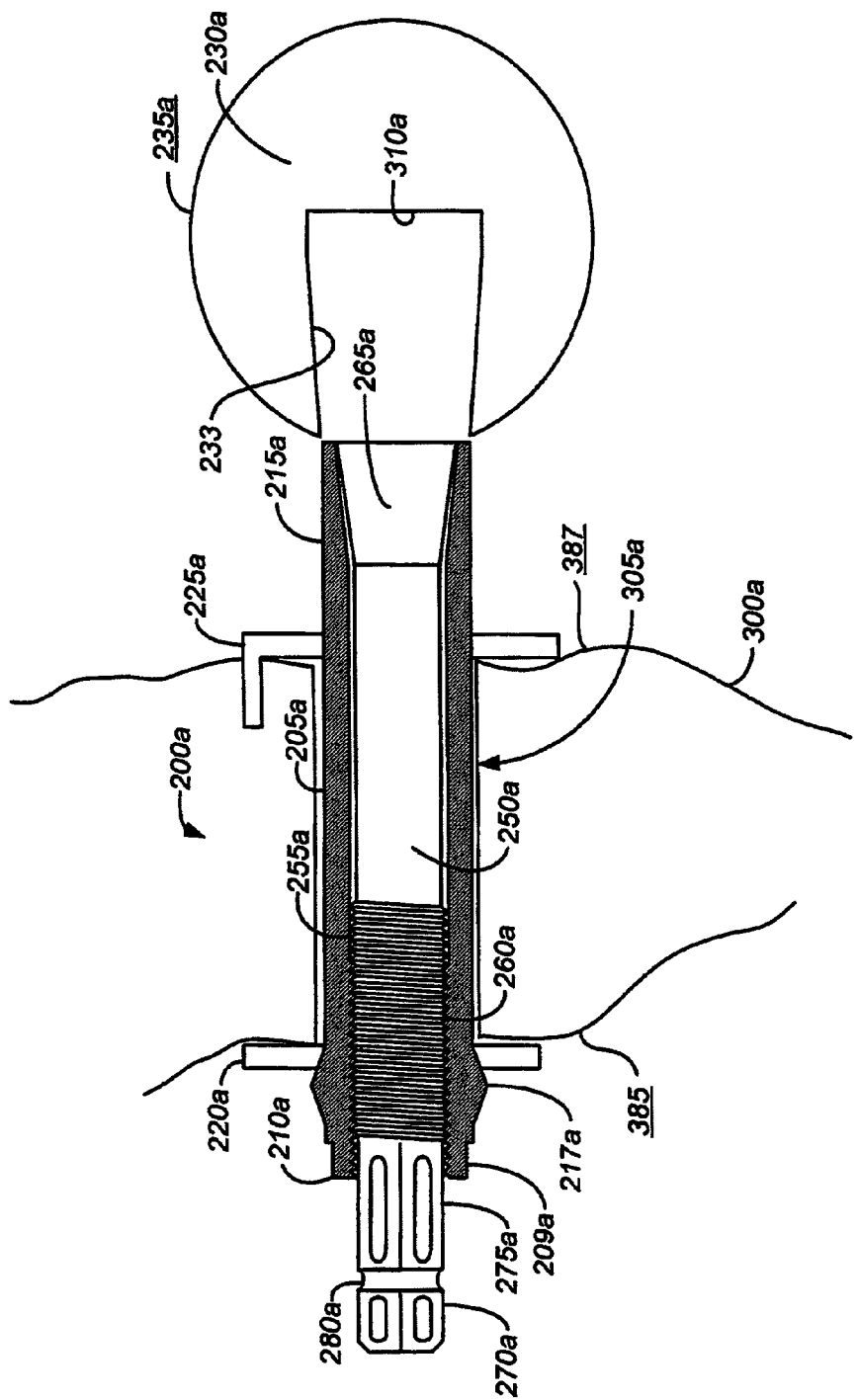
FIG. 23 is a cross-sectional view of the cephalad prosthesis of FIG. 21 in a targeted vertebral body.
Figure 25:
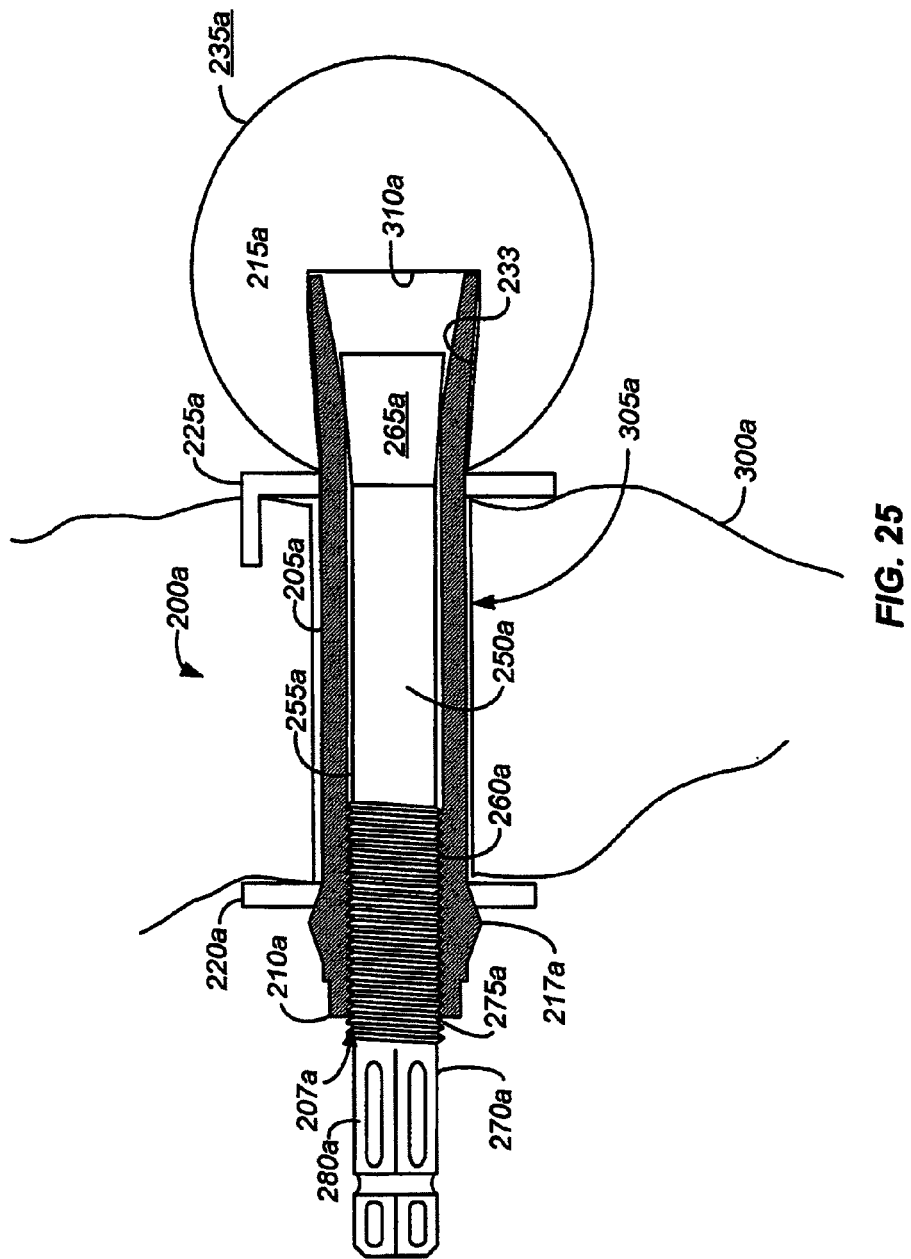
FIG. 25 is a cross-sectional view of the cephalad prosthesis of FIG. 24, showing placement of the bearing surface element in a locked or secured position.

Returning to FIG. 21, a cylindrical shaft 250a, extending through the bore 207a and sized to permit relative movement therein, has a set of external threads 255a which mate with corresponding internal threads 260a inside the bore 207a. The shaft 250a has a proximal drive section 270a, a revision drive section 275a and a notched link 280a there between. The shaft 250a includes an enlarged distal plug 265a sized and adapted to deform the distal end 215a when advanced proximally relative to the body 205a via engagement of threads 255a, 260a. FIGS. 22 and 23 illustrate an embodiment of a bearing 235a having an aperture 233 sized to fit over distal end 215a. The prosthetic bearing 235a is an example of a bearing element adapted to form a part of an articulating process in the spine. The bearing 235a is illustrated adjacent (FIG. 23) and in position over the distal end 215a (FIG. 22, 24) before proximal advancement of the distal plug 265a. When the shaft 250a is advanced, the plug 265a deforms the distal end 215a into pressing contact with the surfaces of the aperture 233 locking the bearing 235a in place (FIG. 25).

To install the cephalad prosthesis 200a in a targeted vertebral body 300a, a passage 305a is drilled completely through the lamina and/or spinous process from a first outer surface 385 to a second outer surface 387 of a lamina and/or spinous process as previously described (the passage 305a is illustrated in FIG. 23). Desirably, the physician will choose and form the passage 305a based on the condition of the lamina, the patient's specific anatomy, the physician's knowledge of anatomy, and the desired final location of the cephalad bearing surface relative to the vertebral body. If desired, the physician can initially place a caudal bearing surface, and then use a jig or other tool to determine the desired orientation and position of the passage that must be created to implant a cephalad prosthesis that properly mates with the caudal bearing surface.

Next, after creating the passage 305a completely through the lamina, the physician will slide a proximal collar 220a over the distal end 215a up to engagement with the exterior surface of the ridge 217a. The body 205a is then advanced distal end 215a first until the proximal collar 220a seats against the first outer surface of the lamina and/or spinous process 385 and the distal end 215a desirably extends out of the other end of the passage 305a (i.e., beyond the second outer surface of the lamina and/or spinous process 387) (FIG. 23). In an embodiment where a combination of an open procedure and minimally invasive procedure are advantageously combined as described above with regard to prosthesis 200, the distal end 215a would extend into the open surgical space while the first outer surface 385 was accessed and the passage 305a was formed using minimally invasive techniques as described herein or known to those of ordinary skill in the surgical arts.

Figure 24:
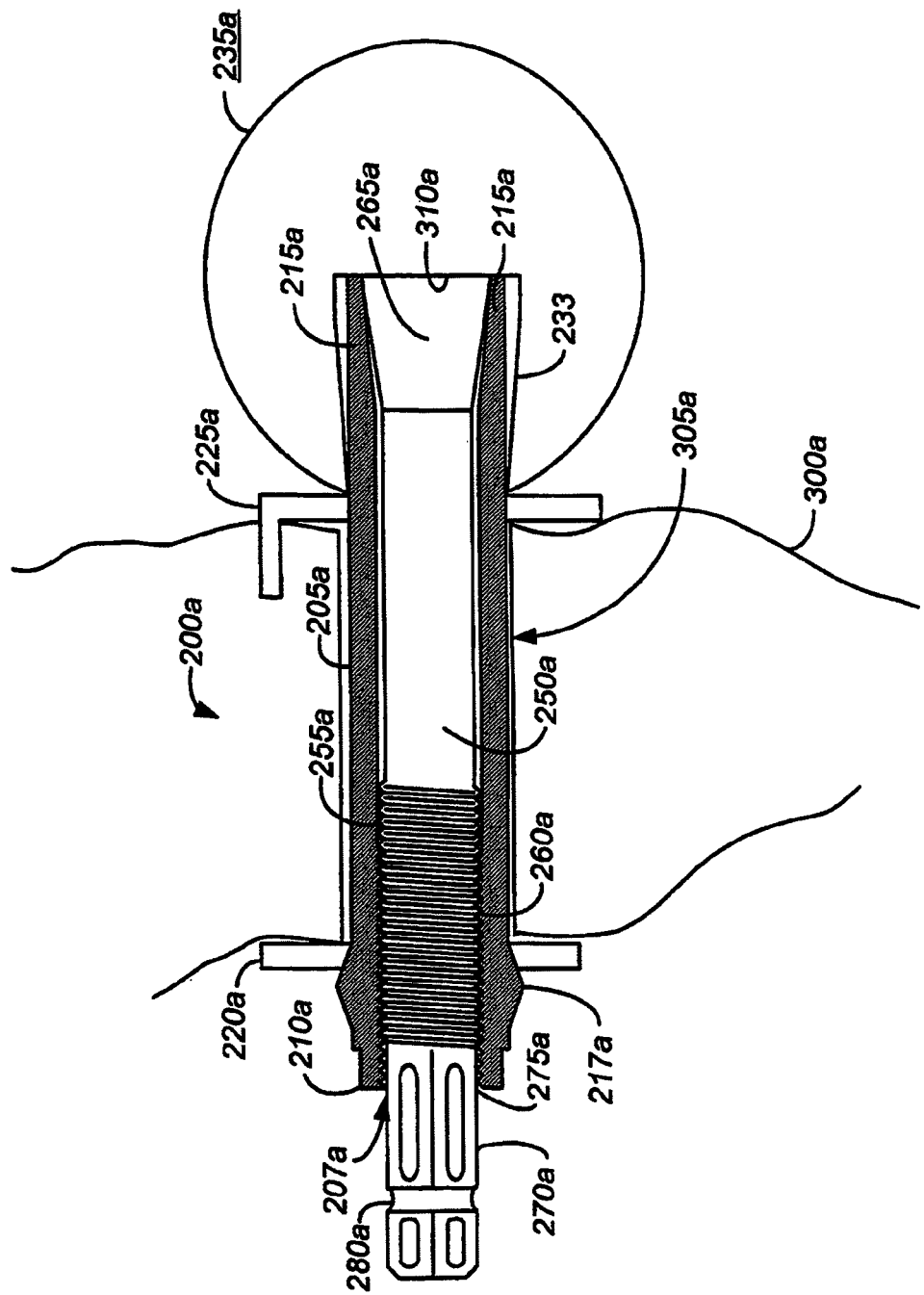
FIG. 24 is a cross-sectional view of the cephalad prosthesis and bearing surface element of FIG. 22, in a targeted vertebral body before securing the bearing surface element.

Next as shown in FIG. 23, a distal collar 225a is advanced over the body distal end 215a until the collar 225a contacts the second outer surface of the lamina and/or spinous process 387. Optionally, a shim or wedge as described above with shims 240, 245, may be driven between the distal collar 225a and the body 205a to secure the distal collar 225 into position. Next, as shown in FIG. 24, the bearing 235a is advanced such that the distal end 215a is disposed within the aperture 233. In the illustrated embodiment, the bearing 235a is advanced over the distal end 215a until the inner surface 310a of the bearing 235a abuts against the body distal end 215a. It is to be appreciated that the bearing 235a may, depending upon a number of factors such as patient anatomy and relationship to other prosthetic components, engage the distal end 215a in a position other than against the inner surface 310a (e.g., FIG. 28). Alternatively as shown in FIG. 25A, an opening 233a may extend completely through a bearing 235b.

Figure 29:
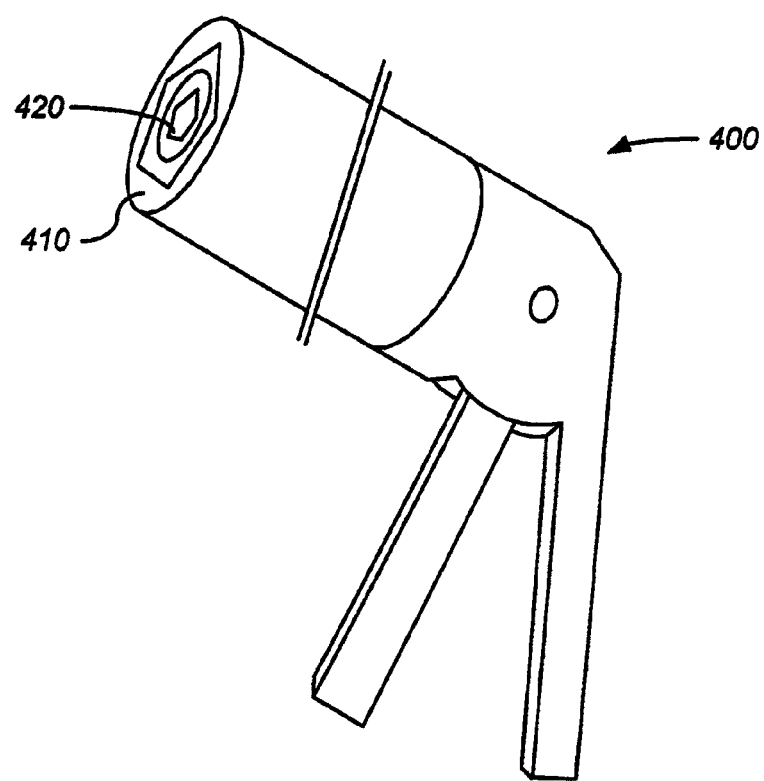
FIG. 29 is a perspective view of a counter-torque wrench suitable for use with various embodiments of the present invention.

Returning now to FIG. 24, once the bearing 230a is properly positioned over the distal end 215a, the physician can utilize a counter-torque wrench 400 (see FIG. 29) having a rotating driver section 420 which engages the proximal drive section 270a of the shaft 250a, and a stationary driver section 410 which engages the wrench-engagement section 209a of the body 205*a*. Desirably, the wrench 400 rotates the drive section 270*a* relative to the wrench-engagement section 209*a* with little or no movement of the prosthesis relative to the lamina. This rotation will desirably draw the enlarged distal plug 265*a* further into the distal end 215*a* of the body 205*a*, causing the distal end 215*a* to expand outward and wedging (and securing) the bearing 230*a* to the body 205*a* (FIG. 25). In one alternate embodiment, the bearing can also secure the distal collar 225*a* against the lamina, rather than by using a shim or wedge to secure the collar 225*a*.

Figure 26:
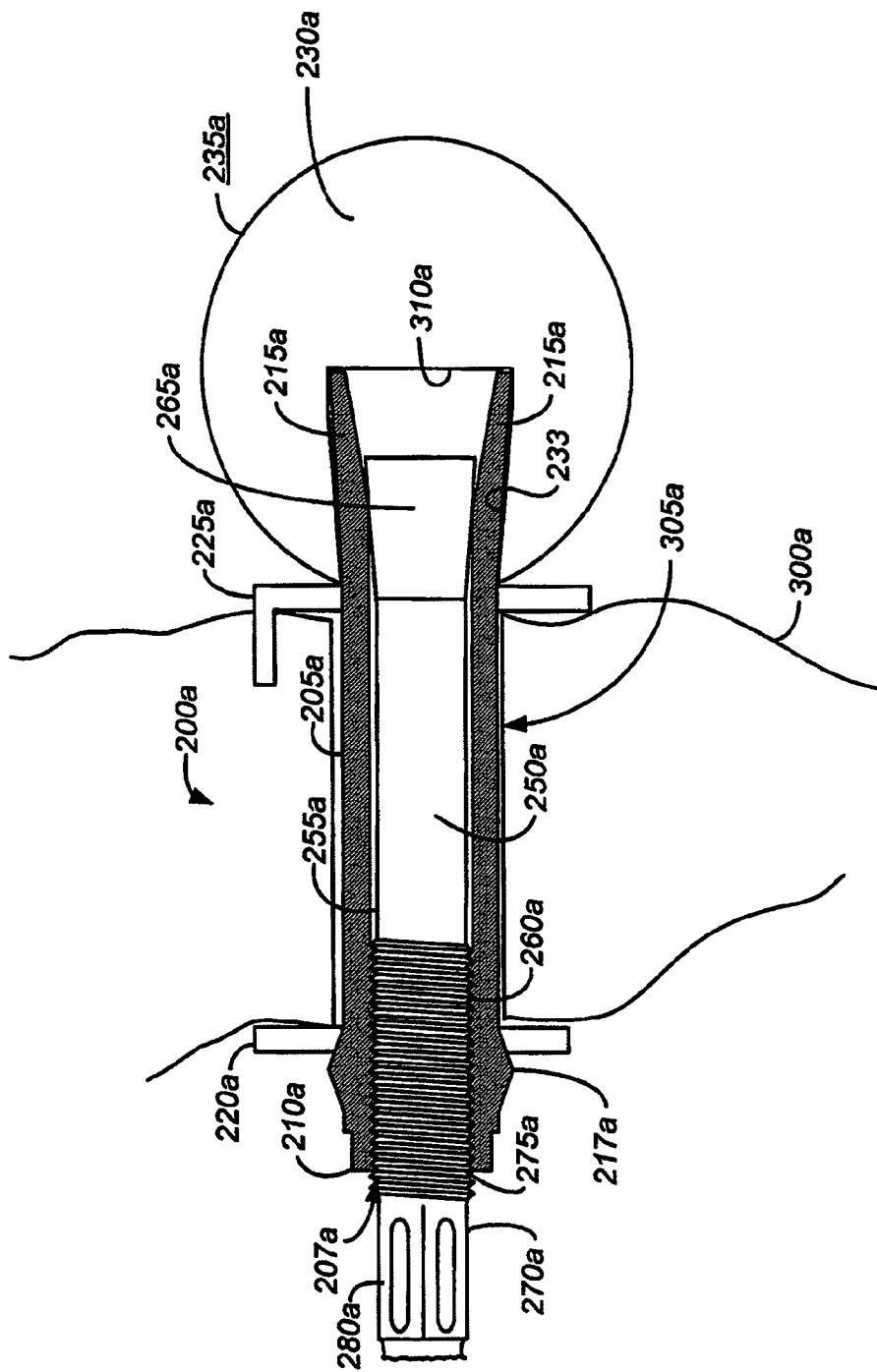
FIG. 26 is a cross-sectional view of the cephalad prosthesis of FIG. 25, after securing the bearing surface element.

Once the bearing 230*a* is secured to the body 205*a* with a pre-determined amount of force, further tightening of the counter-torque wrench will desirably shear the shaft 250*a* at the notched section 280*a*, preventing further rotation and/or over-torqueing of the shaft 250*a* (FIG. 26). If desired, the end of the wrench 400 can include a detent section (or other type of catching or holding mechanism—not shown) which desirably contains the sheared section of the shaft 250*a*.

If desired, implantation of a similar cephalad prosthesis corresponding to the complimentary facet joint can be accomplished in a like manner.

Figure 27:
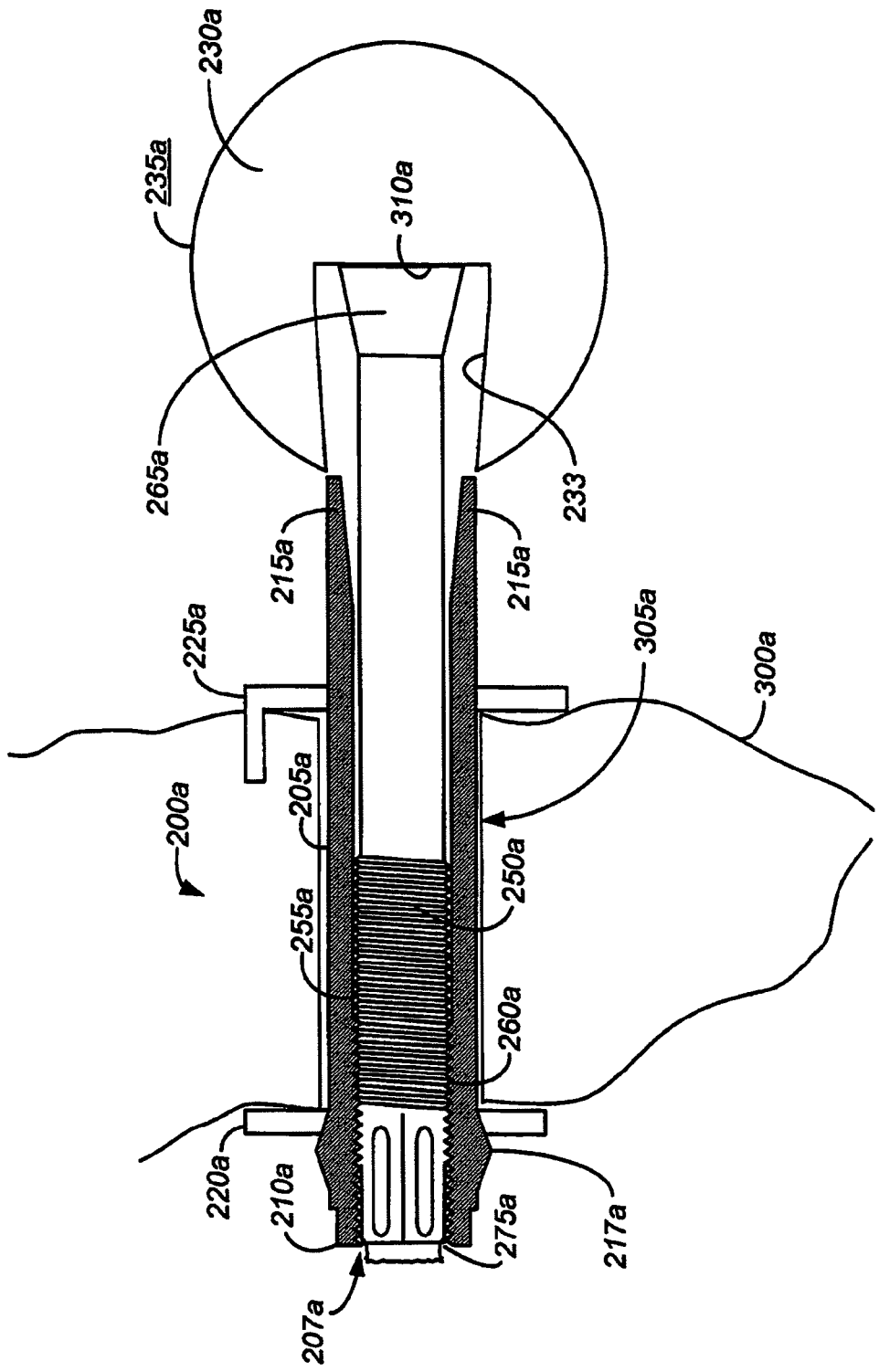
FIG. 27 is a cross-sectional view of the cephalad prosthesis of FIG. 26, after removal of the bearing surface element.
Figure 28:
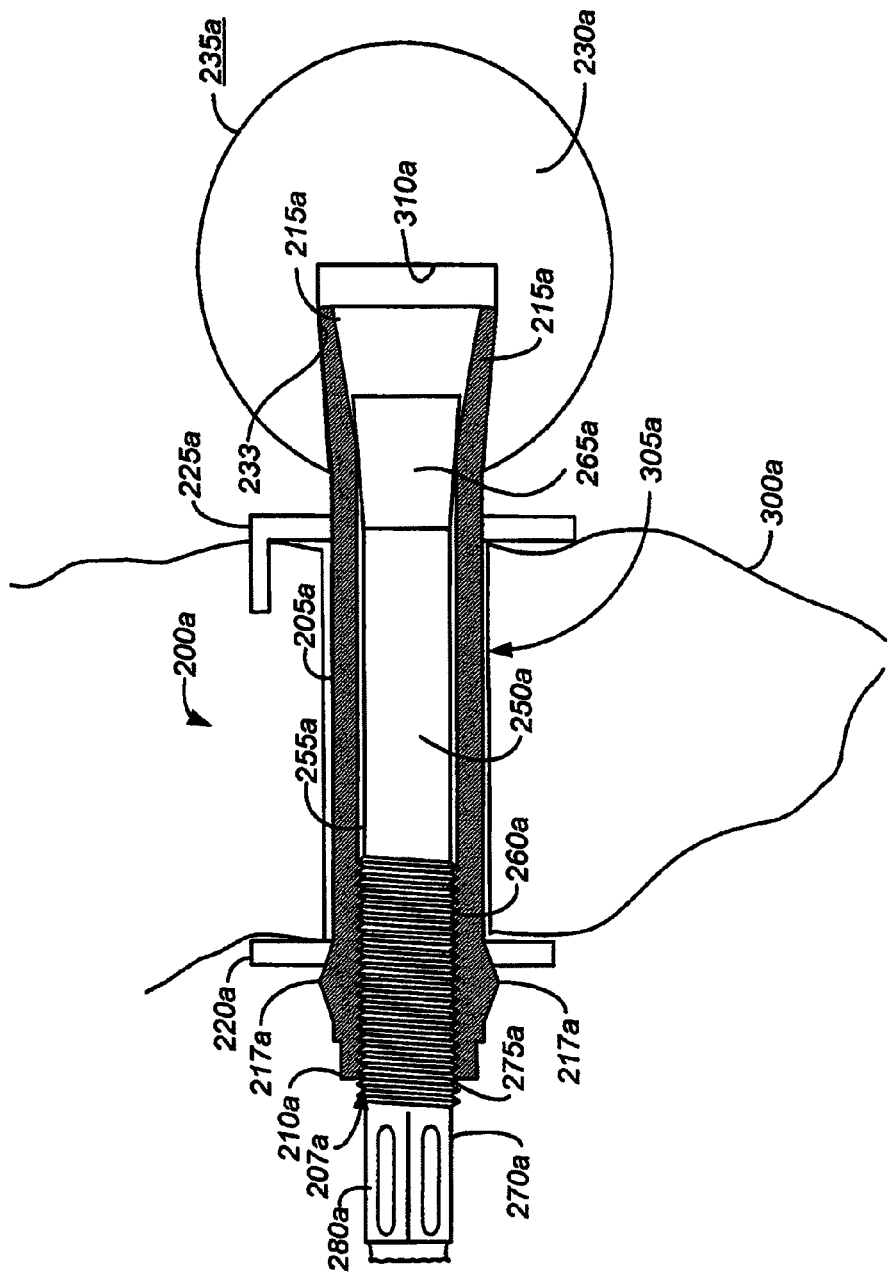
FIG. 28 is a cross-sectional view of the cephalad prosthesis of FIG. 26, showing an alternate re-attachment and placement of the bearing surface element.

In the event that revision and/or removal of the cephalad prosthesis is desired or required, the present embodiment also facilitates revision/removal of the cephalad prosthesis. To remove the prosthesis, the counter-torque wrench 400 can be used to rotate the shaft 250*a* (relative to the body 205*a*) in a direction opposite to the "tightening direction", thereby advancing the shaft 250*a* distally and eventually "pushing" the bearing 230*a* off of the distal end 215*a* of the body 205*a* (FIG. 27). Desirably, removal of the bearing 230*a* will also compress the distal end 215*a* of the body 205*a* to some extent, simplifying removal of the distal collar 225*a* as well as withdrawal of the body 205*a* proximally through the passage 305*a* and ultimately from the treatment site (if so desired). In a similar manner, the caudal bearing surface (or both surfaces) could be repaired and/or replaced and/or repositioned if desired and/or necessary (FIG. 28).

The previously-described procedure could similarly be used to replace a worn and/or damaged bearing surface of a previously-implanted cephalad construct, without requiring removal and/or revision of the entire cephalad implant. Simply removing and replacing the worn or damaged bearing with a new/undamaged bearing, and retightening of the cephalad implant, could be accomplished with little or no disruption to the surrounding tissues. Moreover, such a repair procedure could be accomplished using a first cannula to access the proximal drive section 270*a* and associated components, and a second cannula to access the bearing 230*a* (to remove the old bearing and introduce a new replacement).

In alternate embodiments, the bearing surfaces 235, 235*a* of the bearings 230, 230*a* could be non-spherical (including oval, square, triangular, flattened and/or disk shaped), and could include one or more bearing surfaces 235 (i.e., more than one bearing surface 235 as illustrated in FIG. 15A).

Depending upon the patient's condition and the desired surgical outcome, as well as the surgeon's preference, the present embodiment can facilitate the repair and replacement/augmentation of the facet joints in a minimally-invasive, limited-open (or modified-open) and/or fully-open surgical procedure. For example, where facet joint replacement is deemed necessary, but removal of soft and/or hard tissues in and/or adjacent the spinal canal is not warranted or desired (such as where spinal stenosis and nerve impingement is not a significant concern), the repair and/or replacement of one or more facet joints can be accomplished in a least-invasive fashion, using one or more cannulae to implant the prosthesis and associated distal hardware. Alternatively, where removal of the facet joints and/or lamina is necessitated, such a procedure can be accomplished through a combination of open, semi-open and/or minimally invasive procedures (which will be referred to herein as a modified-open or mini-open procedure) to minimize damage and/or disruption to surrounding soft-tissue structures. In such a procedure, one or more of the facet joint capsules can be exposed through an open incision (to allow easy resection and removal of the facet joint and/or surrounding anatomical structures), and the cephalad component of the facet replacement can be delivered through the lamina through a cannula or other minimally-invasive delivery method.

Another significant advantage attendant with the present embodiment is that the majority of the cephalad prosthesis is positioned within the lamina, with only limited portions of the implant extending outwards from the vertebral body. This arrangement presents a low-profile to the surrounding soft tissue structures, desirably resulting in less interaction between the prosthesis and the surrounding soft tissues, as well as less displacement of natural tissues due to the presence of the implant. Moreover, anchoring the cephalad portion of the prosthesis within the lamina and/or spinous process reduces and/or eliminates to opportunity for unwanted contact between the dura and the prosthesis.

Another significant advantage attendant to various disclosed embodiments results from the location and attachment method of the cephalad portion of the prosthesis. Because the location, length and orientation of the laminar passage created by the surgeon is variable (depending upon the patient's anatomical constraints), a limited variety of implant sizes and/or shapes can accommodate almost any anatomical variation possible in the patient. For example, a kit including the cephalad implant can include cephalad implants having various lengths, including 30, 40, 50 and 60 millimeters, to accommodate passages/lamina having differing lengths/thicknesses. Similarly, the depth of the hole 233 in the bearing 235*a* (to accommodate the distal end of the cephalad component) can vary (by 1 or ½ mm increments, for example) to accommodate anatomical variations in the patient. Thus, the present embodiment and implantation methods reduces the need for a highly-modular and/or configurable cephalad prosthesis. Moreover, the present implant design can accommodate bones of varying dimensions and/or configurations. Moreover, the solid nature of the component retains its strength and durability.

Another significant advantage of various embodiments described herein is the use of the lamina and spinous process as the anchor points for the cephalad portion(s) of the prosthesis. By avoiding use of the pedicles of the cephalad vertebral body to anchor the cephalad prosthesis, the present embodiment (1) reduces the opportunity for unintended damage to and/or intrusion into the facet joint capsule and facet joint structures of the cephalad vertebral level being treated, (2) allows for subsequent or concurrent implantation of additional prosthesis into the pedicles of the cephalad vertebral body, (3) allows unrestricted access to the intervertebral disk and disk structures in event of the need for concurrent or subsequent disk treatment, and (4) utilizes the lamina (and thus the pedicles) to support the prosthesis in a more natural anatomical manner. Desirably, the present embodiment will permit a physician to "daisy-chain" multiple prosthesis along multiple vertebral levels, during either a single surgical procedure or during subsequent surgeries as additional facet joints degrade and/or degenerate.

By anchoring the cephalad prosthesis within the lamina and/or spinous process, rather than within the pedicle, the present embodiment more closely mimics the natural anatomical position and loading of the cephalad facet joint surface and vertebral bodies. Loads which would have originally been transmitted from the inferior facet joint through the lamina and pedicles and into the vertebral body (which would be directly conducted through the pedicle and into the vertebral body by a pedicle-based cephalad implant anchoring system) are now simply transferred through the cephalad prosthesis and into the lamina in a more natural anatomical loading manner. Moreover, the use of the lamina as an anchoring point for the implant significantly reduces the forces experienced by the bone at the anchor (desirably reducing the tendency for the implant to break or loosen over time).

Desirably, the proximal and distal collars can move and/or rotate to a limited degree relative to the cylindrical body of the cephalad implant, such that, when the implant is in position and tightened, the collars will lie relatively flat against the cortical bone walls of the lamina at either or both the proximal and distal ends of the cephalad implant. If desired, the physician can alter one or both sides of the lamina to more readily accommodate the proximal and/or distal collars.

Desirably, the cephalad stems will be secured directly to the lamina and will incorporate a bony-ingrowth surface. Alternatively, the stems can be secured to the lamina using bone-cement or osteo-conductive or osteo-inductive material. Desirably, any such securing material will resist progressive loosening and fracture propagation typically associated with long-term implantation of orthopedic joint replacements.

In another alternate embodiment, the lamina passages could cross through each other, with the bodies of the individual cephalad prosthesis connecting or "linking in one or more manner (either inside the lamina or externally to the lamina, or some combination thereof) to more securely "solidify" the fixation and rigidity of the construct. For example, one cephalad implant could incorporate a through-hole of varying size to accommodate a corresponding distal end of a corresponding implant. Alternatively, the implants could be bridged by a locking collar extending over, under and/or through the spinous process.

In another embodiment, the cephalad implant or portions thereof (i.e., the body 205, 205a) can be non-cylindrical, and the correspondingly shaped passage through the lamina can be created using a chisel, rongeur, broach or "box punch". Such a non-cylindrical implant would desirably resist rotation to a significant degree.

In another alternate embodiments, the cephalad and caudal components of the prosthesis can be linked together to reduce and/or eliminate relative motion between the cephalad and caudal components, and thus between the cephalad and caudal vertebral bodies. For example, where progressive degeneration of the intervertebral disk and/or vertebral bodies renders the spinal motion segment significantly unstable, or where reduction of the relative motion between the vertebral bodies is desired, the cephalad components can be "capped" or locked to the caudal components. Such linking mechanism could include clamps or wraps (such as wire ties) which secure the bearing surface within the caudal cup, as well as adhesives which could secure the components to each other or "fill" a clamp or cup used to "fuse" the articulating surfaces of the implant.

Many of the features of the present embodiment are designed to accommodate significant variability in the anatomy of vertebral bodies. For example, the bearing 235a need not be positioned flush against the distal end 215a, but can rather be secured to the body 205a at various locations, thereby incorporating some length variability into the system (FIG. 28). Similarly, the distal collar 225a and wedge (if used) can be secured to various positions along the body 205a. Similarly, the proximal collar 220a can incorporate an offset through-hole (such as a 15° offset or a 30° offset from perpendicular) to accommodate even greater angular variability in the first outer surface of the lamina 385 relative to the passage 305a. Similar variations are possible for the components in embodiments of prosthesis 200.

Figure 30:
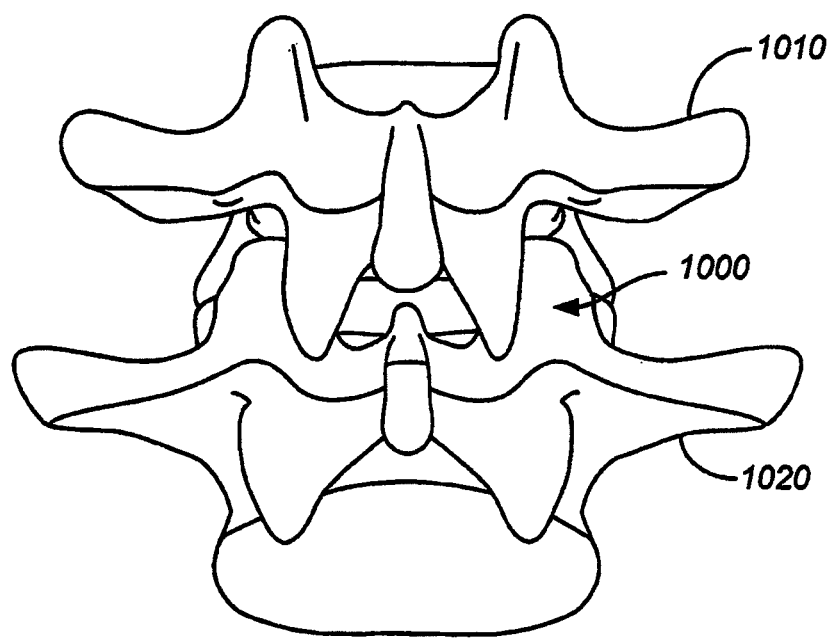
FIG. 30 is a side plan view of a functional spinal unit.
Figure 31:
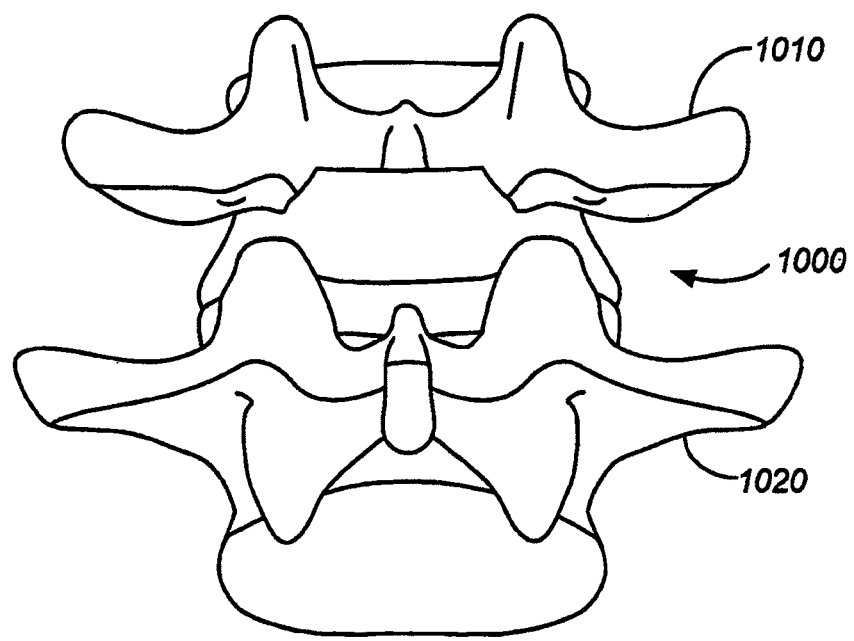
FIG. 31 is a side plan view of the functional spinal unit of FIG. 30, after undergoing a decompressive laminectomy procedure.
Figure 32:
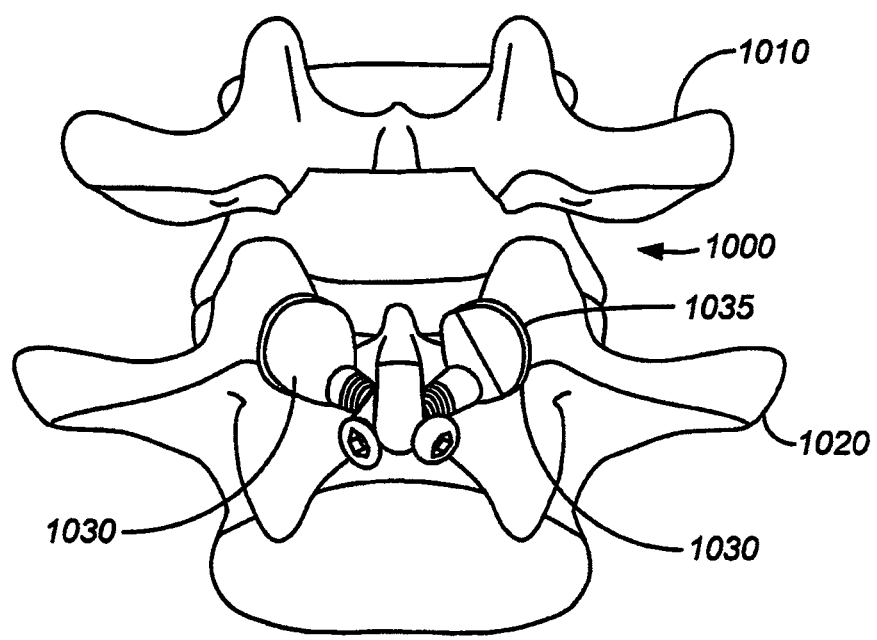
FIG. 32 is a side plan view of the functional spinal unit of FIG. 31, after implantation of one embodiment of a caudal portion of a facet joint replacement prosthesis.

FIGS. 30 through 34 depict other alternate embodiments of facet joint replacement prostheses constructed in accordance with the teachings of the present invention. FIG. 30 illustrates a superior vertebral body 1010, an inferior vertebral body 1020 and a functional spinal unit 1000 (i.e., a pair of facet joints) between the bodies 1010, 1020. In FIG. 31, a portion of the superior vertebral body 1010 and the functional spinal unit 1000 has been removed during a decompressive laminectomy procedure. Depending upon the surgical need, some or all of the posterior portions of one or more vertebral bodies may be damaged or removed, or the area may be weakened by degeneration and/or disease, rendering them unsuitable for anchoring a portion of the prosthesis into and/or through the lamina.

Figure 33:
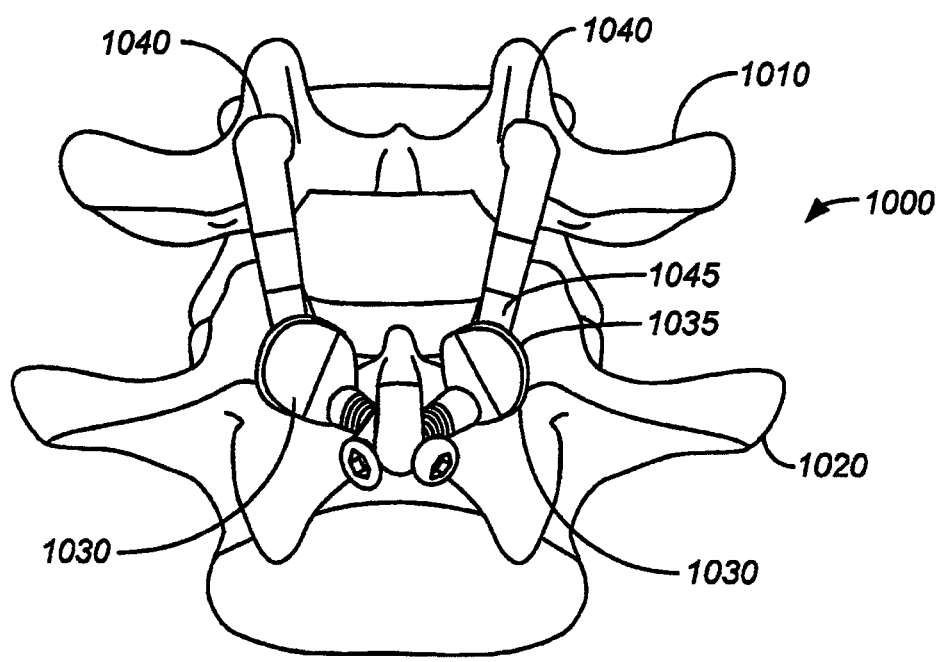
FIG. 33 is a side plan view of the functional spinal unit of FIG. 32, after implantation of one embodiment of a cephalad portion of a facet joint replacement prosthesis.
Figure 34:
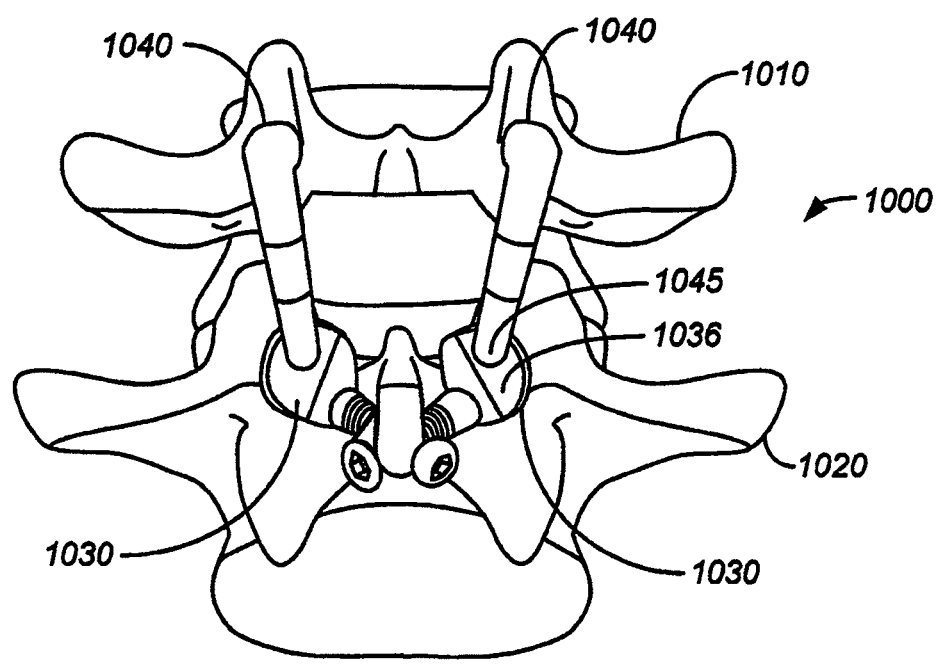
FIG. 34 is a side plan view of the functional spinal unit of FIG. 32, after implantation of another embodiment of a cephalad portion of a facet joint replacement prosthesis.

In the event of weakened posterior portions, embodiments of the present invention may be adapted to attach to different portions of the vertebral body that remain structurally sound. For example, in the illustrated embodiment of FIG. 32 a portion of the prosthesis, in this embodiment the caudal portion 1030 of the prosthesis, can be anchored into the lamina of the inferior vertebral level 1030. However, the superior vertebral body 1010 has a compromised laminar structure. As such, the other portion of the prosthesis, here the cephalad portion 1040 in FIG. 33, is anchored into the pedicles of the superior vertebral body 1010. Desirably, the cephalad and caudal portions 1040 and 1030 articulate with respect to each other through the interactions of one or more bearing surfaces. For example, FIG. 33 illustrates an embodiment where the caudal prosthesis 1030 has a bearing surface 1035 that interacts with the cephalad bearing 1045. The bearing surface 1035 is on an anterior surface of the caudal prosthesis 1030 in the illustrated view. FIG. 34 illustrates another alternative embodiment where the caudal bearing surface 1036 is on a posterior surface of the caudal prosthesis 1030 to interact with the cephalad bearing 1045.

In another alternate embodiment, both the cephalad and caudal portions of the prosthesis could be secured to the lamina and/or spinous process of their respective vertebral bodies using embodiments of the present invention described above with regard to FIGS. 15-28. Advantageously utilizing the lamina and/or spinous process of each vertebra preserves the pedicles of both the cephalad and caudal vertebral levels for future treatment, permit treatment of a level involving previously-existing pedicular fixation, and/or allow treatment of an unfused level bounded by one or more upper and/or lower adjacent fused levels.

Figure 35:
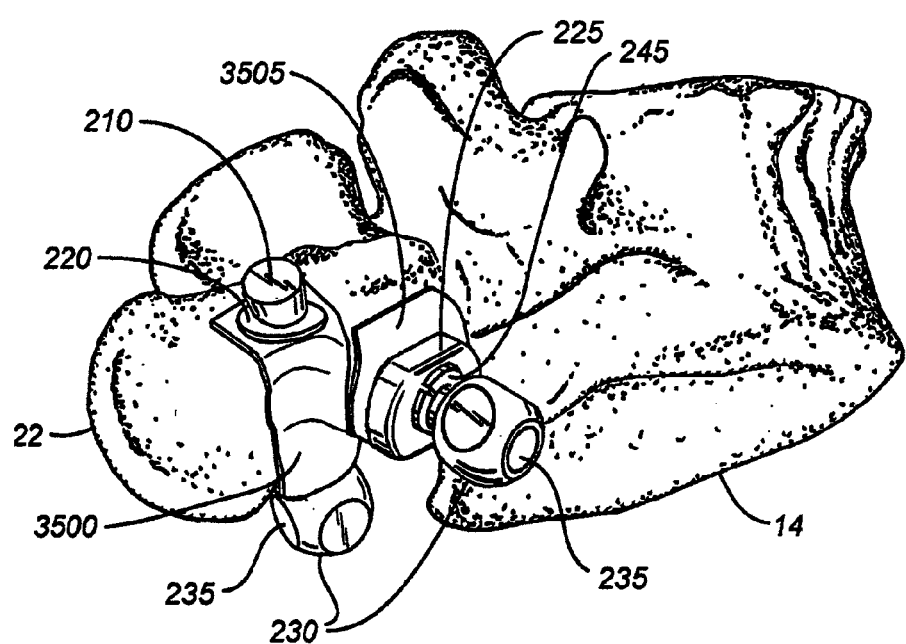
FIG. 35 is a perspective view of two reinforcing material embodiments of the present invention in place with embodiments of the cephalad prosthesis of FIG. 15A.

FIG. 35 illustrates other embodiments of prostheses 200 in place on a vertebral body 14. FIG. 35 illustrates reinforcing materials 3500 and 3505 disposed between collars 225 and 220 and the vertebral bone. In both embodiments, the reinforcing material 3500 and 3505 is desirably "wider" than the adjacent collars and assists in the distribution of the compressive load from the collars to a larger area of the vertebra. These reinforcing materials are formed from any suitable material to distribute such loading, and may be malleable enough to be formed around and contour with the bone (while strong enough to distribute compressive loads), semi-malleable or rigid (and may comprise one or more series of different size and/or shape devices that correspond to varying anatomy of the targeted vertebral body). In various embodiments, the reinforcing material can be formed from or is coated with a biocompatible coating or has a surface in contact with bone that is treated with compounds to promote adhesion to the bone or bone growth.

In one embodiment, the reinforcing material is a strip 3500 desirably having sufficient length to extend from the proximal collar 220, along the bone to the distal collar 225. In another alternative embodiment, the reinforcing material is one or more pads having a larger area than the adjacent collar. In this case, the reinforcing material 3505 is shown adjacent a distal collar 225 (a similar reinforcing material may be placed adjacent the opposite proximal collar, if desired, which is hidden by the lamina in this figure. In additional alternative embodiments, the reinforcing material could be used in conjunction with or in lieu of one or both collars 225, 220.

The various disclosed embodiments can facilitate the implantation of one or more portions of a facet joint prosthesis into a vertebral level that, for a myriad of reasons, cannot accommodate a pedicle-fixation based anchor. Such reasons can include where the pedicular space is already occupied (i.e., where pedicle screws are being used in fusion systems and/or dynamic stabilization), is blocked (i.e. where existing hooks and/or rods block clear access to the pedicle), or where the vertebral body is partially or fully occupied to preclude introduction of pedicle anchors (i.e. where fixation screws for thoraco-lumbar plates pass in front of the pedicle space, or the vertebral body incorporates interbody spacers such as in the K-Centrum Anterior Spinal System™).

It should be understood that the caudal and cephalad bearing surfaces in other embodiments could be reversed, such that the bearing surface of the caudal component could ride inside and/or against a bearing surface of the cephalad component. For example, one or more balls (incorporating convex bearing surfaces) carried by the caudal components could ride inside one or more corresponding cups (incorporating concave bearing surfaces) carried by the cephalad components. In a similar manner, the arms of the caudal components could be longer than the arms of the corresponding cephalad components.

In various alternate embodiments, the disclosed pairs of caudal and cephalad portions of the facet replacement prosthesis described herein could comprise a single caudal and cephalad pair, or more than two caudal and cephalad pairs. Alternatively, the disclosed caudal pair could comprise a single caudal portion, with one or a plurality of cephalad portions, and vice versa. In such an arrangement, the plurality of portions could interact with a single bearing surface on the corresponding single portion, or multiple bearing surfaces on the corresponding single portion of the prosthesis.

While the disclosed bearing surface 235*a* is spherical in shape, the bearing surface 235*a* could be a myriad of shapes, including other geometric configurations as well as flat, convex or concave surfaces. In one embodiment, the bearing surface could comprise a relatively flat surface having a convex face, similar to the surface of the facet joint it replaces.

The above described embodiments of this invention are merely descriptive of its principles and are not to be limited. The scope of this invention instead shall be determined from the scope of the following claims, including their equivalents.

What is claimed is:

1. A method of stabilizing a spinal motion segment, comprising:
    accessing a facet joint of the spinal motion segment;
    resecting all or a portion of the facet joint to provide a surgical access path through at least a portion of the resected all or a portion of the facet joint; and
    implanting a first facet replacement prosthesis to replace a portion of the facet joint, wherein the first facet replacement prosthesis is positioned on a first location of a vertebra; and
    implanting a second facet replacement prosthesis to replace a different portion of the facet joint, wherein the second facet replacement prosthesis is positioned on a second location of the same vertebra;
    wherein the first facet replacement prosthesis and the second facet replacement prosthesis are independent and not connected to one another, and
    wherein the first facet replacement prosthesis extends through a spinous process of the vertebra and the second facet replacement prosthesis extends through the spinous process of the vertebra.

2. The method of claim 1, wherein the step of implanting the first facet replacement prosthesis occurs after introducing an artificial disc replacement prosthesis first through the surgical access path.

3. The method of claim 1, wherein the resecting step comprises resecting at least a portion of the superior facet and the inferior facet of the facet joint.

4. The method of claim 3, wherein the resecting step further comprises resecting all of the superior and inferior facets of a second facet joint of the spinal motion segment.

5. The method of claim 1, wherein the resecting step further comprises resecting a portion of the lamina of the spinal level.

6. The method of claim 1, wherein all of the surgical steps occur percutaneously.

7. The method of claim 1, wherein all of the surgical steps are performed using a combination of open and percutaneous surgical accesses.

8. The method of claim 1, wherein at least one of the surgical steps is performed through a cannula.

9. The method of claim 8, wherein at least one of the surgical steps is performed through an expanding cannula.

10. The method of claim 1, wherein the first facet replacement prosthesis is implanted without disruption to the supraspinous and/or inter-spinous ligaments.

11. The method of claim 1, wherein a facet capsule is opened and removed before or during resecting all or a portion of the facet joint.

12. The method of claim 1, wherein the first facet replacement prosthesis extends along a first axis through the spinous process and the second facet replacement prosthesis extends along a second axis through the spinous process, wherein the first axis is different from the second axis.

13. A method of stabilizing a spinal motion segment, comprising:
    accessing a facet joint of the spinal motion segment;
    resecting all or a portion of the facet joint to provide a surgical access path through at least a portion of the resected all or a portion of the facet joint; and
    implanting a first facet replacement prosthesis to replace a portion of the facet joint, wherein the first facet replacement prosthesis extends along a first axis through a spinous process; and
    implanting a second facet replacement prosthesis to replace a different portion of the facet joint, wherein the second facet replacement prosthesis prosthesis extends along a second axis, different from the first axis, through the spinous process;
    wherein the first facet replacement prosthesis and the second facet replacement prosthesis are independent and not connected to one another.

14. The method of claim 13, wherein the step of implanting the first facet replacement prosthesis occurs after introducing an artificial disc replacement prosthesis first through the surgical access path.

15. The method of claim 13, wherein the resecting step comprises resecting at least a portion of the superior facet and the inferior facet of the facet joint.

16. The method of claim 15, wherein the resecting step further comprises resecting all of the superior and inferior facets of a second facet joint of the spinal motion segment.

17. The method of claim 13, wherein the resecting step further comprises resecting a portion of the lamina of the spinal level.

18. The method of claim 13, wherein all of the surgical steps occur percutaneously.

19. The method of claim 13, wherein all of the surgical steps are performed using a combination of open and percutaneous surgical accesses.

20. The method of claim 13, wherein at least one of the surgical steps is performed through a cannula.

* * * * *